(12) United States Patent
Kiuchi et al.

(10) Patent No.: US 8,114,902 B2
(45) Date of Patent: Feb. 14, 2012

(54) 2-AMINOBUTANOL COMPOUND AND USE THEREOF FOR MEDICAL PURPOSES

(75) Inventors: Masatoshi Kiuchi, Tokyo (JP); Mitsuharu Nakamura, Tokyo (JP); Maiko Hamada, Tokyo (JP); Kunio Sugahara, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 481 days.

(21) Appl. No.: 12/226,745

(22) PCT Filed: Apr. 27, 2007

(86) PCT No.: PCT/JP2007/059150
§ 371 (c)(1),
(2), (4) Date: Nov. 26, 2008

(87) PCT Pub. No.: WO2007/126042
PCT Pub. Date: Nov. 8, 2007

(65) Prior Publication Data
US 2009/0082311 A1   Mar. 26, 2009

(30) Foreign Application Priority Data
Apr. 28, 2006   (JP) .................................. 2006-126102

(51) Int. Cl.
*A61K 31/335*   (2006.01)
*C07D 319/06*   (2006.01)
(52) U.S. Cl. ........................................ 514/452; 549/369
(58) Field of Classification Search ................. 514/452; 549/369
See application file for complete search history.

(56) References Cited

FOREIGN PATENT DOCUMENTS

| EP | 1431284 A1 | 6/2004 |
|---|---|---|
| JP | 2004-307440 A | 11/2004 |
| JP | 2005-527612 A | 9/2005 |
| WO | WO-94/08943 A1 | 4/1994 |
| WO | WO-96/06068 A1 | 2/1996 |
| WO | WO-98/45429 A2 | 10/1998 |
| WO | WO-03/029205 A1 | 4/2003 |
| WO | WO-03/099192 A2 | 12/2003 |

OTHER PUBLICATIONS

Luker et al., 2007, CAS: 146:401688.*
Fan et al., 2003, CAS: 140:4842.*
Matloublan et al., "*Lymphocyte egress* from thymus and peripheral lymphoid organs is dependent on S1P receptor 1", Nature vol. 427, Jan. 22, 2004, pp. 355-360.
Mandala et al., "Alternation of Lymphocyte Trafficking by *Sphingosine*-1-Phosphate Receptor Agonists", Science vol. 296, Apr. 12, 2002, pp. 346-349.

* cited by examiner

*Primary Examiner* — Rei-tsang Shiao
(74) *Attorney, Agent, or Firm* — Birch, Stewart, Kolasch & Birch, LLP

(57) ABSTRACT

Disclosed is a 2-aminobutanol compound represented by the following formula (I)

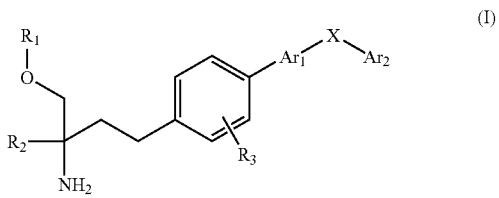

or a pharmaceutically acceptable acid addition salt thereof, or a hydrate thereof, or a solvate thereof, as well as a production method of the 2-aminobutanol compound of formula (I). The 2-aminobutanol compounds of formula (I) have few side effects including bradycardia and have superior peripheral blood lymphocyte-decreasing effects.

11 Claims, No Drawings

2-AMINOBUTANOL COMPOUND AND USE THEREOF FOR MEDICAL PURPOSES

TECHNIQUE FIELD

The present invention relates to a 2-aminobutanol compound, use thereof as a pharmaceutical agent, and a production method thereof.

BACKGROUND ART

In recent years, calcineurin inhibitors such as ciclosporin and FK506 have been used to prevent rejection of patients who underwent organ transplantation. However, a certain kind of calcineurin inhibitor like ciclosporin sometimes causes adverse side effects such as nephrotoxicity, hepatotoxicity, neurotoxicity and the like. In an attempt to prevent rejection in transplant patients, therefore, the development of a safer and more effective pharmaceutical agent is ongoing.

Patent references 1-3 disclose 2-aminopropane-1,3-diol compounds useful as agents for preventing (acute or chronic) rejection in organ or bone marrow transplantation, or therapeutic drugs for various autoimmune diseases such as psoriasis, Behcet's disease and the like and rheumatic affection.

One of such compounds, 2-amino-2-[2-(4-octylphenyl) ethyl]propane-1,3-diol hydrochloride (hereinafter sometimes to be abbreviated as FTY720) is a compound currently under clinical development as an agent for preventing rejection in renal transplantation. FTY720 is rapidly converted by sphingosine kinase into phosphorylated FTY720 [hereinafter sometimes to be referred to as FTY720-P, e.g., (±)2-amino-2-phosphoryloxymethyl-4-(4-octylphenyl)butanol] in the body. FTY720-P acts as an agonist on 4 kinds of sphingosine-1-phosphate (hereinafter sometimes to be referred to as S1P) receptors (other than S1P2) out of 5 kinds of S1P receptors (hereinafter sometimes to be referred to as S1P1-5, respectively) (non-patent reference 1).

Recently, it has been reported that S1P1 out of the S1P receptors is essential for the transfer of mature lymphocytes from the thymus and secondary lymphoid tissues. FTY720-P down regulates S1P1 on lymphocytes by acting as an S1P1 agonist. Consequently, it is suggested that transfer of mature lymphocytes from the thymus and secondary lymphoid tissues is inhibited, and circulating mature lymphocytes in the blood are isolated in the secondary lymphoid tissues, whereby an immunosuppressive action is exerted (non-patent reference 2).

On the other hand, conventional 2-aminopropane-1,3-diol compounds are feared to cause side effects of transient bradycardia expression. To solve the problem, many novel compounds obtained by chemical structural modification of 2-aminopropane-1,3-diol compounds have been reported. Among those, as a compound having a biaryl structure in the hydrophobic carbon chain FTY720 has, patent reference 4 discloses a biaryl compound having substituent(s) as an S1P receptor modulator. In addition, patent reference 5 discloses a biaryl compound having a certain kind of substituent, which is useful as an immunosuppressant. However, they do not disclose arylthio, aryloxy, arylcarbonyl, arylamino and the like as the substituents possessed by the biaryl structure. In any case, they have not reached a satisfactory level regarding the safety of a pharmaceutical product.
patent reference 1: WO94/08943
patent reference 2: WO96/06068
patent reference 3: WO98/45429
patent reference 4: WO03/099192
patent reference 5: JP-A-2004-307440 non-patent reference 1: Science, 2002, No. 296, pp. 346-349
non-patent reference 2: Nature, 2004, No. 427, pp. 355-360

DISCLOSURE OF THE INVENTION

Problems to be Solved by the Invention

An object of the present invention is to provide a novel 2-aminobutanol compound superior in the immunosuppressive action, anti-rejection action and the like, which causes a fewer side effects of bradycardia and the like.

Means of Solving the Problems

In consideration of the above-mentioned situation, the present inventors have made further studies and found that a 2-aminobutanol compound having the below-mentioned particular structural formula can achieve the desired object and completed the present invention. In addition, they have found that a synthesis method of the compound of the present invention is useful for the synthesis of diphenyl sulfide or phenyl thienyl sulfide having an aminobutanol backbone as a partial structure in the substituent.

Accordingly, the present invention provides the following.
(1) A 2-aminobutanol compound represented by the following formula (I)

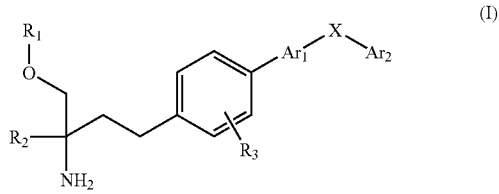

wherein
$R_1$ is a hydrogen atom or $P(=O)(OH)_2$,
$R_2$ is an alkyl having 1 to 4 carbon atoms optionally substituted by hydroxyl group(s) or optionally substituted by halogen atom(s),
$R_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s),
X is an oxygen atom, a sulfur atom, carbonyl or $NR_4$ wherein $R_4$ is a hydrogen atom or an alkyl having 1 to 4 carbon atoms,
$Ar_1$ is an optionally substituted arylene or an optionally substituted heteroarylene, and
$Ar_2$ is an optionally substituted aryl or an optionally substituted heteroaryl,
provided that when X is an oxygen atom, $Ar_1$ is phenylene and $Ar_2$ is phenyl, then the phenyl for $Ar_2$ should be substituted,
or a pharmaceutically acceptable acid addition salt thereof, or a hydrate thereof, or a solvate thereof.
(2) The 2-aminobutanol compound of (1), wherein X is a sulfur atom, or a pharmaceutically acceptable acid addition salt thereof, or a hydrate thereof, or a solvate thereof.
(3) The 2-aminobutanol compound of (1) or (2), wherein $R_3$ is a hydrogen atom or a halogen atom, or a pharmaceutically acceptable acid addition salt thereof, or a hydrate thereof, or a solvate thereof.
(4) The 2-aminobutanol compound of any one of (1) to (3), wherein $Ar_1$ is an optionally substituted arylene, or a pharmaceutically acceptable acid addition salt thereof, or a hydrate thereof, or a solvate thereof.

(5) The 2-aminobutanol compound of any one of (1) to (4), wherein $Ar_2$ is an optionally substituted aryl, or a pharmaceutically acceptable acid addition salt thereof, or a hydrate thereof, or a solvate thereof.

(6) The 2-aminobutanol compound of any one of (1) to (5), which is represented by the following formula (Ia)

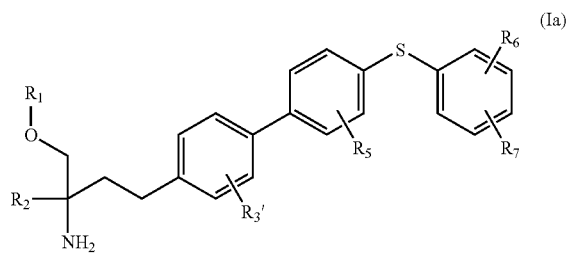

(Ia)

wherein
$R_1$ is a hydrogen atom or $P(=O)(OH)_2$,
$R_2$ is an alkyl having 1 to 4 carbon atoms optionally substituted by hydroxyl group(s) or optionally substituted by halogen atom(s),
$R_3'$ is a hydrogen atom or a halogen atom,
$R_5$ is a hydrogen atom or a halogen atom, and
$R_6$ and $R_7$ are the same or different, and each is a hydrogen atom; an alkyl having 1 to 4 carbon atoms optionally substituted by halogen atom(s); an alkoxy having 1 to 4 carbon atoms; or a halogen atom,
or a pharmaceutically acceptable acid addition salt thereof, or a hydrate thereof, or a solvate thereof.

(7) The compound of any one of (1) to (6), wherein the compound of the formula (I) is any of the following compounds a and b, or a pharmaceutically acceptable acid addition salt thereof, or a hydrate thereof, or a solvate thereof:
a. 2-amino-2-{2-[2'-fluoro-4'-(4-methylphenylthio)biphenyl-4-yl]ethyl}propane-1,3-diol
b. 2-amino-4-[2'-fluoro-4'-(4-methylphenylthio)biphenyl-4-yl]-2-(phosphoryloxymethyl)butanol.

(8) 2-Amino-2-{2-[2'-fluoro-4'-(4-methylphenylthio)biphenyl-4-yl]ethyl}propane-1,3-diol, or a hydrochloride thereof.

(9) A pharmaceutical composition comprising the compound of any one of (1) to (8) and pharmaceutically acceptable carrier.

(10) The pharmaceutical composition of (9), which is used for the treatment or prophylaxis of autoimmune diseases; the prophylaxis or prevention of acute rejection or chronic rejection due to organ or tissue transplantation; the treatment or prophylaxis of graft vs host (GvH) disease due to bone marrow transplantation; or the treatment or prophylaxis of allergic diseases.

(11) A production method of a compound represented by the formula (II-4), which comprises condensing a benzene compound having a leaving group $X^c$, which is represented by the formula (II-1) with a benzenethiol represented by the formula (II-2) or condensing a thiol compound represented by the formula (II-1') with a benzene compound having a leaving group $X^c$, which is represented by the formula (II-2') to give a compound represented by the formula (II-3), and subjecting the compound to deprotection,

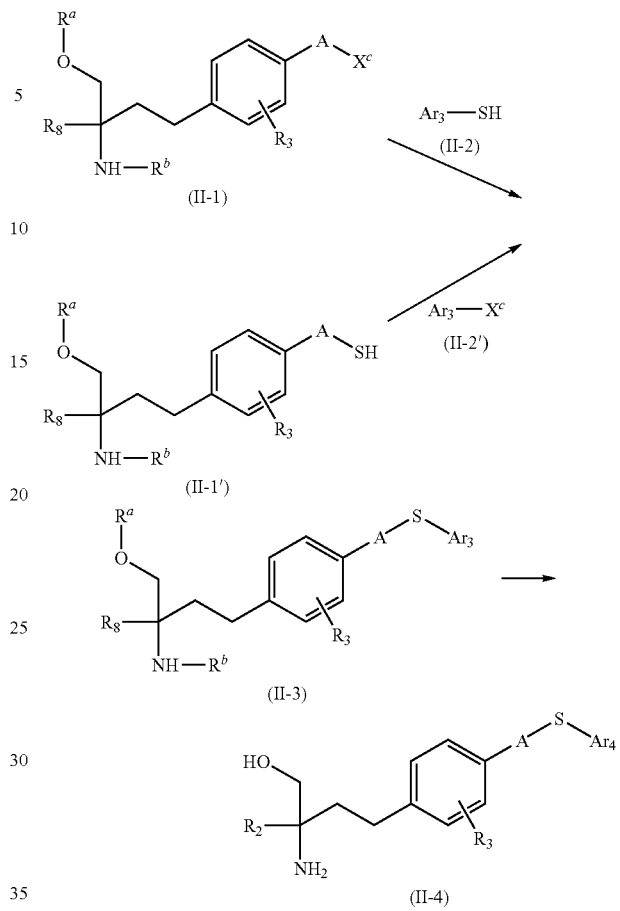

wherein
$R_8$ is an alkyl having 1 to 4 carbon atoms optionally substituted by hydroxyl group(s) optionally protected or optionally substituted by halogen atom(s),
$R_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s),
$Ar_3$ is an optionally substituted aryl, an optionally substituted heteroaryl, phenyl substituted by hydroxyl group(s) optionally protected, or benzyloxyphenyl,
A is an optionally substituted arylene, an optionally substituted heteroarylene or a single bond,
$R^a$ and $R^b$ are each a hydrogen atom or a protecting group,
$X^c$ is a leaving group,
$R_2$ is an alkyl having 1 to 4 carbon atoms optionally substituted by hydroxyl group(s) or optionally substituted by halogen atom(s), and
$Ar_4$ is an optionally substituted aryl, an optionally substituted heteroaryl, phenyl substituted by hydroxyl group(s), or benzyloxyphenyl.

(12) A production method of a compound represented by the formula (II-3), which comprises condensing a benzene compound having a leaving group $X^c$, which is represented by the formula (II-1) with a benzenethiol represented by the formula (II-2),

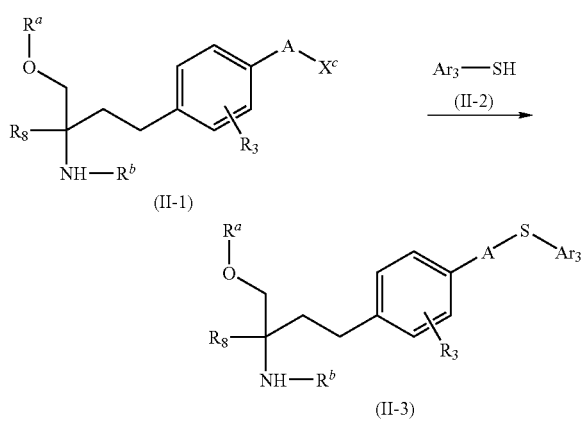

wherein
R$_8$ is an alkyl having 1 to 4 carbon atoms optionally substituted by hydroxyl group(s) optionally protected or optionally substituted by halogen atom(s),
R$_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s),
Ar$_3$ is an optionally substituted aryl, an optionally substituted heteroaryl, phenyl substituted by hydroxyl group(s) optionally protected, or benzyloxyphenyl,
A is an optionally substituted arylene, an optionally substituted heteroarylene or a single bond,
R$^a$ and R$^b$ are each a hydrogen atom or a protecting group, and X$^c$ is a leaving group.

(13) A production method of a compound represented by the formula (II-3), which comprises condensing a thiol compound represented by the formula (II-1') with a benzene compound having a leaving group X$^c$, which is represented by the formula (II-2'),

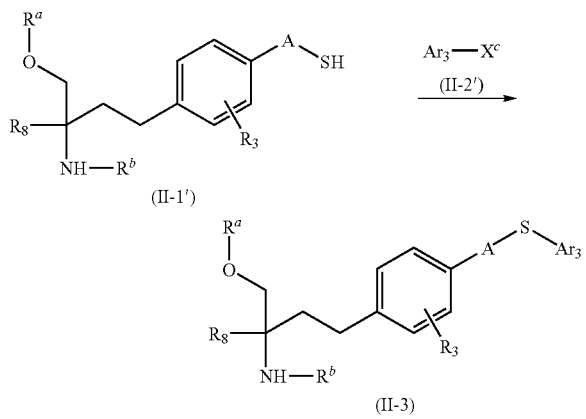

wherein
R$_8$ is an alkyl having 1 to 4 carbon atoms optionally substituted by hydroxyl group(s) optionally protected or optionally substituted by halogen atom(s),
R$_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s),
Ar$_3$ is an optionally substituted aryl, an optionally substituted heteroaryl, phenyl substituted by hydroxyl group(s) optionally protected, or benzyloxyphenyl,
A is an optionally substituted arylene, an optionally substituted heteroarylene or a single bond,
R$^a$ and R$^b$ are each a hydrogen atom or a protecting group, and X$^c$ is a leaving group.

EFFECT OF THE INVENTION

According to the present invention, a novel compound having a superior peripheral blood lymphocyte-decreasing effect, which shows reduced side effects of bradycardia and the like, can be provided.

BEST MODE FOR CARRYING OUT THE INVENTION

The present invention is explained in detail in the following.
The compound of the present invention is a 2-aminobutanol compound represented by the following formula (I):

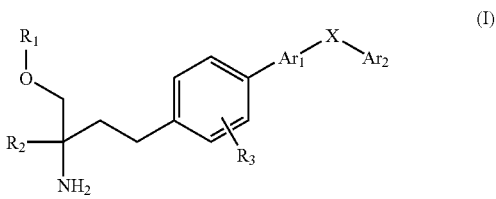

wherein
R$_1$ is a hydrogen atom or P(=O) (OH)$_2$,
R$_2$ is an alkyl having 1 to 4 carbon atoms optionally substituted by hydroxyl group(s) or optionally substituted by halogen atom(s),
R$_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s),
X is an oxygen atom, a sulfur atom, carbonyl or NR$_4$ wherein R$_4$ is a hydrogen atom or an alkyl having 1 to 4 carbon atoms,
Ar$_1$ is an optionally substituted arylene or an optionally substituted heteroarylene, and
Ar$_2$ is an optionally substituted aryl or an optionally substituted heteroaryl,
provided that when X is an oxygen atom, Ar$_1$ is phenylene, and Ar$_2$ is phenyl, then the phenyl for Ar$_2$ should be substituted, or a pharmaceutically acceptable acid addition salt thereof, or a hydrate thereof, or a solvate thereof.

In the present invention, examples of the halogen atom include a fluorine atom, a chlorine atom, a bromine atom and an iodine atom, a fluorine atom and a chlorine atom are preferable.

The alkyl having 1 to 4 carbon atoms means a straight chain or branched chain alkyl having 1 to 4 carbon atoms, and examples thereof include methyl, ethyl, n-propyl, isopropyl, n-butyl, isobutyl, secondary butyl, tertiary butyl (hereinafter "tertiary" is sometimes to be indicated as t- or tert-) and the like.

When the alkyl having 1 to 4 carbon atoms is substituted by hydroxyl group(s), the alkyl is substituted by 1 to 2 hydroxyl groups. Specific examples include hydroxymethyl, 1-hydroxyethyl, 2-hydroxyethyl and the like.

When the alkyl having 1 to 4 carbon atoms is substituted by halogen atom(s), the alkyl is substituted by 1 to 5 halogen atoms. Specific examples include fluoromethyl, difluoromethyl, trifluoromethyl, 1,1-difluoroethyl, 2,2-difluoroethyl, 2,2,2-trifluoroethyl, 2,2,2-trichloroethyl, perfluoroethyl, 3-fluoropropyl, 3,3,3-trifluoropropyl, 4-fluorobutyl and the like.

The acyl having 2 to 5 carbon atoms means a group represented by R—CO— wherein R is an alkyl having 1 to 4 carbon atoms as defined above. When the acyl having 2 to 5 carbon atoms is substituted by halogen group(s), the alkyl moiety is substituted by 1 to 5 halogen atoms.

The aryl means a monocycle or fused aromatic ring having 6 to 10 carbon atoms, and examples thereof include phenyl and naphthyl.

The heteroaryl means a monocycle or fused aromatic ring consisting of 5 to 9 elements, and containing 1 to 3 hetero atoms selected from nitrogen, oxygen and sulfur. Examples thereof include thienyl, pyrrolyl, thiazolyl, isoxazolyl, benzothienyl, indolyl and the like.

The arylene means an aryl having two bonds, and examples thereof include phenylene and naphthylene.

The heteroarylene means the aforementioned heteroaryl having two bonds. Examples thereof include thienylene, thiazolylene, pyridinylene, benzothienylene and the like, and thienylene is preferable.

When the aforementioned "aryl", "heteroaryl", "arylene" or "heteroarylene" has substituent(s), specific examples of the substituent include a halogen atom, an alkyl having 1 to 4 carbon atoms optionally substituted by halogen atom(s), an alkoxy having 1 to 4 carbon atoms optionally substituted by halogen atom(s), an cycloalkyl having 3 to 7 carbon atoms optionally substituted by halogen atom(s), an acyl having 2 to 5 carbon atoms optionally substituted by halogen atom(s) and cyano. The number of the substituents is preferably 1 to 3.

Examples of the alkyl having 1 to 4 carbon atoms optionally substituted by halogen atom(s) and the acyl having 2 to 5 carbon atoms optionally substituted by halogen atom(s) are as described above.

The alkoxy having 1 to 4 carbon atoms means a straight chain or branched chain alkoxy having 1 to 4 carbon atoms. Examples thereof include methoxy, ethoxy, n-propoxy, isopropoxy, n-butoxy, isobutoxy, secondary butoxy, tertiary butoxy (hereinafter "tertiary" is sometimes to be indicated as t- or tert-) and the like, and methoxy is preferable.

When the alkoxy having 1 to 4 carbon atoms is substituted by halogen atom(s), the alkoxy is substituted by 1 to 5 halogen atoms. Specific examples include fluoromethoxy, difluoromethoxy, trifluoromethoxy, 1,1-difluoroethoxy, 2,2-difluoroethoxy, 2,2,2-trifluoroethoxy, 2,2,2-trichloroethoxy, perfluoroethoxy, 3-fluoropropoxy, 3,3,3-trifluoropropoxy, 4-fluorobutoxy and the like.

Examples of the cycloalkyl having 3 to 7 carbon atoms include cyclopropyl, cyclobutyl, cyclopentyl, cyclohexyl, cyclopropylmethyl, cyclobutylmethyl, cyclopentylmethyl, cyclohexylmethyl and the like. When the cycloalkyl having 3 to 7 carbon atoms is substituted by halogen atom(s), the cycloalkyl is substituted by 1 to 5 halogen atoms.

$R_2$ is preferably methyl, ethyl, hydroxymethyl, hydroxyethyl, hydroxypropyl, fluoromethyl, fluoroethyl, 2,2-difluoroethyl or 2,2,2-trifluoroethyl, more preferably methyl, ethyl, hydroxymethyl or hydroxyethyl, still more preferably methyl or hydroxymethyl, particularly preferably hydroxymethyl.

$R_3$ is preferably a hydrogen atom or a chlorine atom.

X is preferably an oxygen atom, a sulfur atom or carbonyl, more preferably a sulfur atom.

$Ar_1$ is preferably an optionally substituted naphthylene, an optionally substituted phenylene or an optionally substituted thienylene. The substituent which $Ar_1$ optionally has is preferably a halogen atom, or an alkyl having 1 to 4 carbon atoms optionally substituted by halogen atom(s), more preferably a fluorine atom. $Ar_1$ is more preferably naphthylene, thienylene or a phenylene substituted by fluorine atom(s), particularly preferably a phenylene substituted by fluorine atom(s).

$Ar_2$ is preferably an optionally substituted phenyl or an optionally substituted thienyl. The substituent which $Ar_2$ optionally has is preferably a halogen atom, an alkyl having 1 to 4 carbon atoms optionally substituted by halogen atom(s), or an alkoxy having 1 to 4 carbon atoms, more preferably a fluorine atom, methyl, ethyl, isopropyl, trifluoromethyl or methoxy, particularly preferably methyl. $Ar_2$ is more preferably phenyl, methylphenyl, ethylphenyl, fluorophenyl, phenyl substituted by fluorine atom(s) and methyl, chlorophenyl, methylthienyl, (trifluoromethyl)phenyl, dimethylphenyl, methoxyphenyl or isopropylphenyl, particularly preferably methylphenyl.

Examples of the pharmaceutically acceptable acid addition salt of the compound of the present invention include inorganic acid salts, organic acid salts and the like. In addition, hydrates thereof and solvates thereof are encompassed in the compound of the present invention, besides the above-mentioned compound of the formula (I) and pharmaceutically acceptable acid addition salts thereof.

Specific examples of the compound of the present invention include the following compounds and pharmaceutically acceptable acid addition salts thereof, and hydrates thereof and solvates thereof:

(1) 2-amino-2-{2-[2'-fluoro-4'-(4-methylphenylthio)biphenyl-4-yl]ethyl}propane-1,3-diol, (2) 2-amino-4-[2'-fluoro-4'-(4-methylphenylthio)biphenyl-4-yl]-2-(phosphoryloxymethyl)butanol.

Of the compound of the present invention, 2-amino-2-{2-[2'-fluoro-4'-(4-methylphenylthio)biphenyl-4-yl]ethyl}propane-1,3-diol and hydrochloride thereof are preferable.

Examples of the synthesis method of the compound of the present invention include the following methods.

1) Compound (1-1), which is the compound of the present invention wherein, in the formula (I), $R_1$ is a hydrogen atom, is synthesized according to the following scheme (III).

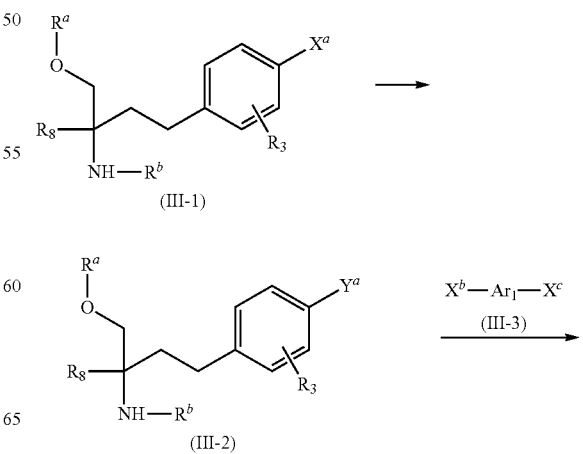

Scheme (III)

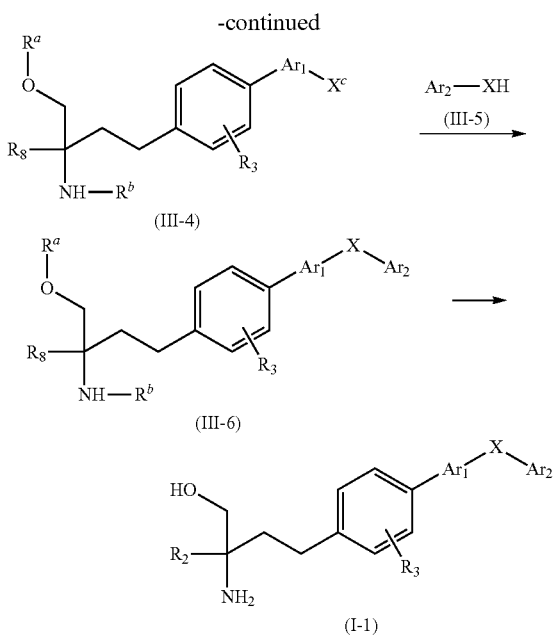

wherein $R^a$ and $R^b$ are each a hydrogen atom or a protecting group, $X^a$, $X^b$ and $X^c$ are each a leaving group, $Y^a$ is an activated group during condensation reaction, and the other symbols are as defined above.

$R^a$ is not particularly limited as long as it is a hydrogen atom or a group capable of protecting a hydroxyl group. Examples thereof include an acyl (preferably an acyl having about 2 to 4 carbon atoms, specifically acetyl and the like), a trialkylsilyl (specifically trimethylsilyl and the like), benzyl and a protecting group capable of forming acetal (specifically methoxymethyl, tetrahydropyranyl and the like). When $R_8$ is a protected hydroxyl group, the protecting group $R^c$ (as $R^c$, those similar to $R^a$ can be mentioned) is optionally bonded to $R^a$ to form a cyclic acetal. $R^b$ is not particularly limited as long as it is a hydrogen atom or a group capable of protecting an amino group. Examples thereof include an acyl (preferably an acyl having about 2 to 4 carbon atoms, specifically acetyl and the like), a carbamate (specifically t-butoxycarbonyl and benzyloxycarbonyl) and the like. The leaving group for $X^a$, $X^b$ or $X^c$ is not particularly limited as long as it can be removed during the introduction reaction of the activated group $Y^a$ or condensation reaction. Examples thereof include a halogen atom (preferably iodine atom, bromine atom and the like), trifluoromethanesulfonyloxy and the like. Examples of the activated group for $Y^a$ include a substituent containing a metal element such as lithium, magnesium and the like, and a substituent containing a non-metal element such as silicon, boron and the like. The above-mentioned leaving group and activated group are used in combination as appropriate, depending on the kind of the condensation reaction.

The first step is a step of converting compound (III-1) having the leaving group $X^a$ to intermediate (III-2) having the activated group $Y^a$ Compound (III-1), which is the starting material for this step, can be synthesized according to a known method (e.g., WO03/029184) using a malonic acid derivative, or a known method (e.g., Organic Letters, vol. 5, 2003, pages 4017-4020) using an acetylene compound, or a known method (e.g., WO03/099192) using a Wittig reaction. The conditions of this step are appropriately selected depending on the kind of $Y^a$. For example, when $Y^a$ is a boronate ester, the following conditions can be used. The reaction can be carried out using, as a solvent, an ether solvent such as 1,4-dioxane, tetrahydrofuran and the like, or a polar solvent such as N,N-dimethylformamide, dimethyl sulfoxide and the like, in the presence of a base and a palladium catalyst. As the base, organic bases such as potassium acetate, diisopropylethylamine and the like, and inorganic bases such as cesium carbonate, tripotassium phosphate and the like can be used. As the palladium catalyst, palladium complexes such as dichlorobis(tricyclohexylphosphine)palladium (II), dichloro[1,1'-bis(diphenylphosphino)ferrocene]palladium (II) and the like can be used. In addition, a palladium compound such as palladium acetate and the like and a reaction aid such as tri-t-butylphosphine and the like are also used in combination. As the boric acid reagent, diboron compounds such as bis(neopentyl glycolato)diboron, bis(pinacolate)diboron and the like can be used. The reaction is carried out at room temperature to under reflux for about 30 min to 24 hr. After the reaction, the reaction mixture is subjected to extraction, washing, drying, solvent evaporation and the like according to a conventional method, and purified by silica gel column chromatography, recrystallization and the like as necessary to give the object compound.

The second step is a step of condensing intermediate (III-2) having the activated group $Y^a$ with compound (III-3) having the leaving group $X^b$ to give biaryl compound (III-4). The condition of this step is appropriately selected depending on the kind of $Y^a$ and $X^b$. For example, when $Y^a$ is a boronate ester, general conditions for Suzuki coupling can be used. Specifically, the reaction can be carried out in an ether solvent such as 1,2-dimethoxyethane, tetrahydrofuran and the like, a hydrocarbon solvent such as toluene and the like, or a highly-polar solvent such as N,N-dimethylformamide and the like, in the presence of a base such as cesium carbonate, tripotassium phosphate and the like and a palladium catalyst. Alternatively, the reaction can also be carried out in a water-containing or two-layer solvent (e.g., tetrahydrofuran and water, 1,2-dimethoxyethane and water), in the presence of a base such as sodium hydroxide, sodium carbonate, thallium hydroxide and the like and a palladium catalyst. In addition, a reaction aid such as 2-dicyclohexylphosphino-2',6'-dimethoxybiphenyl, 2-(di-t-butylphosphino)biphenyl and the like can be added if necessary. The reaction is carried out at room temperature to under reflux for about 30 min to 24 hr. After the reaction, the reaction mixture is subjected to extraction, washing, drying, solvent evaporation and the like according to a conventional method, and purified by silica gel column chromatography, recrystallization and the like as necessary to give the object compound. In this step, when one or more of the protecting groups $R^a$, $R^b$ and $R^c$ of the compound are eliminated, the compound can be re-protected or have a different protecting group, using a suitable reagent after completion of the reaction. In this step, when the other leaving group $X^c$ in compound (III-3) is unstable or capable of reacting together with $X^b$, $X^c$ can be converted in advance to a different protected substituent. For example, when $X^c$ is trifluoromethanesulfonyloxy, $X^c$ is converted in advance to a phenolic hydroxyl group protected by a general protecting group in this step, and after this step, it is converted to trifluoromethanesulfonyloxy by deprotection. This step can also be performed using compounds wherein the activated group $Y^a$ of compound (III-2) and the leaving group $X^b$ of compound (III-3) are exchanged with each other, depending on the stability of the compound, some reason of the starting material, and the like. In this step, biaryl compound (III-6) can be obtained without the next third step, by condensing the compound $X^b$—$Ar_1$—$X$—$Ar_2$ having the leaving group $X^b$, wherein $Ar_1$, $Ar_2$, X and $X^b$ are as defined above, instead of compound (III-3), and intermediate (III-2), in the same manner as in this step.

The third step is a step of condensing intermediate (III-4) having the leaving group $X^c$ with compound (III-5) to give a protected form (III-6) of the compound of the present invention (I-1). The conditions of this step are appropriately selected depending on the kind of X. For example, when X is a sulfur atom, an oxygen atom, or a nitrogen atom optionally substituted by alkyl, the reaction can be carried out in an ether solvent such as 1,4-dioxane, tetrahydrofuran and the like, a hydrocarbon solvent such as toluene and the like, or a polar solvent such as 2-propanol and the like, using a base such as potassium carbonate, diisopropylethylamine and the like, and a catalyst such as palladium (e.g., tris(dibenzylideneacetone) dipalladium (0) and the like) and copper (e.g., copper iodide and the like), and adding, where necessary, a reaction aid, for example, a phosphine compound such as 4,5-bis(diphenylphosphino)-9,9-dimethylxanthene and the like, a diol such as salicylaldoxime and the like, a diamine such as N,N'-dimethylethylenediamine and the like, or the like. The reaction is carried out at 40° C. to under refluxing for about 30 min to 24 hr. The compound wherein X is carbonyl can be synthesized by activating the XH moiety of compound (III-5) as a hydrazone, condensing the resulting compound under the above-mentioned reaction conditions, and subjecting the resulting compound to hydrolysis with an acid; or reacting a compound having, as the XH moiety, an activated group same as $Y^a$, with intermediate (III-4), simultaneously introducing carbonyl using carbon monoxide. After the reaction, the reaction mixture is subjected to extraction, washing, drying, solvent evaporation and the like according to a conventional method, and purified by silica gel column chromatography, recrystallization and the like as necessary to give the object compound.

The fourth step is a step of deprotecting intermediate (III-6) to give the compound of the present invention (1-1). The deprotection of $R^a$, $R^b$ and, when $R_8$ has protected hydroxyl group(s), the protecting group $R^c$ ($R^c$ is as defined above) for protection thereof, is not particularly limited as long as it is generally employed for the removal of protecting groups. All protecting groups can be removed at once or stepwise. For example, when $R^a$ is bonded to $R^c$ to form a cyclic acetal, and $R^b$ is t-butoxycarbonyl, they can be simultaneously removed by an acid. Examples of the acid include inorganic acids such as hydrochloric acid and the like, trifluoroacetic acid and the like. The reaction can be carried out in an alcohol solvent such as ethanol and the like, an ether solvent such as tetrahydrofuran and the like, water, or a mixed solvent thereof, under ice-cooling to 80° C. for about 5 min to 3 hr. After the reaction, the reaction mixture is subjected to extraction, washing, drying, solvent evaporation and the like according to a conventional method, and purified by silica gel column chromatography, recrystallization and the like as necessary to give the object compound.

2) Compound (I-2), which is the compound of the present invention wherein, in the formula (I), $R_1$ is P(=O)(OH)$_2$, is synthesized according to the following scheme (IV).

Scheme (IV)

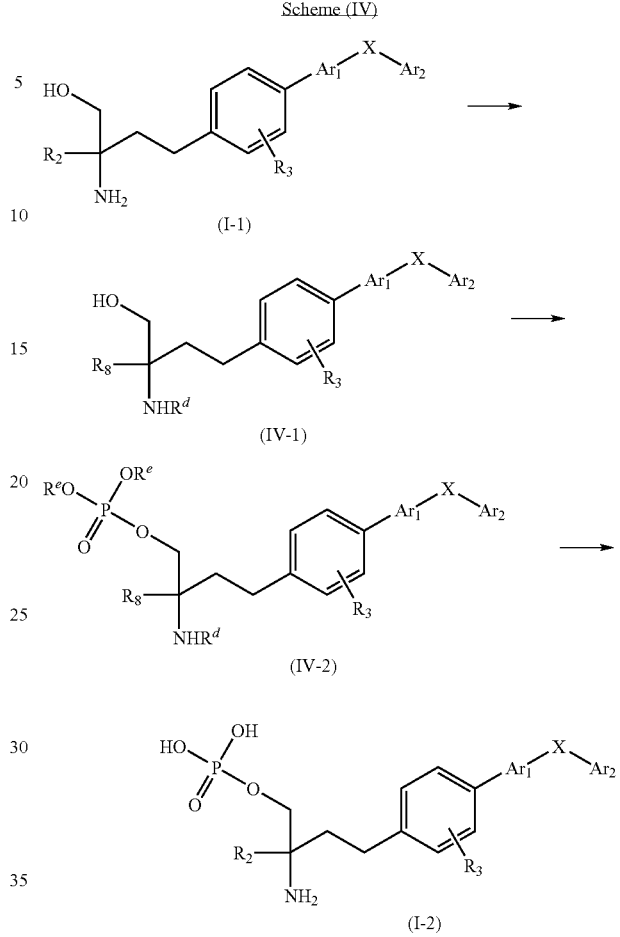

wherein $R^d$ and $R^e$ are each a protecting group, and the other symbols are as defined above.

The protecting group for $R^d$ is not particularly limited as long as it is a group capable of protecting an amino group. Examples thereof include an acyl (preferably an acyl having about 2 to 4 carbon atoms, specifically acetyl and the like), a carbamate (specifically t-butoxycarbonyl and benzyloxycarbonyl) and the like. When $R_2$ of compound (I-1) has hydroxyl group(s), the hydroxyl group can also be protected by the protecting group $R^c$ ($R^c$ is as defined above). When $R_2$ is hydroxymethyl or hydroxyethyl, the amino group and the hydroxyl group contained in $R_2$ can also be protected simultaneously by the formation of the following cyclic compound (IV-1a, IV-1b)

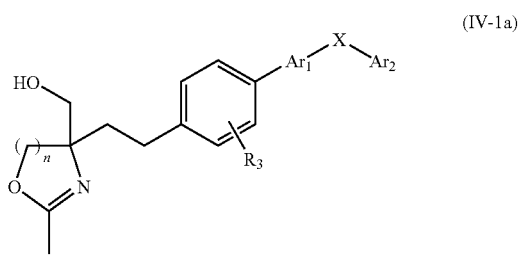

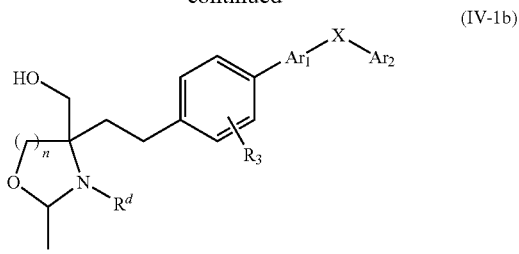

(IV-1b)

wherein n is 1 or 2, and the other symbols are as defined in scheme (IV). The protecting group for $R^e$ is not particularly limited as long as it is a group capable of protecting a phosphate group. Examples thereof include alkyl (preferably an alkyl having about 1 to 6 carbon atoms, specifically t-butyl and the like), benzyl, phenyl and the like.

The first step is a step of protecting the amino group of compound (I-1) obtained in the above-mentioned scheme (III), which is the compound of the present invention wherein $R_1$ is a hydrogen atom to give amino group-protected form (IV-1). This step can be performed using a general reaction for an amino group protection. Specifically, when the protecting group ($R^d$) is an acyl, an alkyloxycarbonyl, benzyloxycarbonyl or the like, this step can be performed in an alcohol such as methanol and the like, or in a two-layer or mixed solvent such as water and an organic solvent such as ethyl acetate, chloroform and the like. Examples of the reagent to be used include acid chlorides such as acetyl chloride, benzyloxycarbonyl chloride and the like, acid anhydrides such as acetic anhydride, di-t-butyl-dicarbonate and the like. In this reaction, an organic base such as triethylamine and the like or an inorganic base such as sodium bicarbonate and the like can be added as a reaction promoter. The reaction is carried out under ice-cooling to 50° C. for about 30 min to 24 hr. After the reaction, the reaction mixture is subjected to extraction, washing, drying, solvent evaporation and the like according to a conventional method, and purified by silica gel column chromatography, recrystallization and the like as necessary to give the object compound. When the amino group and the hydroxyl group contained in $R_2$ are protected simultaneously as an oxazoline represented by the formula (IV-1a), the reaction can be carried out in a polar solvent such as acetonitrile, N,N-dimethylformamide and the like, a halogen solvent such as methylene chloride and the like, or a hydrocarbon solvent such as toluene and the like, using an orthoacetate ester such as triethyl orthoacetate and the like as a reagent. In addition, for the purpose of promoting the reaction, a base such as diisopropylethylamine and the like, or an acid such as p-toluenesulfonic acid and the like can also be added. The reaction is carried out at room temperature to under reflux for about 30 min to 12 hr. After the reaction, the reaction mixture is subjected to extraction, washing, drying, solvent evaporation and the like according to a conventional method, and purified by silica gel column chromatography, recrystallization and the like as necessary to give the object compound.

The second step is a step of reacting amino group-protected form (IV-1) with a phosphorylation reagent (e.g., a phosphoric chloride, a combination of a phosphoramidite and an oxidant, tetrabenzyl pyrophosphate and the like) to give phosphate (IV-2). When the tetrabenzyl pyrophosphate ester is used as a phosphorylation reagent, this step can be performed under non-aqueous conditions, preferably in an organic solvent such as toluene, dichloromethane, a mixed solvent thereof and the like, using an additive (e.g., silver oxide, tetra-n-hexylammonium iodide and the like). The reaction is carried out under ice-cooling to 50° C. for about 5 hr to 24 hr. After the reaction, the reaction mixture is subjected to extraction, washing, drying, solvent evaporation and the like according to a conventional method, and purified by silica gel column chromatography, recrystallization and the like as necessary to give the object compound. Alternatively, this reaction can also be carried out using a general phosphorylation reagent such as a combination of a phosphoric chloride and a base, a combination of a phosphoramidite and an oxidant, and the like. For example, when a combination of a phosphoramidite and an oxidant is used, the reaction can be carried out in a halogen solvent such as dichloromethane and the like, an ether solvent such as tetrahydrofuran and the like, a polar solvent such as acetonitrile and the like, or a mixed solvent thereof, using a phosphoramidite such as di-tert-butyl diisopropylphosphoramidite and the like, under ice-cooling to 50° C. for about 10 min to 5 hr. In this reaction, a reaction promoter such as 1H-tetrazole and the like can be added. In the oxidization reaction of phosphorus following the phosphorylation, an organic peroxide such as m-chloroperbenzoic acid, tert-butylhydroperoxide and the like, or an inorganic peroxide such as hydrogen peroxide and the like can be used. The reaction is carried out under ice-cooling to 50° C. for about 1 min to 1 hr. After the reaction, the reaction mixture is subjected to extraction, washing, drying, solvent evaporation and the like according to a conventional method, and purified by silica gel column chromatography, recrystallization and the like as necessary to give the object compound.

The third step is a step of preparing the compound of the present invention (1-2) from phosphate ester (IV-2). This step is performed using general deprotection, specifically hydrogenolysis, an acid such as hydrochloric acid, trifluoroacetic acid and the like, a Lewis acid such as trimethylsilyl bromide and the like. When hydrogenolysis is used for this reaction, this step can be performed in an alcoholic solvent such as methanol and the like, using a catalyst such as palladium carbon and the like, under a hydrogen atmosphere. The reaction is carried out at room temperature to 60° C. for about 1 to 24 hr. The reaction mixture is subjected to filtration, concentration and the like according to a conventional method, and purified by silica gel column chromatography, recrystallization and the like as necessary to give the object compound. When an acid such as hydrochloric acid and the like is used for this reaction, the reaction is carried out in an alcoholic solvent such as ethanol and the like or in a mixed solvent of water and these solvents, at room temperature to 100° C. for about 30 min to 12 hr. After the reaction, the reaction mixture is poured into water, and the precipitated object compound is collected by filtration; or subjected to extraction, washing, drying, solvent evaporation and the like, and purified by silica gel chromatography, crystallization and the like as necessary to give the object compound.

3) Compound (1-3), which is the compound of the present invention wherein, in the formula (I), $R_1$ is $P(=O)(OH)_2$ and X is a sulfur atom, is also synthesized according to the following scheme (V).

Scheme V

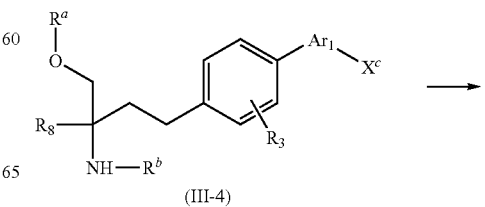

(III-4)

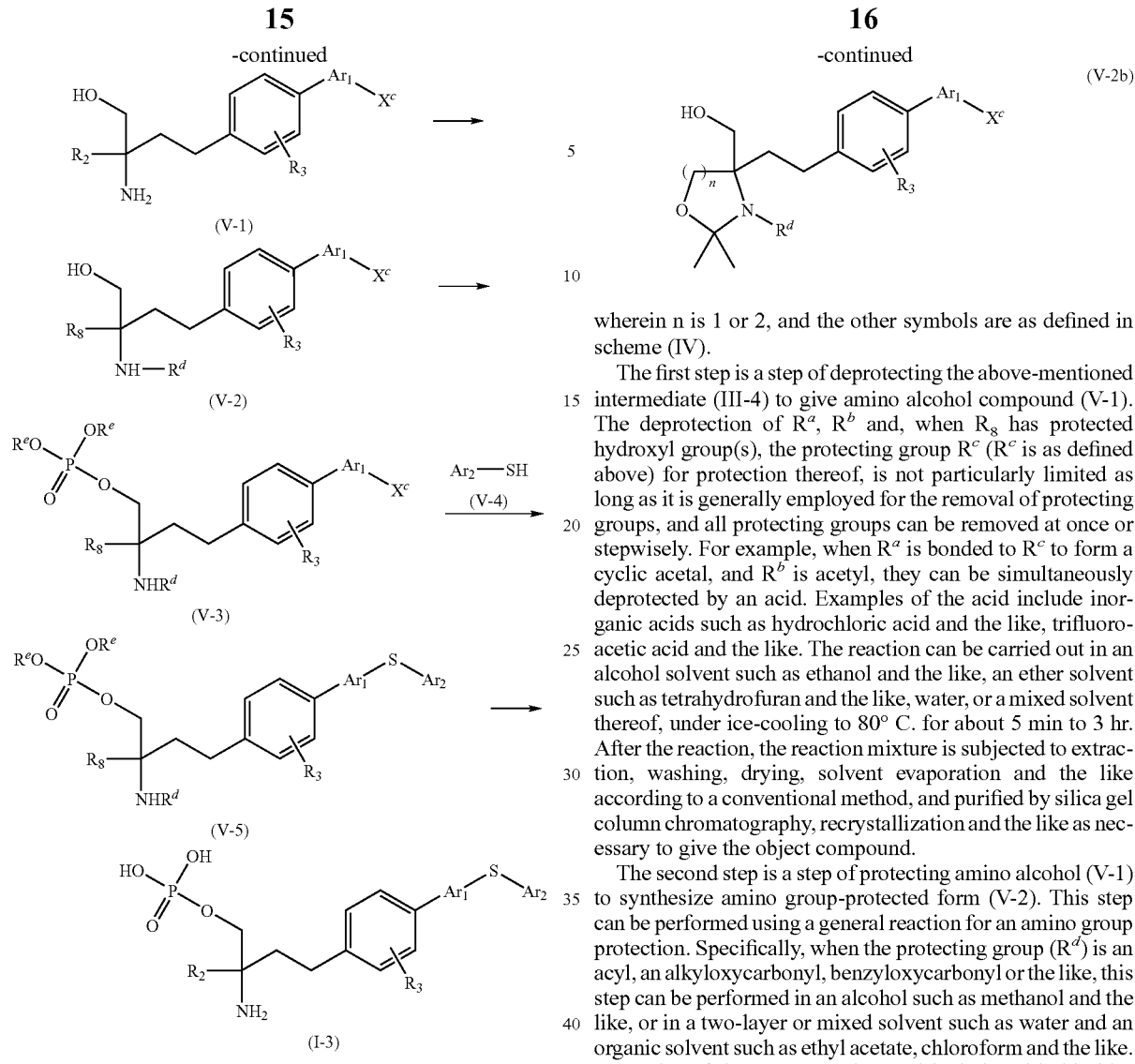

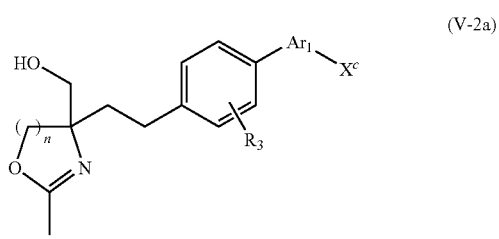

wherein n is 1 or 2, and the other symbols are as defined in scheme (IV).

The first step is a step of deprotecting the above-mentioned intermediate (III-4) to give amino alcohol compound (V-1). The deprotection of $R^a$, $R^b$ and, when $R_8$ has protected hydroxyl group(s), the protecting group $R^c$ ($R^c$ is as defined above) for protection thereof, is not particularly limited as long as it is generally employed for the removal of protecting groups, and all protecting groups can be removed at once or stepwisely. For example, when $R^a$ is bonded to $R^c$ to form a cyclic acetal, and $R^b$ is acetyl, they can be simultaneously deprotected by an acid. Examples of the acid include inorganic acids such as hydrochloric acid and the like, trifluoroacetic acid and the like. The reaction can be carried out in an alcohol solvent such as ethanol and the like, an ether solvent such as tetrahydrofuran and the like, water, or a mixed solvent thereof, under ice-cooling to 80° C. for about 5 min to 3 hr. After the reaction, the reaction mixture is subjected to extraction, washing, drying, solvent evaporation and the like according to a conventional method, and purified by silica gel column chromatography, recrystallization and the like as necessary to give the object compound.

The second step is a step of protecting amino alcohol (V-1) to synthesize amino group-protected form (V-2). This step can be performed using a general reaction for an amino group protection. Specifically, when the protecting group ($R^d$) is an acyl, an alkyloxycarbonyl, benzyloxycarbonyl or the like, this step can be performed in an alcohol such as methanol and the like, or in a two-layer or mixed solvent such as water and an organic solvent such as ethyl acetate, chloroform and the like. Examples of the reagent to be used include acid chlorides such as acetyl chloride, benzyloxycarbonyl chloride and the like, acid anhydrides such as acetic anhydride, di-t-butyldicarbonate and the like. In this reaction, an organic base such as triethylamine and the like or an inorganic base such as sodium bicarbonate and the like can be added as a reaction promoter. The reaction is carried out under ice-cooling to 50° C. for about 30 min to 24 hr. After the reaction, the reaction mixture is subjected to extraction, washing, drying, solvent evaporation and the like according to a conventional method, and purified by silica gel column chromatography, recrystallization and the like as necessary to give the object compound. When the amino group and the hydroxyl group contained in $R_2$ are protected simultaneously as an oxazoline represented by the formula (V-2a), the reaction can be carried out in a polar solvent such as acetonitrile, N,N-dimethylformamide and the like, a halogen solvent such as methylene chloride and the like, or a hydrocarbon solvent such as toluene and the like, using an orthoacetate ester such as triethyl orthoacetate and the like as a reagent. In addition, for the purpose of promoting the reaction, a base such as diisopropylethylamine and the like, or an acid such as p-toluenesulfonic acid and the like can also be added. The reaction is carried out at room temperature to under reflux for about 30 min to 12 hr. After the reaction, the reaction mixture is subjected to extraction, washing, drying, solvent evaporation and the like according to a conventional method, and purified by silica gel column chromatography, recrystallization and the like as necessary to give the object compound.

The third step is a step of reacting amino group-protected form (V-2) with a phosphorylation reagent (e.g., a phosphoric chloride, a combination of a phosphoramidite and an oxidant, tetrabenzyl pyrophosphate and the like) to give phosphate ester (V-3). When the tetrabenzyl pyrophosphate is used as a phosphorylation reagent, this step can be performed under non-aqueous conditions, preferably in an organic solvent such as toluene, dichloromethane, a mixed solvent thereof and the like, using an additive (e.g., silver oxide, tetra-n-hexylammonium iodide and the like). The reaction is carried out under ice-cooling to 50° C. for about 5 hr to 24 hr. After the reaction, the reaction mixture is subjected to extraction, washing, drying, solvent evaporation and the like according to a conventional method, and purified by silica gel column chromatography, recrystallization and the like as necessary to give the object compound. Alternatively, this reaction can also be carried out using a general phosphorylation reagent such as a combination of a phosphoric chloride and a base, a combination of a phosphoramidite and an oxidant, and the like. For example, when a combination of a phosphoramidite and an oxidant is used, the reaction can be carried out in a halogen solvent such as dichloromethane and the like, an ether solvent tetrahydrofuran and the like, a polar solvent such as acetonitrile and the like, or a mixed solvent thereof, using a phosphoramidite such as di-tert-butyl diisopropylphosphoramidite and the like, under ice-cooling to 50° C. for about 10 min to 5 hr. In this reaction, a reaction promoter such as 1H-tetrazole and the like can be added. In the oxidization reaction of phosphorus followed by the phosphorylation, an organic peroxide such as m-chloroperbenzoic acid, tert-butylhydroperoxide and the like, or an inorganic peroxide such as hydrogen peroxide and the like can be used. The reaction is carried out under ice-cooling to 50° C. for about 1 min to 1 hr. After the reaction, the reaction mixture is subjected to extraction, washing, drying, solvent evaporation and the like according to a conventional method, and purified by silica gel column chromatography, recrystallization and the like as necessary to give the object compound.

The fourth step is step of condensing intermediate (V-3) having a leaving group $X^c$ with thiol (V-4) to give biaryl sulfide (V-5). This reaction can be carried out in a hydrocarbon solvent such as toluene and the like, a ether solvent such as 1,2-dimethoxyethane, 1,4-dioxane and the like, a polar solvent such as N,N-dimethylacetamide and the like, or in a mixed solvent thereof, using, as a catalyst, a palladium compound tris(dibenzylideneacetone)dipalladium (0), palladium acetate (II), dichloro(di-tert-butyl-phosphenic acid)palladium(II) and the like, at room temperature to under reflux for about 1 to 48 hr. In this reaction, an inorganic base such as potassium carbonate, sodium carbonate and the like, an organic base such as sodium tert-butoxide, potassium tert-butoxide, diisopropylethylamine and the like can be added. In addition, as a reaction promoter, a phosphine compound such as 4,5-bis(diphenylphosphino)-9,9-dimethylxanthene, bis[2-(diphenylphosphino)phenyl]ether, 1,1'-bis(di-tert-butylphosphino)ferrocene and the like, and the like can also be added. Moreover, by adding an additive such as cesium fluoride and the like, compound (V-4) can be used as it is, even if the thiol group thereof is protected by a silyl group such as triisopropylsilyl and the like. After the reaction, the reaction mixture is cooled or poured into water, and the precipitated object compound is collected by filtration; or is subjected to extraction, washing, drying, solvent evaporation and the like according to a conventional method, and purified by silica gel chromatography, crystallization and the like as necessary to give the object compound.

The fifth step is a step of preparing the compound of the present invention (1-3) from phosphate ester (V-5). This step is performed using general deprotection, specifically hydrogenolysis, an acid such as hydrochloric acid, trifluoroacetic acid and the like, a Lewis acid such as trimethylsilyl bromide and the like. When hydrogenolysis is used for this reaction, this step can be performed in an alcoholic solvent such as methanol and the like, using a catalyst such as palladium carbon and the like, under a hydrogen atmosphere. The reaction is carried out at room temperature to 60° C. for about 1 to 24 hr. The reaction mixture is subjected to filtration, concentration and the like according to a conventional method, and purified by silica gel column chromatography, recrystallization and the like as necessary to give the object compound. When an acid such as hydrochloric acid and the like is used for this reaction, the reaction is carried out in an alcoholic solvent such as ethanol and the like or in a mixed solvent of water and these solvents, at room temperature to 100° C. for about 30 min to 12 hr. After the reaction, the reaction mixture is poured into water, and the precipitated object compound is collected by filtration; or subjected to extraction, washing, drying, solvent evaporation and the like, and purified by silica gel chromatography, crystallization and the like as necessary to give the object compound.

The production method of the compound of the present invention can be widely used for, besides the production of the compound of the present invention, the production of a diphenyl sulfide or a phenyl thienyl sulfide, which has an aminobutanol backbone as a partial structure in a substituent. Specifically the diphenyl sulfide or phenyl thienyl sulfide can be obtained by the condensation reaction of a benzene compound having the leaving group $X^c$, which is represented by the formula (II-1), with a benzenethiol represented by the formula (II-2), as shown in scheme (VI); or the condensation reaction of a thiol compound represented by the formula (II-1') with a benzene compound having the leaving group $X^c$ which is represented by the formula (II-2'), as shown in scheme (VI').

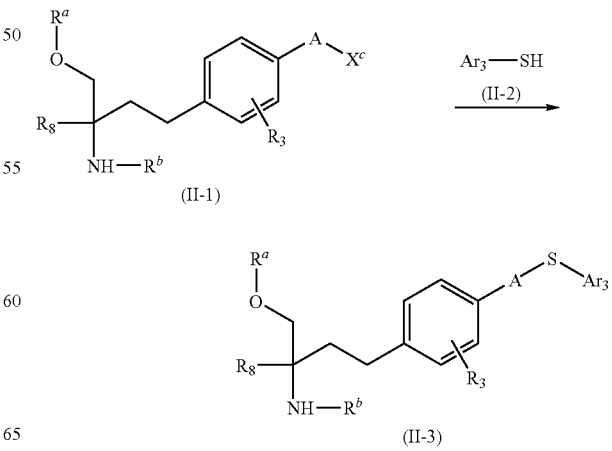

Scheme (VI')

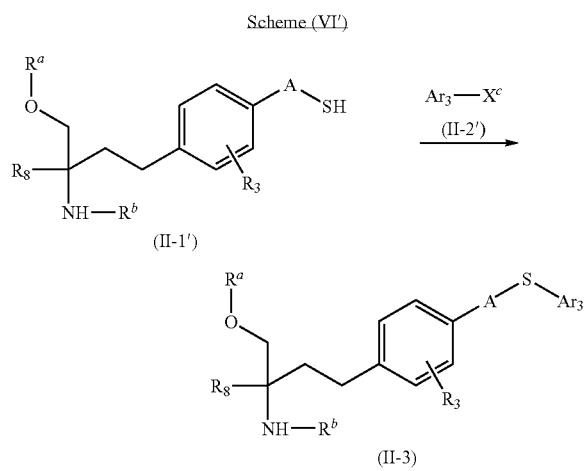

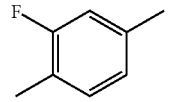

wherein, in schemes (VI) and (VI'), $R_8$ is an alkyl having 1 to 4 carbon atoms optionally substituted by hydroxyl group(s) optionally protected or optionally substituted by halogen atom(s), $R_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s), $Ar_3$ is an optionally substituted aryl, an optionally substituted heteroaryl, a phenyl substituted by hydroxyl group(s) optionally protected, or benzyloxyphenyl, A is an optionally substituted arylene, an optionally substituted heteroarylene or a single bond, $R^a$ and $R^b$ are each a hydrogen atom or a protecting group, and $X^c$ is a leaving group.

Specific examples of $R^a$, $R^b$ and $X^c$ include those similar to the groups exemplified in scheme (III). Examples of the protecting group $R^c$ of optionally protected hydroxyl for $R_8$ include those similar to the groups exemplified for $R^a$. In addition, $R^c$ is optionally bonded to $R^a$ to form a cyclic acetal. Specific examples of the optionally substituted arylene and optionally substituted heteroarylene for A include those similar to the groups exemplified for $Ar_1$. Specific examples of the optionally substituted aryl and optionally substituted heteroaryl for $Ar_3$ include those similar to the groups exemplified for $Ar_2$. The hydroxyl-protecting group of the "phenyl substituted by hydroxyl group(s) optionally protected" for $Ar_3$ is not particularly limited as long as it is not eliminated during the reaction, and examples thereof include protecting groups capable of forming an acetal, such as methoxymethyl, benzyloxymethyl, tetrahydropyranyl and the like, silyl ethers such as trimethylsilyl and the like, ethers such as methyl and the like, acyls such as acetyl, methoxycarbonyl and the like, and the like. In the above-mentioned formulas (II-1), (II-2), (II-3), (II-1') and (II-2'), $R_8$ is preferably hydroxymethyl wherein the hydroxyl group is optionally protected, more preferably acetoxymethyl. $R_3$ is preferably a hydrogen atom. $Ar_3$ is preferably an optionally substituted aryl, more preferably methylphenyl. A is preferably an optionally substituted arylene, more preferably wherein the bond at the ortho-position of the fluorine atom is bonded to the benzene ring, and the bond at the meta-position is bonded to the sulfur atom. Preferably, $R^a$ and $R^b$ are each acetyl, or $R^a$ is bonded to the hydroxyl-protecting group $R^c$ contained in $R_8$ to form a cyclic acetal, and $R^b$ is tert-butoxycarbonyl.

The starting material compound (II-1) can be synthesized according to a known method (e.g., WO03/029184) using a malonic acid derivative, a known method (e.g., Organic Letters, vol. 5, 2003, pages 4017-4020) using an acetylene compound, or a known method (e.g., WO03/099192) using a Wittig reaction. The catalyst used for this reaction is mainly a copper compound or a palladium compound.

When a copper compound is used as a catalyst, this reaction can be carried out in an alcohol solvent such as 2-propanol and the like, a polar solvent such as N,N-dimethylformamide, water and the like, an ether solvent such as 1,4-dioxane, 1,2-dimethoxyethane and the like, or in a mixed solvent thereof, using, as a catalyst, copper powder, a monovalent copper such as copper(I) iodide, copper(I) bromide and the like, or a divalent copper such as copper(II) bromide and the like, at room temperature to under reflux for about 1 to 48 hr. In this reaction, an inorganic base such as potassium carbonate, tripotassium phosphate, sodium hydroxide and the like, or an organic base such as triethylamine, 1,8-diazabicyclo[5.4.0]undec-7-ene and the like can be added. Moreover, a reaction promoter such as ethylene glycol and the like can also be added. After the reaction, the reaction mixture is cooled or poured into water, and the precipitated object compound is collected by filtration; or subjected to extraction, washing, drying, solvent evaporation and the like according to a conventional method, and purified by silica gel chromatography, recrystallization and the like as necessary to give the object compound.

When a palladium compound is used as a catalyst, this reaction can be carried out in a hydrocarbon solvent such as toluene and the like, an ether solvent such as 1,2-dimethoxyethane, 1,4-dioxane and the like, a polar solvent such as N,N-dimethylacetamide and the like, or in a mixed solvent thereof, using, as a catalyst, a palladium compound tris(dibenzylideneacetone)dipalladium (0), palladium acetate (II), dichloro(di-tert-butyl-phosphenic acid)palladium (II) and the like, at room temperature to under reflux for about 1-48 hr. In this reaction, an inorganic base such as potassium carbonate, sodium carbonate and the like, an organic base such as sodium tert-butoxide, potassium tert-butoxide, diisopropylethylamine and the like can be added. In addition, as a reaction promoter, a phosphine compound such as 4,5-bis(diphenylphosphino)-9,9-dimethylxanthene, bis[2-(diphenylphosphino)phenyl]ether, 1,1'-bis(di-tert-butylphosphino)ferrocene and the like, and the like can also be added. Moreover, by adding an additive such as cesium fluoride and the like, benzenthiol represented by the formula (II-2) can be used as it is, even if the thiol group thereof is protected by a silyl group such as triisopropylsilyl and the like. After the reaction, the reaction mixture is cooled or poured into water, and the precipitated object compound is collected by filtration; or is subjected to extraction, washing, drying, solvent evaporation and the like according to a conventional method, and purified by silica gel chromatography, recrystallization and the like as necessary to give the object compound.

By removing the protecting group ($R^a$, $R^b$ or $R^c$ when the protected hydroxyl group is contained in $R_8$), diphenyl sulfide or phenyl thienyl sulfide (II-3) having an aminoethanol structure, which is obtained by this production method, is converted to a compound having an immunosuppressive action, such as the compound of the present invention wherein X=S, which is represented by the below-mentioned formula (II-4), 2-amino-2-{2-[4-(3-benzyloxyphenylthio)-2-chlorophenyl]ethyl}propane-1,3-diol hydrochloride (KRP-203) reported in Circulation, vol. 111, 2005, pages 222-229, and the like. In addition, when $Ar_3$ is a phenyl substituted by hydroxyl group(s) or protected hydroxyl group(s), prior to the removal of the protecting group $R^a$, $R^b$ and $R^c$, the hydroxyl group or the hydroxyl group generated by deprotection of the protecting group for $Ar_3$ can be converted to a desired substituent.

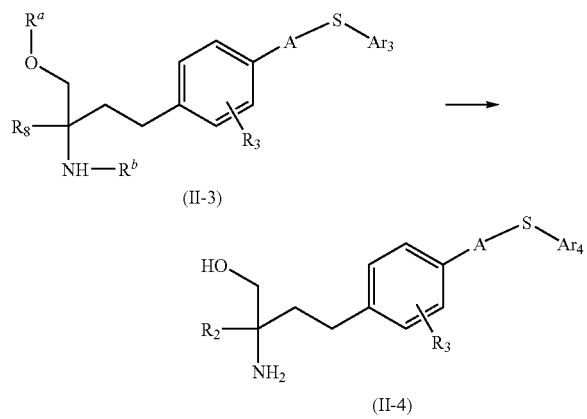

wherein
$R_8$, $R_3$, $Ar_3$, $R^a$, $R^b$ and $X^c$ are as defined above,
$R_2$ is an alkyl having 1 to 4 carbon atoms optionally substituted by hydroxyl group(s) or optionally substituted by halogen atom(s), and
$Ar_4$ is an optionally substituted aryl, an optionally substituted heteroaryl, a phenyl substituted by hydroxyl group(s), or benzyloxypheny.

In the above-mentioned formula (II-4), $R_2$ is preferably hydroxymethyl. $R_3$ is preferably a hydrogen atom. $Ar_4$ is preferably an optionally substituted aryl, more preferably methylphenyl. A is preferably an optionally substituted arylene, more preferably

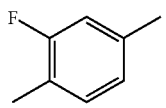

wherein the bond at the ortho-position of the fluorine atom is bonded to the benzene ring, and the bond at the meta-position is bonded to the sulfur atom.

The compound of the present invention can be converted to an acid addition salt by treating with an acid in a suitable solvent (water, alcohol, ether and the like) as necessary. In addition, the obtained compound of the present invention can be converted to a hydrate or a solvate by treating with water, an aqueous solvent or other solvent (for example, alcohol etc.).

The compound of the present invention is useful for the treatment or prophylaxis of autoimmune diseases (e.g., rheumatoid arthritis, multiple sclerosis, encephalomyelitis, systemic lupus erythematosus, lupus nephritis, nephrosis syndrome, psoriasis, Type I diabetes mellitus etc.); prophylaxis or prevention of acute rejection or chronic rejection in transplantation of organs or tissues (e.g., including transplantation or heterologous transplantation of heart, kidney, liver, lung, bone marrow, cornea, pancreas, small intestine, extremity, muscle, nerve, duodenum, skin, pancreatic islet cell and the like) of mammals such as human, dog, cat, bovine, horse, swine, monkey, mouse and the like; or the treatment or prophylaxis of graft vs host (GvH) disease due to bone marrow transplantation; allergic diseases (e.g., atopic dermatitis, allergic rhinitis, asthma etc.).

In the present invention, "prophylaxis" means an act of administration of the compound of the present invention or a pharmaceutical composition containing the compound to an individual who has not developed a disease, condition or symptom. In addition, the "treatment" means an act of administration of the compound of the present invention or a pharmaceutical composition containing the compound to an individual who has already developed a disease, condition or symptom. Accordingly, the act of administration to an individual who has already developed a disease, condition or symptom, for the purpose of preventing the aggravation, attack or recurrence of symptoms and the like is one embodiment of the "treatment".

When the compound of the present invention is used as a pharmaceutical agent, it can be administered orally or parenterally in the form of a pharmaceutical composition or preparation (oral preparation, injection and the like) obtained by mixing the compound of the present invention and a pharmaceutically acceptable carrier (excipient, binder, disintegrant, corrigent, flavor, emulsifier, diluent, solubilizing agents and the like). The pharmaceutical composition can be formulated according to a general method.

In the present specification, parenteral includes subcutaneous injection, intravenous injection, intramuscular injection, intraperitoneal injection, intravenous method or topical administration (transdermal administration, transocular administration, pulmonary or intrabronchial administration, transnasal administration or intrarectal administration and the like) and the like.

The content of the compound of the present invention that can be combined with a carrier can be changed depending on the host to be treated and particular administration mode. Note that the particular dose of particular patients is determined depending on various factors including age, body weight, general health condition, sex, diet, administration time, administration method, clearance rate and severity of particular disease under treatment.

The dose of the compound of the present invention is determined in consideration of the age, body weight, general health condition, sex, diet, administration time, administration method, clearance rate and severity of the condition under treatment and other factors. The compound of the present invention is free of an influence on the heart rate and can be safely used. The daily dose varies depending on the condition and body weight of patients, kind of the compound, administration route and the like. For example, it is administered at about 0.01-50 mg/patient/day parenterally (subcutaneously, intravenously, intramuscularly, transdermally, transocularly, pulmonarily or intrabronchially, transnasally or intrarectally) or about 0.01-150 mg/patient/day orally.

EXAMPLES

The present invention is explained in more detail in the following by referring to Examples, which are not to be construed in any way as limitative.

Reference Example 1

Trifluoromethanesulfonic acid 5-benzyloxynaphthalen-1-yl ester

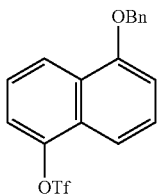

1-Benzyloxy-5-hydroxynaphthalene (2.2 g) was dissolved in dichloromethane (75 mL), pyridine (1.1 mL) was added, and trifluoromethanesulfonic anhydride (1.8 mL) diluted with dichloromethane (15 mL) was slowly added dropwise thereto at 0° C. After stirring at the same temperature for 1 hr, aqueous sodium hydrogen carbonate was added to the reaction mixture. The mixture was extracted with dichloromethane, washed with saturated brine, and dried over anhydrous sodium sulfate. The solvent was evaporated under reduced pressure and the residue was purified by silica gel column chromatography (hexane:ethyl acetate=10:1), and the resulting crystals were washed with hexane to give the object product (2.3 g) as pale-yellow crystals.

$^1$H-NMR(DMSO-$d_6$)δ(ppm): 5.37(2H, s), 7.28-7.73(10H, m), 8.34(1H, d, J=8.2 Hz).

Reference Example 2

2-(4-bromophenyl)ethyl iodide

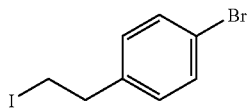

To a solution of 2-(4-bromophenyl)ethanol (75.0 g) and triethylamine (45.3 g) in methylene chloride (400 mL) was added dropwise methanesulfonyl chloride (47.0 g) at 0° C. over 1 hr, and the mixture was stirred at the same temperature for 3 hr. The reaction mixture was poured into ice water, and the organic layer was washed with saturated brine and dried over anhydrous sodium sulfate. The solvent was evaporated under reduced pressure. To a solution of the residue in methyl ethyl ketone (500 mL) was added sodium iodide (67.1 g), and the mixture was stirred at 90° C. for 3 hr. The reaction mixture was concentrated under reduced pressure, and water (500 mL) was added to the residue. After extraction with ethyl acetate, the mixture was washed with 1% aqueous sodium thiosulfate solution and saturated brine, and dried over anhydrous sodium sulfate.

The solvent was evaporated under reduced pressure to give the title compound (116 g) as brown crystals.

$^1$H-NMR(CDCl$_3$)δ(ppm): 3.13(2H, t, J=7.7 Hz), 3.32(2H, d, J=7.4 Hz), 7.07(2H, d, J=8.4 Hz), 7.44(2H, d, J=8.1 Hz).

Reference Example 3

Diethyl 2-acetamide-2-[2-(4-bromophenyl)ethyl]malonate

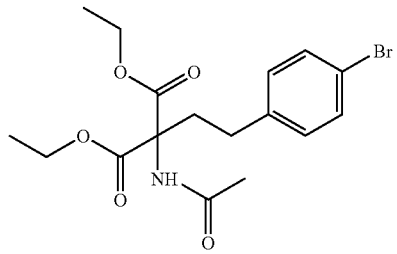

To a solution of diethyl acetamidomalonate (40.0 g) in N,N-dimethylformamide (200 mL) was added sodium hydride (60%, 7.59 g) by portions at 0° C., and the mixture was stirred at the same temperature for 30 min. A solution of 2-(4-bromophenyl)ethyl iodide (58 g) obtained in the same manner as in Reference Example 2 in N,N-dimethylformamide (50 mL) was added to the reaction mixture at 0° C., and the mixture was stirred at the same temperature for 30 min and further stirred at room temperature for 1 hr. The reaction mixture was poured into water. After extraction with ethyl acetate, the extract was washed with water and saturated brine, and dried over anhydrous sodium sulfate. The solvent was evaporated under reduced pressure, and the precipitated crystals were suspended in a mixed solution of diisopropyl ether (50 mL) and hexane (100 mL) and collected by filtration to give the title compound (46.8 g) as white crystals.

$^1$H-NMR(CDCl$_3$)δ(ppm): 1.25(6H, t, J=7.2 Hz), 1.99(3H, s), 2.41-2.46(2H, m), 2.64-2.69(2H, m), 4.16-4.29(4H, m), 6.75(1H, s), 7.02(2H, d, J=8.4 Hz), 7.38(2H, d, J=8.1 Hz).

Reference Example 4

N-[3-(4-bromophenyl)-1,1-bis(hydroxymethyl)propyl]acetamide

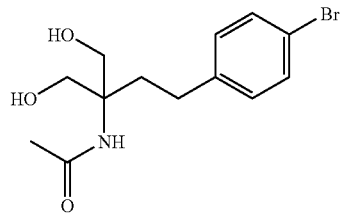

To a mixed solution of a solution of diethyl 2-acetamide-2-[2-(4-bromophenyl)ethyl]malonate (57.8 g) obtained in the same manner as in Reference Example 3 in ethanol (500 mL) and an aqueous solution (100 mL) of calcium chloride (32.0 g) was added sodium borohydride (21.8 g) by portions at 0° C. over 1.5 hr, and the mixture was stirred at room temperature for 1 hr. 1M Hydrochloric acid (250 mL) was added to the reaction mixture and ethanol was evaporated under reduced pressure, after which 1M hydrochloric acid (250 mL) was further added. After extraction with ethyl acetate (250 mL×2), the extract was washed with 0.5M hydrochloric acid (250 mL) and saturated brine (250 mL), and dried over anhydrous sodium sulfate. The solvent was evaporated under reduced pressure to give the title compound (42.2 g) as white crystals.

$^1$H-NMR(DMSO-d$_6$)δ(ppm): 1.81-1.87(5H, m), 2.45-2.51 (2H, m), 3.46(2H, dd, J=6.9, 11.1 Hz), 3.56(2H, dd, J=5.7, 10.8 Hz), 4.81(2H, t, J=5.7 Hz), 7.14(2H, d, J=8.1 Hz), 7.44 (2H, d, J=8.4 Hz).

Reference Example 5

N-{5-[2-(4-bromophenyl)ethyl]-2,2-dimethyl-1,3-dioxan-5-yl}acetamide

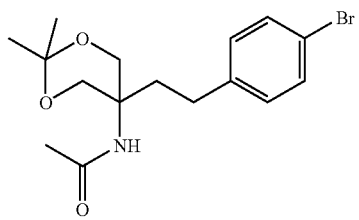

A solution of N-[3-(4-bromophenyl)-1,1-bis(hydroxymethyl)propyl]acetamide (42.2 g) of Reference Example 4, acetone dimethyl acetal (41.9 g) and a catalytic amount of p-toluenesulfonic acid in acetone (200 mL) was stirred at room temperature for one day. The reaction mixture was concentrated under reduced pressure, and the residual crude crystals were suspended in aqueous sodium hydrogen carbonate solution and collected by filtration to give the title compound (41.5 g) as white crystals.

$^1$H-NMR(CDCl$_3$)δ(ppm): 1.43(6H, s), 2.03(3H, s), 2.01-2.06(2H, m), 2.46-2.52(2H, m), 3.67(2H, d, J=11.7 Hz), 3.95 (2H, d, J=11.7 Hz), 5.76(1H, s), 7.05(2H, d, J=8.4 Hz), 7.38 (2H, d, J=8.4 Hz).

Reference Example 6

N-(5-{2-[4-(5,5-dimethyl-1,3,2-dioxaborinan-2-yl) phenyl]ethyl}-2,2-dimethyl-1,3-dioxan-5-yl)acetamide

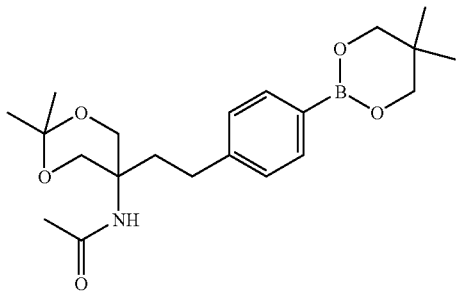

A solution of N-{5-[2-(4-bromophenyl)ethyl]-2,2-dimethyl-1,3-dioxan-5-yl}acetamide (7.13 g) of Reference Example 5, bis(neopentyl glycolato)diboron (4.97 g), potassium acetate (5.89 g) and dichlorobis(tricyclohexylphosphine)palladium (II) (738 mg) in 1,4-dioxane (80 mL) was stirred at 100° C. for 6 hr. Water was added to the reaction mixture, and the mixture was extracted with ethyl acetate. The mixture was washed with water and saturated brine, and dried over anhydrous sodium sulfate. The solvent was evaporated under reduced pressure, and the residual crude crystals were suspended in water and collected by filtration to give the title compound (7.33 g) as brown crystals.

$^1$H-NMR(CDCl$_3$)δ(ppm): 1.01(6H, s), 1.42(6H, s), 2.02 (3H, s), 2.03-2.09(2H, m), 2.53-2.58(2H, m), 3.66(2H, d, J=11.7 Hz), 3.76(4H, s), 3.97(2H, d, J=12.0 Hz), 5.71(1H, s), 7.17(2H, d, J=8.1 Hz), 7.70(2H, d, J=7.8 Hz).

Reference Example 7

N-[1,1-bis(acetoxymethyl)-3-(4-bromophenyl)propyl]acetamide

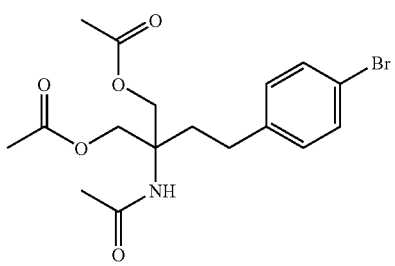

To a solution of N-[3-(4-bromophenyl)-1,1-bis(hydroxymethyl)propyl]acetamide (100 g) obtained in the same manner as in Reference Example 4 in pyridine (100 mL) was added dropwise acetic anhydride (100 mL) at 0° C., and the mixture was stirred at room temperature for one day. Water (1.5 L) was added to the reaction mixture, and the precipitated crystals were collected by filtration to give the title compound (106 g) as white crystals.

$^1$H-NMR(CDCl$_3$)δ(ppm): 1.99(3H, s), 2.10(6H, s), 2.16-2.22(2H, m), 2.53-2.59(2H, m), 4.33(4H, s), 5.73(1H, s), 7.06(2H, d, J=8.1 Hz), 7.39(2H, d, J=8.7 Hz).

Reference Example 8

N-{1,1-bis(acetoxymethyl)-3-[4-(4,4,5,5-tetramethyl-1,3,2-dioxaborolan-2-yl)phenyl] propyl}acetamide

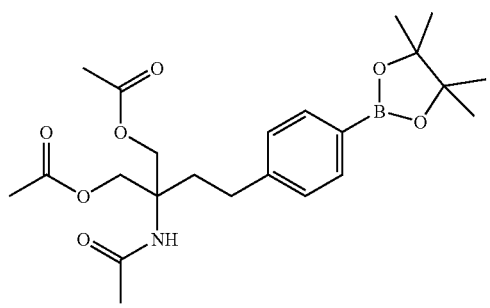

N-[1,1-Bis(acetoxymethyl)-3-(4-bromophenyl)propyl]acetamide (5.00 g) of Reference Example 7 was dissolved in 1,4-dioxane (50 mL), bis(pinacolate)diboron (3.50 g), potassium acetate (3.70 g) and bis(tricyclohexylphosphine)palladium dichloride (0.380 mg) were added, and the mixture was stirred at 100° C. for 4 hr. Water was added to the reaction mixture, and the mixture was extracted with ethyl acetate. The extract was washed with water and saturated brine, and dried over anhydrous sodium sulfate. The solvent was evaporated under reduced pressure and the residue was purified by silica gel column chromatography (hexane:ethyl acetate=1:1), and the resulting crystals were washed with hexane to give the object product (4.5 g) as white crystals.

$^1$H-NMR(DMSO-d$_6$)δ(ppm): 1.28(12H, s), 1.85(3H, s), 1.93-1.97(2H, m), 2.02(6H, s), 2.50-2.56(2H, m), 4.19(2H, d, J=11.0 Hz), 4.28(2H, d, J=11.0 Hz), 7.19(2H, d, J=7.8 Hz), 7.59(2H, d, J=7.8 Hz), 7.68(1H, s).

Reference Example 9

N-{1,1-bis(acetoxymethyl)-3-[4-(5,5-dimethyl-1,3,2-dioxaborinan-2-yl)phenyl]propyl}acetamide

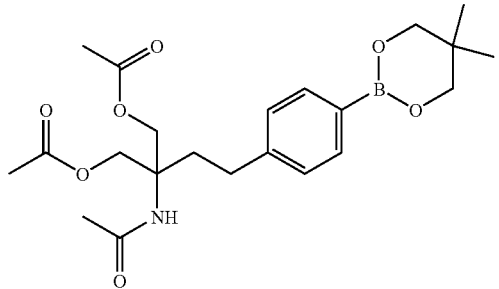

A solution of N-[1,1-bis(acetoxymethyl)-3-(4-bromophenyl)propyl]acetamide (5.00 g) of Reference Example 7, bis(neopentyl glycolato)diboron (3.09 g), potassium acetate (3.68 g) and dichlorobis(tricyclohexylphosphine)palladium (II) (461 mg) in 1,4-dioxane (50 mL) was stirred at 100° C. for 9 hr. The reaction mixture was poured into water. After extraction with ethyl acetate, the extract was washed with water and saturated brine, and dried over anhydrous sodium sulfate. The solvent was evaporated under reduced pressure to give the title compound (5.30 g) as brown crystals.

$^1$H-NMR(CDCl$_3$)δ(ppm): 1.02(6H, s), 1.95(3H, s), 2.09 (6H, s), 2.17-2.23(2H, m), 2.59-2.65(2H, m), 3.76(4H, s), 4.35(4H, m), 5.65(1H, s), 7.18(2H, d, J=7.9 Hz), 7.72(2H, d, J=7.8 Hz).

Reference Example 10

N-{5-[2-(4'-bromo-2'-fluorobiphenyl-4-yl)ethyl]-2,2-dimethyl-1,3-dioxan-5-yl}acetamide

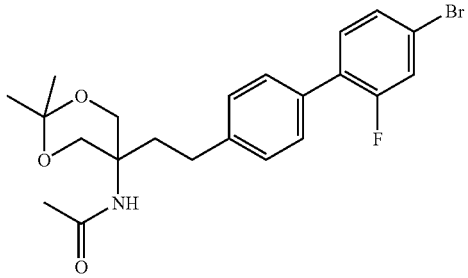

A mixed solution of N-(5-{2-[4-(5,5-dimethyl-1,3,2-dioxaborinan-2-yl)phenyl]ethyl}-2,2-dimethyl-1,3-dioxan-5-yl) acetamide (7.33 g) of Reference Example 6, 1-bromo-3-fluoro-4-iodobenzene (5.95 g), sodium hydrogen carbonate (9.48 g) and tetrakistriphenylphosphine palladium (434 mg) in 1,2-dimethoxyethane (120 mL)-water (40 mL) was heated under reflux for 8 hr. 1-Bromo-3-fluoro-4-iodobenzene (2.83 g) and tetrakistriphenylphosphine palladium (217 mg) were added to the reaction mixture, and the mixture was further stirred at 100° C. for 15 hr. The reaction mixture was extracted with ethyl acetate, washed with saturated brine, and dried over anhydrous sodium sulfate. The solvent was evaporated under reduced pressure and the residue was purified by silica gel column chromatography, and the obtained crude crystals were suspended in diisopropyl ether and collected by filtration to give the title compound (5.28 g) as white crystals.

$^1$H-NMR(DMSO-d$_6$)δ(ppm): 1.35(6H, s), 1.87(3H, s), 1.98-2.04(2H, m), 2.47-2.53(2H, m), 3.71(2H, d, J=11.8 Hz), 3.97(2H, d, J=11.6 Hz), 7.27(2H, d, J=8.1 Hz), 7.44-7.53(3H, m), 7.61-7.66(2H, m).

Reference Example 11

Methyl 4-bromo-2-chlorobenzoate

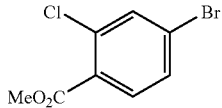

To a solution of 4-bromo-2-chlorobenzoic acid (450 g) in N,N-dimethylformamide (3000 mL) were added potassium carbonate (792.4 g) and iodomethane (271 g) at 10° C., and the mixture was stirred at the same temperature for 2 hr. Iodomethane (54.3 g) was added, and the mixture was stirred at the same temperature for 1 hr. Iodomethane (27.2 g) was added again, and the mixture was stirred at the same temperature for 1 hr. Iodomethane (27.2 g) was further added, and the mixture was stirred at the same temperature for 1 hr. The reaction mixture was poured into water, and partitioned and extracted with ethyl acetate. The organic layer was washed with 25% brine, and dried over anhydrous magnesium sulfate. The solvent was evaporated under reduced pressure to give the title compound (477 g) as a pale-yellow oil.

$^1$H-NMR(CDCl$_3$)δ(ppm): 3.93(3H, s), 7.46(1H, dd, J=1.8, 8.4 Hz), 7.64(1H, d, J=1.8 Hz), 7.72(1H, d, J=8.4 Hz).

Reference Example 12

4-bromo-2-chlorobenzyl alcohol

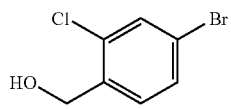

Methyl 4-bromo-2-chlorobenzoate (477 g) of Reference Example 11 was dissolved in a mixed solution of ethanol (3000 mL) and water (680 mL), calcium chloride (212.2 g) was added at 10° C., and the mixture was stirred for 30 min. To the solution was added sodium borohydride (144.7 g) by portions so that the inside temperature would not exceed 25° C., and the mixture was stirred at room temperature for 5 hr. 1M Hydrochloric acid (5100 mL) was added dropwise to the reaction mixture, and the reaction solvent was evaporated under reduced pressure. Water and ethyl acetate were added to the residue. After partitioning and extraction, the organic layer was washed with 25% brine, and dried over anhydrous magnesium sulfate. The solvent was evaporated under reduced pressure to give the title compound (399 g) as white crystals.

$^{1}$H-NMR(CDCl$_{3}$)δ(ppm): 1.87(1H, t, J=5.8 Hz), 4.74(2H, d, J=5.8 Hz), 7.38(1H, d, J=8.2 Hz), 7.42(1H, dd, J=1.8, 8.2 Hz), 7.53(1H, d, J=1.8 Hz).

Reference Example 13

4-bromo-2-chlorobenzyl bromide

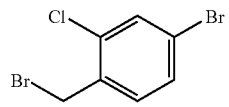

To 4-bromo-2-chlorobenzyl alcohol (399 g) of Reference Example 12 were added toluene (2452 mL) and 48% aqueous hydrogen bromide solution (2453 mL), and the mixture was refluxed with stirring for 2 hr. After cooling, water and ethyl acetate were added to the reaction mixture. After partitioning and extraction, the organic layer was washed with water, 1M aqueous sodium hydroxide solution and 25% brine, and dried over anhydrous magnesium sulfate. The solvent was evaporated under reduced pressure to give the title compound (535 g) as a pale-yellow oil.

$^{1}$H-NMR(CDCl$_{3}$)δ(ppm): 4.53(2H, s), 7.31(1H, d, J=8.2 Hz), 7.39(1H, dd, J=1.8, 8.2 Hz), 7.56(1H, d, J=1.8 Hz).

Reference Example 14

4-bromo-2-chlorobenzyl cyanide

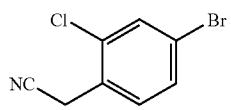

Potassium cyanide (587 g) was dissolved in a mixed solution of water (1408 mL) and dimethyl sulfoxide (767 g), and a solution of 4-bromo-2-chlorobenzyl bromide (512 g) of Reference Example 13 in dimethylsulfoxide (1663 g) was added dropwise at an inside temperature of 90° C. After stirring at the same temperature for 1 hr, the reaction mixture was poured into water. After partitioning and extraction with ethyl acetate, the organic layer was washed 4 times with 25% brine, and dried over anhydrous magnesium sulfate. The solvent was evaporated under reduced pressure to give the title compound (383 g) as a brown oil.

$^{1}$H-NMR(CDCl$_{3}$)δ(ppm): 3.79(2H, s), 7.40(1H, d, J=8.2 Hz), 7.46(1H, dd, J=1.8, 8.2 Hz), 7.60(1H, d, J=1.8 Hz).

Reference Example 15

4-bromo-2-chlorophenylacetic acid

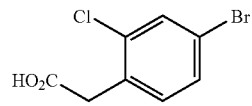

To 4-bromo-2-chlorobenzyl cyanide (383 g) of Reference Example 14 were added water (908 mL), ethanol (6812 mL) and 85% aqueous potassium hydroxide solution (549 g), and the mixture was stirred at an inside temperature of 75° C. for 13 hr. The mixture was concentrated, and diisopropyl ether (4500 mL) and water were added. The aqueous layer was neutralized with 1M hydrochloric acid, and partitioned and extracted with ethyl acetate. The organic layer was washed with 25% brine, and dried over anhydrous magnesium sulfate. The solvent was evaporated under reduced pressure, and the residual crude crystals were recrystallized from a mixed solvent of diisopropyl ether and hexane to give the title compound (240 g) as pale-yellow crystals.

$^{1}$H-NMR(CDCl$_{3}$)δ(ppm): 3.78(2H, s), 7.17(1H, d, J=8.2 Hz), 7.38(1H, dd, J=1.8, 8.2 Hz), 7.57(1H, d, J=1.8 Hz).

Reference Example 16

4-bromo-2-chlorophenylacetic acid methyl ester

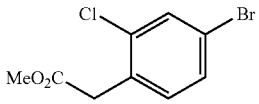

To a solution of 4-bromo-2-chlorophenylacetic acid (240 g) of Reference Example 15 in N,N-dimethylformamide (3000 mL) were added potassium carbonate (399 g) and iodomethane (164 g) at 7° C., and the mixture was stirred at the same temperature for 3 hr and stirred at room temperature for 19 hr. The reaction mixture was poured into water, and partitioned and extracted with ethyl acetate. The organic layer was washed 3 times with 25% brine, and dried over anhydrous magnesium sulfate. The solvent was evaporated under reduced pressure to give the title compound (259 g) as a brown oil.

¹H-NMR(CDCl₃)δ(ppm): 3.71(3H, s), 3.73(2H, s), 7.16 (1H, d, J=8.2 Hz), 7.37(1H, dd, J=2.0, 8.2 Hz), 7.56(1H, d, J=2.0 Hz).

Reference Example 17

2-(4-bromo-2-chlorophenyl)ethanol

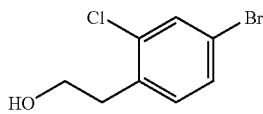

4-Bromo-2-chlorophenylacetic acid methyl ester (259 g) of Reference Example 16 was dissolved in ethanol (1400 mL) and water (355 mL), calcium chloride (107 g) was added at 7° C., and the mixture was stirred for 30 min. To the reaction mixture was added sodium borohydride (73 g) by portions so that the inside temperature would not exceed 15° C. After stirring at 7° C. for 1 hr, the mixture was stirred at room temperature for 1 hr. 0.1M Hydrochloric acid (4257 mL) was added dropwise to the reaction mixture, and the reaction solvent was evaporated under reduced pressure. 0.1M Hydrochloric acid (4257 mL) was added dropwise to the residue, and 1M hydrochloric acid (3000 mL) was further added dropwise. After partitioning and extraction with ethyl acetate, the organic layer was washed with 25% brine, and dried over anhydrous magnesium sulfate. The solvent was evaporated under reduced pressure to give the title compound (229 g) as a brown oil.

¹H-NMR(CDCl₃)δ(ppm): 1.38(1H, brs), 2.97(2H, t, J=6.6 Hz), 3.87(2H, t, J=6.6 Hz), 7.16(1H, d, J=8.2 Hz), 7.34(1H, dd, J=1.8, 8.2 Hz), 7.56(1H, d, J=1.8 Hz).

Reference Example 18

2-(4-bromo-2-chlorophenyl)ethyl iodide

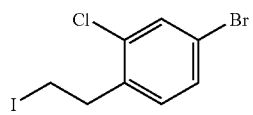

To a solution of 2-(4-bromo-2-chlorophenyl)ethanol (217 g) of Reference Example 17 and triethylamine (112 g) in methylene chloride (2800 mL) was added dropwise methanesulfonyl chloride (116 g) at 0° C., and the mixture was stirred at the same temperature for 1 hr. The reaction mixture was poured into water, and the organic layer was washed with 25% brine and dried over anhydrous sodium sulfate. The solvent was evaporated under reduced pressure, and the residue was dissolved in methyl ethyl ketone (1900 mL). Sodium iodide (166 g) was added, and the mixture was stirred at an inside temperature of 81° C. for 1 hr. The reaction mixture was concentrated under reduced pressure, water was added to the residue, and the mixture was partitioned and extracted with ethyl acetate. The organic layer was washed with 25% aqueous sodium thiosulfate solution and 25% brine, and dried over anhydrous sodium sulfate. The solvent was evaporated under reduced pressure to give the title compound (297 g) as a brown oil.

¹H-NMR(CDCl₃)δ(ppm): 3.22-3.28(2H, m), 3.32-3.38 (2H, m), 7.12(1H, d, J=8.1 Hz), 7.36(1H, dd, J=1.8, 8.1 Hz), 7.53(1H, d, J=2.1 Hz).

Reference Example 19

Diethyl 2-[2-(4-bromo-2-chlorophenyl)ethyl]-2-[(tert-butoxycarbonyl)amino]malonate

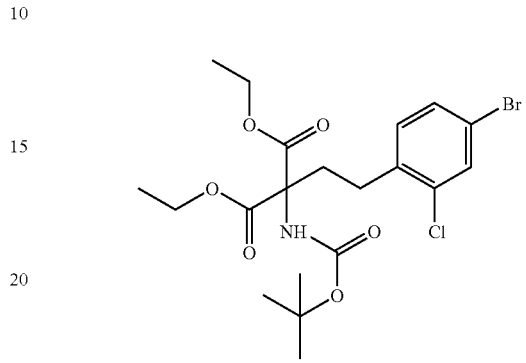

Diethyl(tert-butoxycarbonyl)aminomalonate (202 g) was dissolved in a mixed solution of tetrahydrofuran (6000 mL) and N,N-dimethylformamide (714 mL), and sodium tert-butoxide (70.5 g) was added. After heating the mixture to the refluxing temperature, a solution of 2-(4-bromo-2-chlorophenyl)ethyl iodide (246 g) of Reference Example 18 in tetrahydrofuran (940 mL) was added to the reaction mixture, and the mixture was refluxed with stirring for 15 hr. After cooling, the reaction mixture was poured into 25% aqueous citric acid solution. After partitioning and extraction with ethyl acetate, the organic layer was washed with water and 25% brine, and dried over anhydrous sodium sulfate. The solvent was evaporated under reduced pressure, and the residue was purified by silica gel column chromatography to give the title compound (227 g) as a pale-yellow oil.

¹H-NMR(CDCl₃)δ(ppm): 1.26(6H, t, J=7.1 Hz), 1.44(9H, s), 2.57(4H, s), 4.16-4.30(4H, m), 6.01(1H, s), 7.05(1H, d, J=8.1 Hz), 7.30(1H, dd, J=1.8, 8.4 Hz), 7.49(1H, d, J=1.8 Hz).

Reference Example 20

[1,1-bis(hydroxymethyl)-3-(4-bromo-2-chlorophenyl)propyl]carbamic acid tert-butyl ester

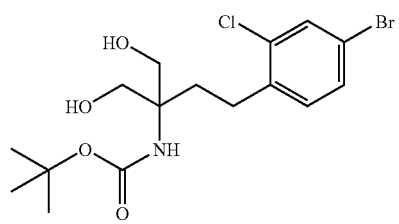

Diethyl 2-[2-(4-bromo-2-chlorophenyl)ethyl]-2-[(tert-butoxycarbonyl)amino]malonate (217 g) of Reference Example 19 was dissolved in a mixed solution of ethanol (2170 mL), tetrahydrofuran (543 mL) and water (1085 mL), calcium chloride (97.7 g) was added at room temperature, and the mixture was stirred for 20 min. To the solution was added sodium borohydride (66.6 g) by portions at 0° C., and the mixture was stirred at the same temperature for 1 hr and further stirred at room temperature for 14 hr. 1M Hydrochloric acid (1085 mL) was added dropwise to the reaction mixture. The reaction solvent was evaporated under reduced pressure. 0.1M Hydrochloric acid (2713 mL) and ethyl acetate (3800 mL) were added to the residue. The organic layer was partitioned and extracted, and the extract was washed with 25% brine, and dried over anhydrous magnesium sulfate. The solvent was evaporated under reduced pressure to give the title compound (175 g) as white crystals.

$^1$H-NMR(CDCl$_3$)δ(ppm): 1.45(9H, s), 1.80-1.86(2H, m), 2.67-2.73(2H, m), 3.32(2H, brs), 3.63-3.69(2H, m), 3.87-3.93(2H, m), 5.10(1H, s), 7.11(1H, d, J=8.2 Hz), 7.32(1H, dd, J=2.1, 8.2 Hz), 7.49(1H, d, J=1.9 Hz).

Reference Example 21

N-[1,1-bis(acetoxymethyl)-3-(4-bromo-2-chlorophenyl)propyl]acetamide

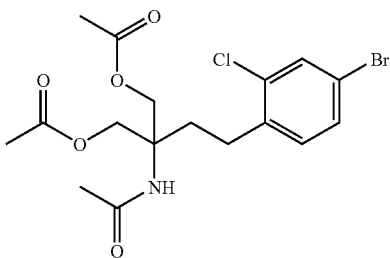

[1,1-Bis(hydroxymethyl)-3-(4-bromo-2-chlorophenyl)propyl]carbamic acid tert-butyl ester (175 g) of Reference Example 20 was dissolved in 4M-HCl/ethyl acetate (326 mL), and the mixture was stirred at 30° C. for 1 hr. The mixture was concentrated under reduced pressure, and 0.1M aqueous sodium hydroxide solution (2713 mL) was added to the residue. After partitioning and extraction with ethyl acetate, the extract was washed with 25% brine, and dried over magnesium sulfate. The solvent was evaporated under reduced pressure, the residue was dissolved in pyridine (271 mL), and acetic anhydride (270 mL) was added under ice-cooling. After stirring at room temperature for 11 hr, ethyl acetate (2710 mL), 1M aqueous sodium hydroxide solution (1084 mL) and 9% aqueous sodium hydrogen carbonate solution (5420 mL) were successively added to the reaction mixture. After partitioning and extraction with ethyl acetate, the extract was washed with 1M hydrochloric acid, 0.1M hydrochloric acid, 9% aqueous sodium hydrogen carbonate solution and 25% brine, and dried over sodium sulfate. The solvent was evaporated under reduced pressure, and the residual pale-yellow crystals were suspended in a mixture of isopropyl ether (880 mL) and n-heptane (880 mL), and collected by filtration to give the title compound (135.3 g) as white crystals.

$^1$H-NMR(CDCl$_3$)δ(ppm): 2.00(3H, s), 2.10(6H, s), 2.12-2.16(2H, m), 2.66-2.72(2H, m), 4.36(4H, s), 5.75(1H, s), 7.10(1H, d, J=8.2 Hz), 7.32(1H, dd, J=1.9, 8.2 Hz), 7.50(1H, d, J=1.9 Hz).

Reference Example 22

N-{1,1-bis(acetoxymethyl)-3-[2-chloro-4-(5,5-dimethyl-1,3,2-dioxaborinan-2-yl)phenyl]propyl}acetamide

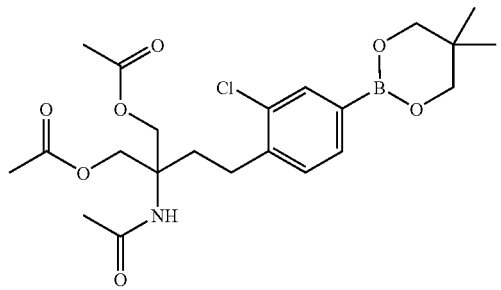

A solution of N-[1,1-bis(acetoxymethyl)-3-(4-bromo-2-chlorophenyl)propyl]acetamide (2.17 g) of Reference Example 21, bis(neopentyl glycolato)diboron (1.24 g), potassium acetate (1.47 g) and dichlorobis(tricyclohexylphosphine)palladium (II) (185 mg) in 1,4-dioxane (20 mL) was stirred at 100° C. for 7 hr. The reaction mixture was poured into water. After extraction with ethyl acetate, the extract was washed with aqueous sodium hydrogen carbonate solution and saturated brine, and dried over anhydrous sodium sulfate. The solvent was evaporated under reduced pressure and the residue was purified by silica gel column chromatography to give the title compound (2.05 g) as pale-yellow amorphous crystals.

$^1$H-NMR(CDCl$_3$)δ(ppm): 1.01(6H, s), 1.99(3H, s), 2.09 (6H, s), 2.12-2.18(2H, m), 2.71-2.77(2H, m), 3.76(4H, s), 4.38(4H, s), 5.71(1H, s), 7.21(1H, d, J=7.8 Hz), 7.59(1H, d, J=7.5 Hz), 7.75(1H, d, J=0.9 Hz).

Reference Example 23

N-[1,1-bis(acetoxymethyl)-3-(4'-bromo-3-chloro-2'-fluorobiphenyl-4-yl)propyl]acetamide

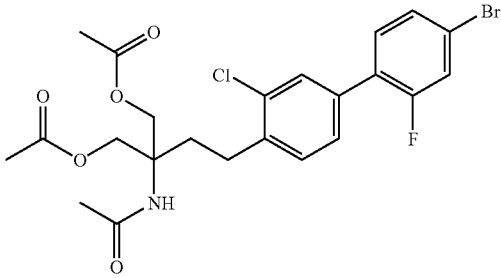

A mixed solution of N-{1,1-bis(acetoxymethyl)-3-[2-chloro-4-(5,5-dimethyl-1,3,2-dioxaborinan-2-yl)phenyl]propyl}acetamide (2.05 g) of Reference Example 22, 1-bromo-3-fluoro-4-iodobenzene (1.39 g), sodium hydrogen carbonate (2.02 g) and tetrakistriphenylphosphine palladium (51 mg) in 1,2-dimethoxyethane (30 mL)-water (10 mL) was stirred at 100° C. for 9 hr. The reaction mixture was extracted with ethyl acetate, washed with saturated brine, and dried over anhydrous sodium sulfate. The solvent was evaporated under reduced pressure. Pyridine (20 mL) and acetic anhydride (2 mL) were added to the residue, and the mixture was stood at room temperature for one day. Water was added to the reaction mixture, the mixture was extracted with ethyl acetate, and the extract was washed with saturated brine, and dried over anhydrous sodium sulfate. The solvent was evaporated under reduced pressure and the residue was purified by silica gel column chromatography to give the title compound (1.30 g) as white crystals.

$^1$H-NMR(CDCl$_3$)δ(ppm): 2.01(3H, s), 2.11(6H, s), 2.18-2.24(2H, m), 2.75-2.81(2H, m), 4.39(4H, s), 5.74(1H, s), 7.24-7.38(5H, m), 7.50(1H, s).

Reference Example 24

Diethyl 2-[2-(4-bromophenyl)ethyl]-2-methylmalonate

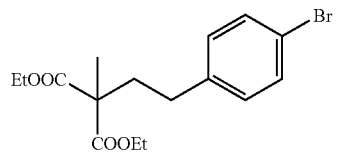

To a solution of diethyl methylmalonate (28.5 g) in N,N-dimethylformamide (350 mL) was added sodium hydride (60%, 7.22 g) in two portions under ice-cooling. After stirring for 40 min under ice-cooling, a solution of 2-(4-bromophenyl)ethyl iodide (56.0 g) obtained in the same manner as in Reference Example 2 in N,N-dimethylformamide (50 mL) was added, and the mixture was stirred for 20 min under ice-cooling and further stirred at 40° C. for 2 hr. The reaction mixture was poured into water. After extraction with ethyl acetate, the extract was washed with saturated brine, and dried over anhydrous magnesium sulfate. The solvent was evaporated under reduced pressure and the residue was purified by silica gel column chromatography to give the title compound (55.1 g) as a colorless oil.

MS(ESI)m/z: 357, 359[M+H]

$^1$H-NMR(CDCl$_3$)δ(ppm): 1.26(6H, t, J=7.1 Hz), 1.48(3H, s), 2.10-2.14(2H, m), 2.51-2.56(2H, m), 4.19(4H, q, J=7.1 Hz), 7.05(2H, d, J=7.9 Hz), 7.39(2H, d, J=7.9 Hz).

Reference Example 25

4-(4-bromophenyl)-2-ethoxycarbonyl-2-methylbutyric acid

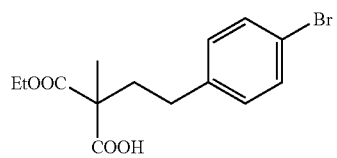

To a solution of diethyl 2-[2-(4-bromophenyl)ethyl]-2-methylmalonate (55.0 g) of Reference Example 24 in ethanol (300 mL) was added potassium hydroxide (85%, 12.2 g), and the mixture was stirred at 60° C. for 5 hr. The solvent was evaporated under reduced pressure, water was added, and the aqueous layer was washed with ether. The aqueous layer was acidified with hydrochloric acid, and the mixture was extracted with ethyl acetate. The organic layer was washed with saturated brine, and dried over anhydrous magnesium sulfate. The solvent was evaporated under reduced pressure to give the title compound (50.8 g) as a colorless oil.

$^1$H-NMR(CDCl$_3$)δ(ppm): 1.29(3H, t, J=7.1 Hz), 1.54(3H, s), 2.09-2.23(2H, m), 2.50-2.63(2H, m), 4.23(2H, q, J=6.7 Hz), 7.05(2H, d, J=8.4 Hz), 7.39(2H, d, J=8.4 Hz).

Reference Example 26 ethyl 4-(4-bromophenyl)-2-methoxycarbonylamino-2-methylbutyrate

A solution of 4-(4-bromophenyl)-2-ethoxycarbonyl-2-methylbutyric acid (50.8 g) of Reference Example 25, triethylamine (25.9 mL) and diphenylphosphoryl azide (40.1 mL) in benzene (400 mL) was stirred at 90° C. for 3 hr. After once cooling to 50° C., methanol (150 mL) was added, and the mixture was heated under reflux for 7 hr. After evaporation of the solvent, water was added, and the mixture was extracted with ethyl acetate. The organic layer was washed with saturated brine, and dried over anhydrous magnesium sulfate. The solvent was evaporated under reduced pressure and the residue was purified by silica gel column chromatography to give the title compound (39.0 g) as a pale-yellow oil.

MS(ESI)m/z: 358, 360[M+H]

$^1$H-NMR(CDCl$_3$)δ(ppm): 1.28(3H, t, J=7.1 Hz), 1.59(3H, s), 2.06-2.11(1H, m), 2.30-2.38(1H, m), 2.52-2.62(2H, m), 3.65(3H, s), 4.14-4.22(2H, m), 5.68(1H, brs), 7.02(2H, d, J=8.4 Hz), 7.37(2H, d, J=8.4 Hz).

Reference Example 27

2-acetamide-4-(4-bromophenyl)-2-methylbutyl acetate

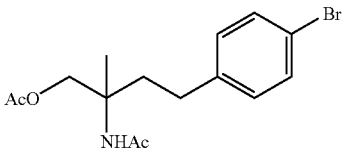

To a mixed solution of ethyl 4-(4-bromophenyl)-2-methoxycarbonylamino-2-methylbutyrate (39.0 g) of Reference Example 26 and calcium chloride (12.1 g) in ethanol (400 mL), tetrahydrofuran (100 mL) and water (200 mL) was added sodium borohydride (8.25 g) in two portions under ice-cooling, and the mixture was stirred for 1 hr under ice-cooling and further stirred at room temperature for 16 hr. The reaction mixture was poured into water (200 mL), and 1M hydrochloric acid (400 mL) was added under ice-cooling. After extraction with ethyl acetate, the organic layer was washed with saturated brine, and dried over anhydrous magnesium sulfate. The solvent was evaporated under reduced pressure, and a mixture of the residue, tetrahydrofuran (150 mL), methanol (200 mL) and 5M aqueous potassium hydroxide solution (216 mL) was heated under reflux for 20 hr. The organic solvent was evaporated under reduced pressure, water (500 mL) was added, and the mixture was extracted with ethyl acetate. The organic layer was washed with saturated brine, and dried over anhydrous magnesium sulfate. The solvent was evaporated under reduced pressure. To a solution of the residue in methylene chloride (30 mL) and pyridine (30 mL) was added acetic anhydride (24.5 mL) under ice-cooling, and the mixture was stirred for 1.5 hr under ice-cooling and stood at room temperature for 17 hr. The reaction mixture was slowly added to ice-cooled saturated aqueous sodium hydrogen carbonate solution (1 L), and the mixture was stirred for 1 hr under ice-cooling. After extraction with ethyl acetate, the organic layer was washed with 1M hydrochloric acid, aqueous sodium hydrogen carbonate solution and saturated brine, and dried over anhydrous magnesium sulfate. The solvent was evaporated under reduced pressure, the residue was crystallized from diisopropyl ether, and the resulting crystals were collected by filtration to give the title compound (20.3 g) as pale-yellow crystals.

MS(ESI)m/z: 342, 344 [M+H]

$^1$H-NMR(CDCl$_3$)δ(ppm): 1.36(3H, s), 1.89-1.96(1H, m), 1.94(3H, s), 2.09(3H, s), 2.18-2.26(1H, m), 2.51-2.58(2H, m), 4.15(1H, d, J=11.2 Hz), 4.32(1H, d, J=11.2 Hz), 5.36(1H, brs), 7.06(2H, d, J=8.3 Hz), 7.38(2H, d, J=8.3 Hz).

Reference Example 28

2-acetamide-4-[4-(5,5-dimethyl-1,3,2-dioxaborinan-2-yl)phenyl]-2-methylbutyl acetate

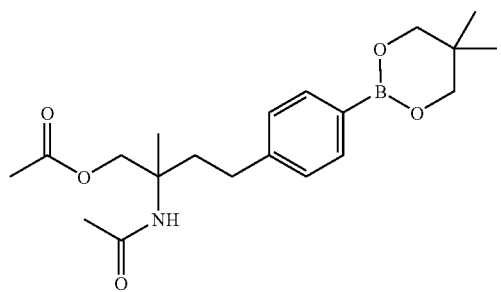

A solution of 2-acetamide-4-(4-bromophenyl)-2-methylbutyl acetate (1.71 g) of Reference Example 27, bis(neopentyl glycolato)diboron (1.24 g), potassium acetate (1.47 g) and dichlorobis(tricyclohexylphosphine)palladium (II) (185 mg) in 1,4-dioxane (20 mL) was stirred at 100° C. for 6 hr. The reaction mixture was poured into aqueous sodium hydrogen carbonate solution. After extraction with ethyl acetate, the extract was washed with saturated brine, and dried over anhydrous sodium sulfate. The solvent was evaporated under reduced pressure and the residue was purified by silica gel column chromatography to give the title compound (1.44 g) as white crystals.

$^1$H-NMR(CDCl$_3$)δ(ppm): 1.01(6H, s), 1.37(3H, s), 1.87-1.97(1H, m), 1.91(3H, s), 2.09(3H, s), 2.16-2.26(1H, m), 2.61(2H, t, J=8.6 Hz), 3.76(4H, s), 4.18(1H, d, J=11.1 Hz), 4.33(1H, d, J=11.1 Hz), 5.33(1H, s), 7.18(2H, d, J=7.5 Hz), 7.71(2H, d, J=7.8 Hz).

Reference Example 29

2-acetamide-4-(4'-bromo-2'-fluorobiphenyl-4-yl)-2-methylbutyl acetate

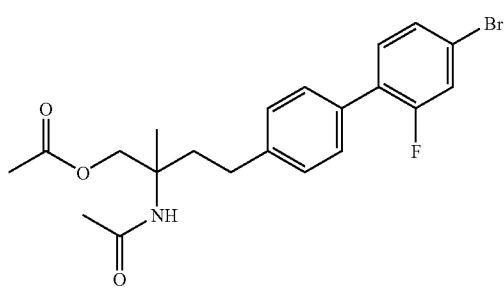

A mixed solution of 2-acetamide-4-[4-(5,5-dimethyl-1,3,2-dioxaborinan-2-yl)phenyl]-2-methylbutyl acetate (1.44 g) of Reference Example 28, 1-bromo-3-fluoro-4-iodobenzene (1.21 g), sodium hydrogen carbonate (1.94 g) and tetrakistriphenylphosphine palladium (222 mg) in 1,2-dimethoxyethane (30 mL)-water (10 mL) was stirred at 100° C. for 14 hr. The reaction mixture was extracted with ethyl acetate, and the extract was washed with saturated brine and dried over anhydrous sodium sulfate. The solvent was evaporated under reduced pressure. Pyridine (6 mL) and acetic anhydride (2 mL) were added to the residue, and the mixture was stood at room temperature for one day. Water was added to the reaction mixture, and the mixture was extracted with ethyl acetate. The extract was washed with saturated brine, and dried over anhydrous sodium sulfate. The solvent was evaporated under reduced pressure and the residue was purified by silica gel column chromatography to give the title compound (0.88 g) as white crystals.

$^1$H-NMR(CDCl$_3$)δ(ppm): 1.39(3H, s), 1.92-2.03(1H, m), 1.94(3H, s), 2.10(3H, s), 2.26-2.34(1H, m), 2.65(2H, t, J=8.7 Hz), 4.19(1H, d, J=11.1 Hz), 4.36(1H, d, J=11.4 Hz), 5.39 (1H, s), 7.26-7.36(5H, m), 7.43(2H, dd, J=1.2, 7.8 Hz).

Reference Example 30

4-(4-bromophenyl)-2-ethoxycarbonyl-2-ethylbutyric acid

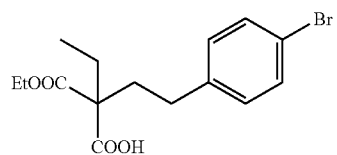

To a solution of diethyl ethylmalonate (42.6 g) in N,N-dimethylformamide (350 mL) was added sodium hydride (60%, 9.96 g) in two portions under ice-cooling. After stirring for 30 min under ice-cooling, a solution of 2-(4-bromophenyl)ethyl iodide (77.4 g) obtained in the same manner as in Reference Example 2 in N,N-dimethylformamide (50 mL) was added, and the mixture was stirred for 20 min under ice-cooling and further stirred at 40° C. for 2.5 hr. The reaction mixture was poured into water. After extraction with ethyl acetate, the extract was washed with saturated brine, and dried over anhydrous magnesium sulfate. The solvent was evaporated under reduced pressure. To a solution of the residue in ethanol (300 mL) was added potassium hydroxide (85%, 15.2 g), and the mixture was stirred at 65° C. for 10 hr. The solvent was evaporated under reduced pressure, water was added, and the aqueous layer was washed with ether. The aqueous layer was acidified with hydrochloric acid, and the mixture was extracted with ethyl acetate. The organic layer was washed with saturated brine, and dried over anhydrous magnesium sulfate. The solvent was evaporated under reduced pressure to give the title compound (71.0 g) as a yellow oil.

$^1$H-NMR(CDCl$_3$)δ(ppm): 0.89(3H, t, J=7.5 Hz), 1.32(3H, t, J=7.2 Hz), 1.90-2.00(1H, m), 2.02-2.18(2H, m), 2.22-2.31 (1H, m), 2.37-2.44(1H, m), 2.52-2.60(1H, m), 4.18-4.31(2H, m), 7.03(2H, d, J=8.4 Hz), 7.39(2H, d, J=8.4 Hz).

Reference Example 31

Ethyl 4-(4-bromophenyl)-2-ethyl-2-(methoxycarbonylamino)butyrate

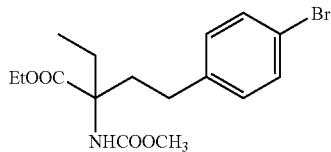

A solution of 4-(4-bromophenyl)-2-ethoxycarbonyl-2-ethylbutyric acid (71.0 g) of Reference Example 30, triethylamine (34.6 mL) and diphenylphosphoryl azide (53.4 mL) in benzene (500 mL) was stirred at 90° C. for 2.5 hr. After once cooling to 50° C., methanol (200 mL) was added, and the mixture was heated under reflux for 7 hr. After evaporation of the solvent, water was added, and the mixture was extracted with ethyl acetate. The organic layer was washed with saturated brine, and dried over anhydrous magnesium sulfate. The solvent was evaporated under reduced pressure and the residue was purified by silica gel column chromatography to give the title compound (53.5 g) as a colorless oil.

MS(ESI)m/z: 372, 374[M+H]

$^1$H-NMR(CDCl$_3$)δ(ppm): 0.76(3H, t, J=7.4 Hz), 1.29(3H, t, J=7.3 Hz), 1.71-1.80(1H, m), 2.01-2.08(1H, m), 2.24-2.39 (2H, m), 2.53-2.62(1H, m), 2.64-2.73(1H, m), 3.64(3H, s), 4.09-4.25(2H, m), 5.81(1H, br.s), 7.01(2H, d, J=8.2 Hz), 7.37 (2H, d, J=8.2 Hz).

Reference Example 32

2-acetamide-2-ethyl-4-(4-bromophenyl)butyl acetate

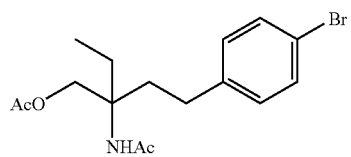

To a solution of ethyl 4-(4-bromophenyl)-2-ethyl-2-(methoxycarbonylamino)butyrate (52.9 g) of Reference Example 31 in tetrahydrofuran (500 mL) was added lithium borohydride (6.19 g), and the mixture was heated under reflux for 1.5 hr. After once cooling to 50° C., lithium borohydride (3.08 g) was added, and the mixture was heated under reflux for 2 hr. The reaction mixture was poured into water (2 L) after cooling, and 1M hydrochloric acid (1 L) was slowly added under ice-cooling. After extraction with ethyl acetate, the organic layer was washed with saturated brine, and dried over anhydrous magnesium sulfate. The solvent was evaporated under reduced pressure. A mixture of the residue, tetrahydrofuran (150 mL), methanol (220 mL) and 5M aqueous potassium hydroxide solution (260 mL) was heated under reflux for 24 hr. The organic solvent was evaporated under reduced pressure, water (500 mL) was added, and the mixture was extracted with ethyl acetate. The organic layer was washed with saturated brine, and dried over anhydrous magnesium sulfate. The solvent was evaporated under reduced pressure. To a solution of the residue in pyridine (35 mL) was added acetic anhydride (32.2 mL) under ice-cooling, and the mixture was stirred for 1 hr under ice-cooling and stood at room temperature for 9 hr. The reaction mixture was slowly added to ice-cooled saturated aqueous sodium hydrogen carbonate solution (1 L), and the mixture was extracted with ethyl acetate. The organic layer was washed with 1M hydrochloric acid, aqueous sodium hydrogen carbonate solution and saturated brine, and dried over anhydrous magnesium sulfate. The solvent was evaporated under reduced pressure, the residue was crystallized from diisopropyl ether, and the resulting crystals were collected by filtration to give the title compound (34.9 g) as white crystals.

MS(ESI)m/z: 356, 358[M+H]

$^1$H-NMR(CDCl$_3$)δ(ppm): 0.89(3H, t, J=7.6 Hz), 1.75-1.85 (2H, m), 1.91-1.99(1H, m), 1.95(3H, s), 2.07-2.15(1H, m), 2.09(3H, s), 2.48-2.54(2H, m), 4.27(1H, d, J=11.3 Hz), 4.31 (1H, d, J=11.3 Hz), 5.23(1H, br.s), 7.05(2H, d, J=8.4 Hz), 7.39(2H, d, J=8.4 Hz).

Reference Example 33

2-acetamide-4-[4-(5,5-dimethyl-1,3,2-dioxaborinan-2-yl)phenyl]-2-ethylbutyl acetate

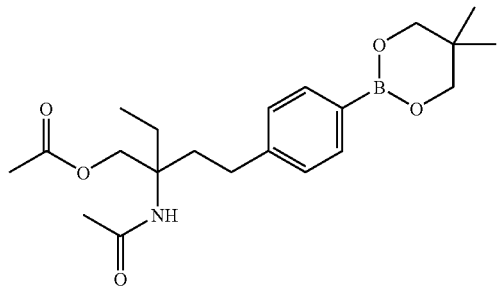

A solution of 2-acetamide-2-ethyl-4-(4-bromophenyl)butyl acetate (1.78 g) of Reference Example 32, bis(neopentyl glycolato)diboron (1.24 g), potassium acetate (1.47 g) and dichlorobis(tricyclohexylphosphine)palladium (II) (185 mg) in 1,4-dioxane (20 mL) was stirred at 100° C. for 6 hr. The reaction mixture was poured into aqueous sodium hydrogen carbonate solution. After extraction with ethyl acetate, the extract was washed with saturated brine, and dried over anhydrous sodium sulfate. The solvent was evaporated under reduced pressure and the residue was purified by silica gel column chromatography to give the title compound (1.63 g) as brown amorphous crystals.

$^1$H-NMR(CDCl$_3$)δ(ppm): 0.88(3H, t, J=7.5 Hz), 1.01(6H, s), 1.70-2.18(4H, m), 1.93(3H, s), 2.08(3H, s), 2.56(2H, t, J=8.6 Hz), 3.76(4H, s), 4.32(2H, s), 5.26(1H, s), 7.17(2H, d, J=7.5 Hz), 7.71(2H, d, J=7.8 Hz).

Reference Example 34

2-acetamide-4-(4'-bromo-2'-fluorobiphenyl-4-yl)-2-ethylbutyl acetate

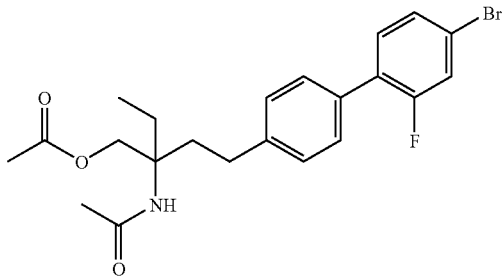

A mixed solution of 2-acetamide-4-[4-(5,5-dimethyl-1,3,2-dioxaborinan-2-yl)phenyl]-2-ethylbutyl acetate (1.63 g) of Reference Example 33, 1-bromo-3-fluoro-4-iodobenzene (1.32 g), sodium hydrogen carbonate (2.11 g) and tetrakistriphenylphosphine palladium (242 mg) in 1,2-dimethoxyethane (30 mL)-water (10 mL) was stirred at 100° C. for 14 hr. The reaction mixture was extracted with ethyl acetate, and the extract was washed with saturated brine and dried over anhydrous sodium sulfate. The solvent was evaporated under reduced pressure. Pyridine (6 mL) and acetic anhydride (2 mL) were added to the residue, and the mixture was stood at room temperature for one day. Water was added to the reaction mixture, and the mixture was extracted with ethyl acetate. The extract was washed with saturated brine, and dried over anhydrous sodium sulfate. The solvent was evaporated under reduced pressure and the residue was purified by silica gel column chromatography to give the title compound (1.02 g) as white crystals.

$^1$H-NMR(CDCl$_3$)δ(ppm): 0.91(3H, t, J=7.5 Hz), 1.70-2.25 (4H, m), 1.96(3H, s), 2.10(3H, s), 2.61(2H, t, J=8.5 Hz), 4.30(2H, d, J=11.4 Hz), 4.36(2H, d, J=11.4 Hz), 7.25-7.36 (5H, m), 7.43(2H, dd, J=1.5, 8.2 Hz).

Example 1

2-amino-2-{2-[4-(5-phenylthionaphthalen-1-yl)phenyl]ethyl}propane-1,3-diol hydrochloride (1-1) Synthesis of N-{1,1-bis(acetoxymethyl)-3-[4-(5-benzyloxynaphthalen-1-yl)phenyl]propyl}acetamide

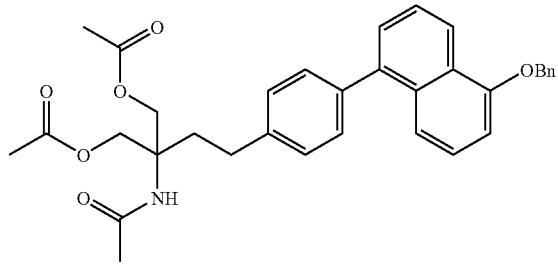

The compound (2.30 g) of Reference Example 8 was dissolved in tetrahydrofuran (11 mL), a compound (2.33 g) obtained in the same manner as in Reference Example 1, palladium acetate (60 mg), 2-dicyclohexylphosphino-2'6'-dimethoxybiphenyl (S-phos) (105 mg) and tripotassium phosphate (2.20 g) were added, and the mixture was stirred at 60° C. for 4.5 hr. Palladium acetate (30 mg) and S-phos (50 mg) were further added, and the mixture was stirred at 70° C. for 2 hr. Water was added to the reaction mixture, and the mixture was extracted with ethyl acetate. The extract was washed with water and saturated brine, and dried over anhydrous sodium sulfate. The solvent was evaporated under reduced pressure, the residue was purified by silica gel column chromatography (hexane:ethyl acetate=1:2), and the resulting crystals were washed with diethyl ether to give the object product (1.5 g) as pale-yellow crystals.

MS(ESI)m/z: 554[M+H]

$^1$H-NMR(DMSO-d$_6$)δ(ppm): 1.88(3H, s), 2.05(6H, s), 2.05-2.10(2H, m), 2.62-2.66(2H, m), 4.23(2H, d, J=11.0 Hz), 4.32(2H, d, J=11.0 Hz), 5.34(2H, s), 7.11(1H, dd, J=2.7, 5.7 Hz), 7.31-7.46(10H, m), 7.54-7.58(3H, m), 7.68(1H, s), 8.26 (1H, d, J=8.4 Hz).

(1-2) Synthesis of N-{1,1-bis(acetoxymethyl)-3-[4-(5-hydroxynaphthalen-1-yl)phenyl]propyl}acetamide

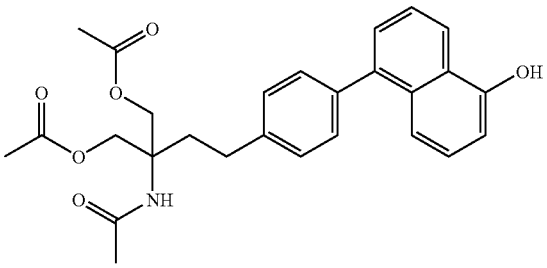

The compound (1.45 g) of Example (1-1) was dissolved in ethyl acetate (30 mL) and methanol (10 mL), 10% palladium carbon (500 mg) was added, and the mixture was stirred at room temperature for 5 hr under a hydrogen atmosphere. After celite filtration, the filtrate was concentrated, and the residue was washed with diethyl ether to give the object product (0.99 g) as white crystals.

MS(ESI)m/z: 464[M+H]

$^1$H-NMR(DMSO-d$_6$)δ(ppm): 1.88(3H, s), 2.05(6H, s), 2.05-2.09(2H, m), 2.62-2.66(2H, m), 4.23(2H, d, J=11.0 Hz), 4.32(2H, d, J=11.0 Hz), 6.89(1H, dd, J=1.4, 6.4 Hz), 7.21-7.40(7H, m), 7.46-7.50(1H, m), 7.68(1H, s), 8.17(1H, d, J=8.4 Hz), 10.15(1H, brs).

(1-3) Synthesis of N-{1,1-bis(acetoxymethyl)-3-[4-(5-trifluoromethanesulfonyloxynaphthalen-1-yl)phenyl]propyl}acetamide

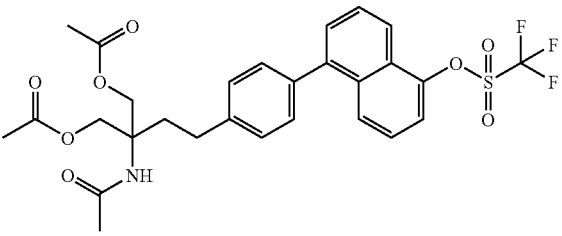

The compound (0.99 g) of Example (1-2) was dissolved in dichloromethane (15 mL) and pyridine (850 μL), and trifluoromethanesulfonic anhydride (430 μL) diluted with dichloromethane (5 mL) was slowly added dropwise at 0° C. After stirring at the same temperature for 1 hr, aqueous sodium hydrogen carbonate was added to the reaction mixture, and the mixture was extracted with dichloromethane. The organic layer was washed with saturated brine, and dried over anhydrous sodium sulfate. The solvent was evaporated under reduced pressure and the residue was purified by silica gel column chromatography (hexane:ethyl acetate=1:2). The resulting crystals were washed with hexane to give the object product (0.95 g) as yellow crystals.

$^1$H-NMR(DMSO-d$_6$)δ(ppm): 1.90(3H, s), 2.07(6H, s), 2.07-2.12(2H, m), 2.66-2.70(2H, m), 4.25(2H, d, J=11.0 Hz), 4.34(2H, d, J=11.1 Hz), 7.38(2H, d, J=8.2 Hz), 7.44(2H, d, J=8.2 Hz), 7.62-7.76(4H, m), 7.86(1H, dd, J=7.3, 8.2 Hz), 7.95(1H, d, J=8.6 Hz), 8.03(1H, d, J=8.4 Hz).

(1-4) Synthesis of N-{1,1-bis(acetoxymethyl)-3-[4-(5-phenylthionaphthalen-1-yl)phenyl]propyl}acetamide

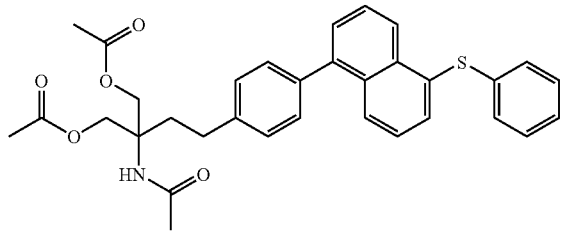

The compound (200 mg) of Example (1-3) was dissolved in 1,4-dioxane (700 μL), and benzenethiol (40 μL), tris(dibenzylideneacetone)dipalladium(0) chloroform adduct (9 mg), 4,5-bis(diphenylphosphino)-9,9-dimethylxanthene (Xantphos) (10 mg) and diisopropylethylamine (120 μL) were added. The mixture was stirred at 120° C. for 3 hr. Water was added to the reaction mixture, and the mixture was extracted with ethyl acetate. The extract was washed with water and saturated brine, and dried over anhydrous sodium sulfate. The solvent was evaporated under reduced pressure and the residue was crudely purified by silica gel column chromatography (hexane:ethyl acetate=1:1) to give a mixture (170 mg) as a yellow oil.

(1-5) Synthesis of 2-amino-2-{2-[4-(5-phenylthionaphthalen-1-yl)phenyl]ethyl}propane-1,3-diol hydrochloride

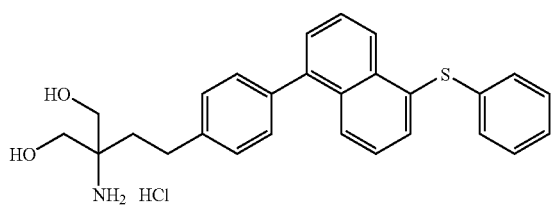

The mixture (170 mg) of Example (1-4) was dissolved in a mixed solvent of methanol (1.5 mL), water (1.5 mL) and tetrahydrofuran (0.5 mL), lithium hydroxide monohydrate (50 mg) was added, and the mixture was stirred at 70° C. for 4 hr. Water was added to the reaction mixture, and the mixture was extracted with ethyl acetate. The extract was washed with water and saturated brine, and dried over anhydrous sodium sulfate. The solvent was evaporated under reduced pressure, the residue was purified by preparative HPLC, and the obtained oil was dissolved in dichloromethane (2 mL). 4M-Hydrochloric acid-1,4-dioxane (200 μL) was added, and the mixture was stirred at room temperature. The resulting crystals were washed with diethyl ether to give the object product (30 mg) as white crystals.

MS(ESI)m/z: 430[M+H]

$^1$H-NMR(DMSO-d$_6$)δ(ppm): 1.87-1.92(2H, m), 2.70-2.74 (2H, m), 3.57(4H, d, J=4.8 Hz), 5.40(2H, t, J=4.8 Hz), 7.20-7.53(11H, m), 7.63-7.67(1H, m), 7.73(1H, d, J=7.2 Hz), 7.78 (3H, brs), 7.87(1H, d, J=8.6 Hz), 8.33(1H, d, J=8.5 Hz).

Example 2

2-amino-2-(2-{4-[5-(4-methylphenylthio)naphthalen-1-yl]phenyl}ethyl)propane-1,3-diol hydrochloride (2-1) Synthesis of N-(1,1-bis(acetoxymethyl)-3-{4-[5-(4-methylphenylthio)naphthalen-1-yl]phenyl}propyl)acetamide

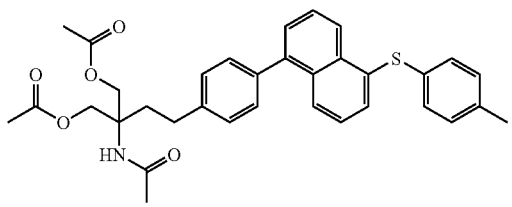

The compound (200 mg) of Example (1-3) was dissolved in 1,4-dioxane (700 μL), and 4-methylbenzenethiol (40 μL), tris(dibenzylideneacetone)dipalladium(0) chloroform adduct (9 mg), 4,5-bis(diphenylphosphino)-9,9-dimethylxanthene (Xantphos) (10 mg) and diisopropylethylamine (120 μL) were added. The mixture was stirred at 120° C. for 3 hr. Water was added to the reaction mixture, and the mixture was extracted with ethyl acetate. The extract was washed with water and saturated brine, and dried over anhydrous sodium sulfate. The solvent was evaporated under reduced pressure and the residue was crudely purified by silica gel column chromatography (hexane:ethyl acetate=1:1) to give a mixture (180 mg) as a yellow oil.

(2-2) Synthesis of 2-amino-2-(2-{4-[5-(4-methylphenylthio)naphthalen-1-yl]phenyl}ethyl)propane-1,3-diol hydrochloride

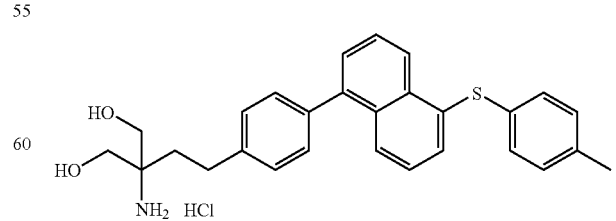

The mixture (180 mg) of Example (2-1) was dissolved in a mixed solvent of methanol (1.5 mL), water (1.5 mL) and tetrahydrofuran (0.5 mL), lithium hydroxide monohydrate (50 mg) was added, and the mixture was stirred at 70° C. for 4 hr. Water was added to the reaction mixture, and the mixture was extracted with ethyl acetate. The extract was washed with water and saturated brine, and dried over anhydrous sodium sulfate. The solvent was evaporated under reduced pressure and the residue was purified by preparative HPLC. The obtained oil was dissolved in dichloromethane (2 mL). 4M Hydrochloric acid-1,4-dioxane (200 μl) was added, and the mixture was stirred at room temperature. The resulting crystals were washed with diethyl ether to give the object product (30 mg) as white crystals.

MS(ESI)m/z: 444[M+H]

$^1$H-NMR(DMSO-d$_6$)δ(ppm): 1.87-1.92(2H, m), 2.27(3H, s), 2.70-2.74(2H, m), 3.57(4H, d, J=4.7 Hz), 5.40(2H, t, J=4.9 Hz), 7.16-7.20(4H, m), 7.37-7.48(6H, m), 7.58-7.66(2H, m), 7.79-7.83(4H, m), 8.32(1H, d, J=8.6 Hz).

Example 3

2-amino-2-{2-[2'-fluoro-4'-(phenylthio)biphenyl-4-yl]ethyl}propane-1,3-diol hydrochloride (3-1) Synthesis of N-(5-{2-[2'-fluoro-4'-(phenylthio)biphenyl-4-yl]ethyl}-2,2-dimethyl-1,3-dioxan-5-yl)acetamide

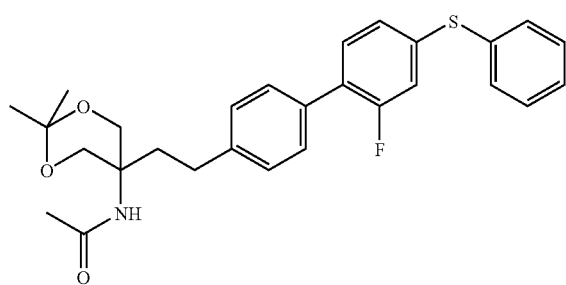

A solution of N-{5-[2-(4'-bromo-2'-fluorobiphenyl-4-yl)ethyl]-2,2-dimethyl-1,3-dioxan-5-yl}acetamide (450 mg) of Reference Example 10, benzenethiol (121 mg), diisopropylethylamine (258 mg), tris(dibenzylideneacetone)dipalladium (0) chloroform adduct (25.9 mg) and 4,5-bis(diphenylphosphino)-9,9-dimethylxanthene (Xantphos) (29.8 mg) in 1,4-dioxane (5 mL) was heated under reflux for 8 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (468 mg) as a pale-yellow oil.

$^1$H-NMR(CDCl$_3$)δ(ppm): 1.43(6H, s), 2.02(3H, s), 2.07-2.13(2H, m), 2.55-2.61(2H, m), 3.69(2H, d, J=11.7 Hz), 4.00 (2H, d, J=11.7 Hz), 5.79(1H, s), 7.02(1H, d, J=11.1 Hz), 7.10(1H, d, J=9.6 Hz), 7.23-7.47(10H, m).

(3-2) Synthesis of 2-amino-2-{2-[2'-fluoro-4'-(phenylthio)biphenyl-4-yl]ethyl}propane-1,3-diol hydrochloride

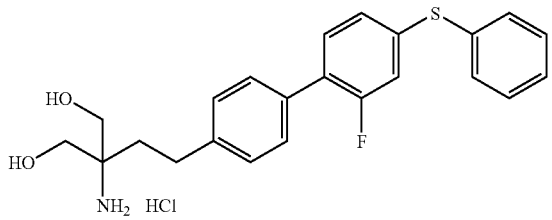

N-(5-{2-[2'-Fluoro-4'-(phenylthio)biphenyl-4-yl]ethyl}-2,2-dimethyl-1,3-dioxan-5-yl)acetamide (468 mg) was dissolved in methanol (6 mL), concentrated hydrochloric acid (3 mL) was added, and the mixture was stirred at 70° C. for 3.5 hr. The reaction mixture was concentrated, and the residual crude crystals were suspended in diisopropyl ether and collected by filtration to give the title compound (329 mg) as white crystals.

MS(ESI)m/z: 398[M+H]

$^1$H-NMR(DMSO-d$_6$)δ(ppm): 1.79-1.85(2H, m), 2.63-2.69 (2H, m), 3.54(4H, d, J=4.5 Hz), 5.41(2H, t, J=5.0 Hz), 7.13-7.17(2H, m), 7.32(2H, d, J=8.4 Hz), 7.44-7.53(8H, m), 7.83 (3H, brs).

Example 4

2-amino-2-{2-[2'-fluoro-4'-(4-methylphenylthio)biphenyl-4-yl]ethyl}propane-1,3-diol (4-1) Synthesis of N-(5-{2-[2'-fluoro-4'-(4-methylphenylthio)biphenyl-4-yl]ethyl}-2,2-dimethyl-1,3-dioxan-5-yl)acetamide

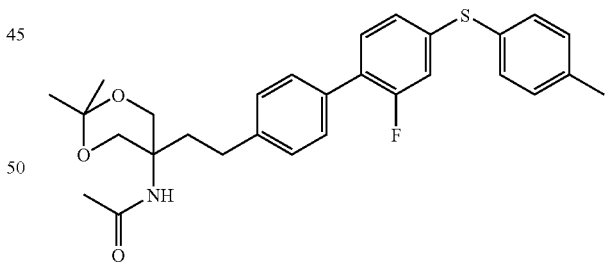

A solution of N-{5-[2-(4'-bromo-2'-fluorobiphenyl-4-yl)ethyl]-2,2-dimethyl-1,3-dioxan-5-yl}acetamide (1.17 g) of Reference Example 10, 4-methylbenzenethiol (316 mg), diisopropylethylamine (672 mg), tris(dibenzylideneacetone)dipalladium(0) chloroform adduct (67.3 mg) and 4,5-bis(diphenylphosphino)-9,9-dimethylxanthene (Xantphos) (77.5 mg) in 1,4-dioxane (10 mL) was heated under reflux for 8 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (1.12 g) as pale-yellow crystals.

¹H-NMR(CDCl₃)δ(ppm): 1.43(6H, s), 2.02(3H, s), 2.05-2.12(2H, m), 2.38(3H, s), 2.55-2.60(2H, m), 3.69(2H, d, J=12.0 Hz), 3.99(2H, d, J=12.0 Hz), 5.74(1H, s), 6.93(1H, d, J=11.1 Hz), 7.03(1H, d, J=9.9 Hz), 7.18-7.42(9H, m).

(4-2) Synthesis of 2-amino-2-{2-[2'-fluoro-4'-(4-methylphenylthio)biphenyl-4-yl]ethyl}propane-1,3-diol

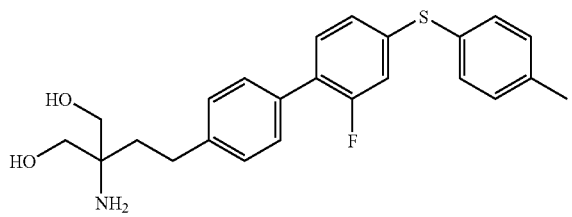

N-(5-{2-[2'-Fluoro-4'-(4-methylphenylthio)biphenyl-4-yl]ethyl}-2,2-dimethyl-1,3-dioxan-5-yl)acetamide (1.187 g) was dissolved in ethanol (20 mL), concentrated hydrochloric acid (10 mL) was added, and the mixture was stirred at 80° C. for 5 hr. The reaction mixture was concentrated, aqueous potassium carbonate solution was added to the residue, and the precipitated crystals were collected by filtration. The crude crystals were purified by preparative HPLC to give the title compound (491 mg) as white crystals.

MS(ESI)m/z: 412[M+H]

¹H-NMR(DMSO-d₆)δ(ppm): 1.30(2H, brs), 1.49-1.54 (2H, m), 2.35(3H, s), 2.60-2.65(2H, m), 3.19-3.29(4H, m), 4.47(2H, brs), 7.04(2H, d, J=9.9 Hz), 7.29(4H, m), 7.39-7.48 (5H, m).

Example 5

2-amino-2-{2-[2'-fluoro-4'-(3-methylphenylthio)biphenyl-4-yl]ethyl}propane-1,3-diol hydrochloride (5-1) Synthesis of N-[5-{2-[2'-fluoro-4'-(3-methylphenylthio)biphenyl-4-yl]ethyl)-2,2-dimethyl-1,3-dioxan-5-yl}acetamide

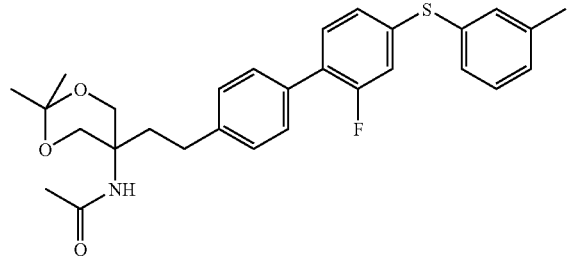

A solution of N-{5-[2-(4'-bromo-2'-fluorobiphenyl-4-yl)ethyl]-2,2-dimethyl-1,3-dioxan-5-yl}acetamide (158 mg) of Reference Example 10, 3-methylbenzenethiol (48 mg), diisopropylethylamine (90 mg), tris(dibenzylideneacetone)dipalladium(0) chloroform adduct (9.1 mg) and 4,5-bis(diphenylphosphino)-9,9-dimethylxanthene (Xantphos) (10.4 mg) in 1,4-dioxane (2 mL) was heated under reflux for 13 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (187 mg) as a colorless oil.

¹H-NMR(CDCl₃) (ppm): 1.43(6H, s), 2.02(3H, s), 2.07-2.13(2H, m), 2.35(3H, s), 2.55-2.61(2H, m), 3.70(2H, d, J=11.9 Hz), 4.00(2H, d, J=11.9 Hz), 5.78(1H, s), 7.00(1H, d, J=11.8 Hz), 7.07-7.10(1H, m), 7.23-7.43(9H, m).

(5-2) Synthesis of 2-amino-2-{2-[2'-fluoro-4'-(3-methylphenylthio)biphenyl-4-yl]ethyl}propane-1,3-diol hydrochloride

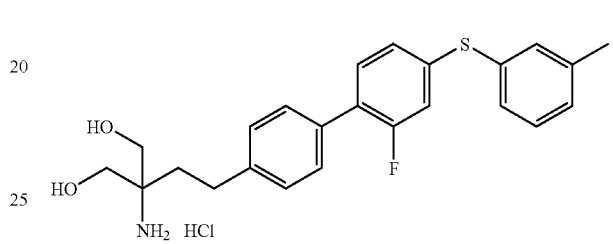

N-[5-{2-[2'-Fluoro-4'-(3-methylphenylthio)biphenyl-4-yl]ethyl}-2,2-dimethyl-1,3-dioxan-5-yl]acetamide (187 mg) was dissolved in methanol (4 mL), concentrated hydrochloric acid (2 mL) was added, and the mixture was stirred at 70° C. for 7 hr. The reaction mixture was concentrated, and the residual crude crystals were suspended in ethyl acetate and collected by filtration to give the title compound (52 mg) as white crystals.

MS(ESI)m/z: 412[M+H]

¹H-NMR(DMSO-d₆)δ(ppm): 1.79-1.85(2H, m), 2.33(3H, s), 2.63-2.68(2H, m), 3.53-3.54(4H, m), 5.39(2H, t, J=4.7 Hz), 7.10-7.14(2H, m), 7.23-7.49(9H, m), 7.81(3H, brs).

Example 6

Synthesis of 2-amino-2-{2-[4'-(4-ethylphenylthio)-2'-fluoro-biphenyl-4-yl]ethyl}propane-1,3-diol

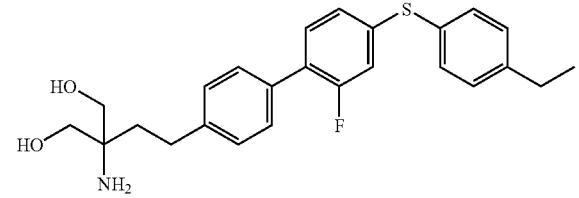

A solution of N-{5-[2-(4'-bromo-2'-fluorobiphenyl-4-yl)ethyl]-2,2-dimethyl-1,3-dioxan-5-yl}acetamide (225 mg) of Reference Example 10, 4-ethylbenzenethiol (69 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 8 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the obtained residue was dissolved in ethanol (4 mL). Concentrated hydrochloric acid (2 mL) was added, and the mixture was stirred at 80° C. for 4 hr. The reaction mixture was concentrated, aqueous potassium carbonate solution was added to the residue, and the precipitated crystals were collected by filtration. The crude crystals were purified by preparative HPLC to give the title compound (84 mg) as white crystals.

MS (ESI) m/z: 426[M+H]
$^1$H-NMR(DMSO-d$_6$)δ(ppm): 1.20(3H, t, J=7.5 Hz), 1.29 (2H, brs), 1.49-1.54(2H, m), 2.60-2.68(4H, m), 3.21-3.29 (4H, m), 4.46(2H, t, J=5.1 Hz), 7.05-7.08(2H, m), 7.09-7.34 (4H, m), 7.40-7.49(5H, m).

Example 7

Synthesis of 2-amino-2-{2-[2'-fluoro-4'-(3-fluorophenylthio)biphenyl-4-yl]ethyl}propane-1,3-diol

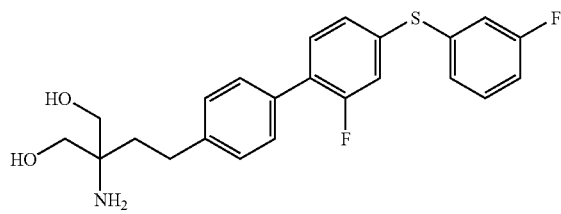

A solution of N-{5-[2-(4'-bromo-2'-fluorobiphenyl-4-yl) ethyl]-2,2-dimethyl-1,3-dioxan-5-yl}acetamide (225 mg) of Reference Example 10, 3-fluorobenzenethiol (64 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 6 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the obtained residue was dissolved in ethanol (4 mL). Concentrated hydrochloric acid (2 mL) was added, and the mixture was stirred at 80° C. for 4 hr. The reaction mixture was concentrated, aqueous potassium carbonate solution was added to the residue, and the precipitated crystals were collected by filtration. The crude crystals were purified by preparative HPLC to give the title compound (47 mg) as white crystals.

MS(ESI)m/z: 416[M+H]
$^1$H-NMR(DMSO-d$_6$)δ(ppm): 1.30(2H, brs), 1.50-1.56 (2H, m), 2.61-2.67(2H, m), 3.19-3.30(4H, m), 4.47(2H, t, J=5.4 Hz), 7.23-7.33(7H, m), 7.44-7.55(4H, m).

Example 8

Synthesis of 2-amino-2-{2-[2'-fluoro-4'-(2-fluoro-4-methylphenylthio)biphenyl-4-yl]ethyl}propane-1,3-diol

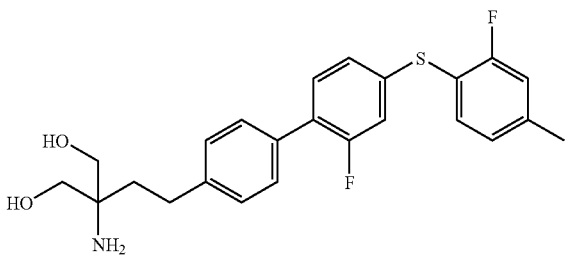

A solution of N-{5-[2-(4'-bromo-2'-fluorobiphenyl-4-yl) ethyl]-2,2-dimethyl-1,3-dioxan-5-yl}acetamide (225 mg) of Reference Example 10, 2-fluoro-4-methylbenzenethiol (71 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 6 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the obtained residue was dissolved in ethanol (4 mL). Concentrated hydrochloric acid (2 mL) was added, and the mixture was stirred at 80° C. for 4 hr. The reaction mixture was concentrated, aqueous potassium carbonate solution was added to the residue, and the precipitated crystals were collected by filtration. The crude crystals were purified by preparative HPLC to give the title compound (44 mg) as white crystals.

MS (ESI) m/z: 430[M+H]
$^1$H-NMR(DMSO-d$_6$)δ(ppm): 1.29(2H, brs), 1.49-1.55 (2H, m), 2.38(3H, s), 2.60-2.65(2H, m), 3.19-3.32(4H, m), 4.46(2H, t, J=5.1 Hz), 7.01-7.08(2H, m), 7.15(1H, d, J=7.2 Hz), 7.25-7.29(3H, m), 7.40-7.51(4H, m).

Example 9

Synthesis of 2-amino-2-{2-[2'-fluoro-4'-(4-fluorophenylthio)biphenyl-4-yl]ethyl}propane-1,3-diol

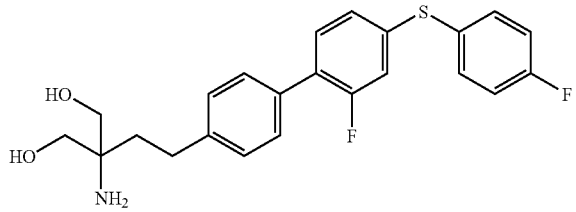

A solution of N-{5-[2-(4'-bromo-2'-fluorobiphenyl-4-yl) ethyl]-2,2-dimethyl-1,3-dioxan-5-yl}acetamide (225 mg) of Reference Example 10, 4-fluorobenzenethiol (64 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 6 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the obtained residue was dissolved in ethanol (4 mL). Concentrated hydrochloric acid (2 mL) was added, and the mixture was stirred at 80° C. for 4 hr. The reaction mixture was concentrated, aqueous potassium carbonate solution was added to the residue, and the precipitated crystals were collected by filtration. The crude crystals were purified by preparative HPLC to give the title compound (24 mg) as white crystals.

MS(ESI)m/z: 416[M+H]
$^1$H-NMR(DMSO-d$_6$)δ(ppm): 1.29(2H, brs), 1.49-1.55 (2H, m), 2.60-2.66(2H, m), 3.19-3.29(4H, m), 4.46(2H, t, J=5.2 Hz), 7.07-7.26(2H, m), 7.29-7.60(9H, m).

Example 10

Synthesis of 2-amino-2-{2-[4'-(4-chlorophenylthio)-2'-fluorobiphenyl-4-yl]ethyl}propane-1,3-diol

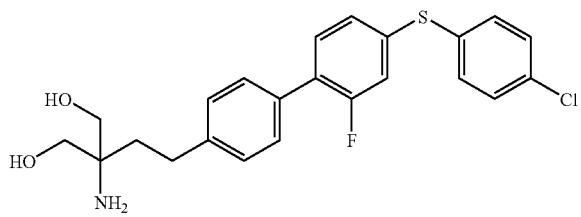

A solution of N-{5-[2-(4'-bromo-2'-fluorobiphenyl-4-yl)ethyl]-2,2-dimethyl-1,3-dioxan-5-yl}acetamide (225 mg) of Reference Example 10, 4-chlorobenzenethiol (72 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 7 hr under a nitrogen atmosphere. Tris(dibenzylideneacetone)dipalladium(0) chloroform adduct (12.9 mg) and Xantphos (14.9 mg) were added to the reaction mixture, and the mixture was further heated under reflux for 9 hr. Water was added to the reaction mixture, and the mixture was extracted with ethyl acetate. The extract was washed with saturated brine, and dried over anhydrous sodium sulfate. The solvent was evaporated under reduced pressure, and the obtained residue was dissolved in ethanol (4 mL). Concentrated hydrochloric acid (2 mL) was added, and the mixture was stirred at 80° C. for 4 hr. The reaction mixture was concentrated, aqueous potassium carbonate solution was added to the residue, and the precipitated crystals were collected by filtration. The crude crystals were purified by preparative HPLC to give the title compound (19 mg) as white crystals.

MS(ESI)m/z: 432[M+H]

$^1$H-NMR(DMSO-$d_6$)δ(ppm): 1.31(2H, brs), 1.50-1.55 (2H, m), 2.61-2.66(2H, m), 3.20-3.28(4H, m), 4.46(2H, brs), 7.16-7.30(4H, m), 7.43-7.55(7H, m).

Example 11

Synthesis of 2-amino-2-{2-[2'-fluoro-4'-(5-methyl-2-thienylthio)biphenyl-4-yl]ethyl}propane-1,3-diol

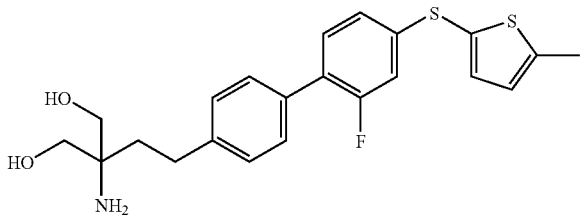

A solution of N-{5-[2-(4'-bromo-2'-fluorobiphenyl-4-yl)ethyl]-2,2-dimethyl-1,3-dioxan-5-yl}acetamide (225 mg) of Reference Example 10, 5-methylthiophene-2-thiol (65 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 6 hr under a nitrogen atmosphere. Tris(dibenzylideneacetone)dipalladium(0) chloroform adduct (12.9 mg) and Xantphos (14.9 mg) were added to the reaction mixture, and the mixture was further heated under reflux for 8 hr. Water was added to the reaction mixture, and the mixture was extracted with ethyl acetate. The extract was washed with saturated brine, and dried over anhydrous sodium sulfate. The solvent was evaporated under reduced pressure, and the obtained residue was dissolved in ethanol (4 mL). Concentrated hydrochloric acid (2 mL) was added, and the mixture was stirred at 80° C. for 4 hr. The reaction mixture was concentrated, aqueous potassium carbonate solution was added to the residue, and the precipitated crystals were collected by filtration. The crude crystals were purified by preparative HPLC to give the title compound (51 mg) as brown crystals.

MS(ESI)m/z: 418[M+H]

$^1$H-NMR(DMSO-$d_6$)δ(ppm): 1.33(2H, brs), 1.49-1.55 (2H, m), 2.50(3H, s), 2.60-2.65(2H, m), 3.20-3.24(4H, m), 4.46(2H, brs), 6.94(1H, d, J=3.3 Hz), 7.00-7.05(2H, m), 7.26-7.49(6H, m).

Example 12

Synthesis of 2-amino-2-{2-[2'-fluoro-4'-(4-trifluoromethylphenylthio)biphenyl-4-yl]ethyl}propane-1,3-diol

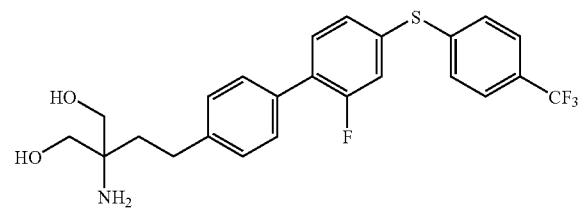

A solution of N-{5-[2-(4'-bromo-2'-fluorobiphenyl-4-yl)ethyl]-2,2-dimethyl-1,3-dioxan-5-yl}acetamide (225 mg) of Reference Example 10, 4-(trifluoromethyl)benzenethiol (89 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 7 hr under a nitrogen atmosphere. Tris(dibenzylideneacetone)dipalladium(0) chloroform adduct (12.9 mg) and Xantphos (14.9 mg) were added to the reaction mixture, and the mixture was further heated under reflux for 8 hr. Water was added to the reaction mixture, and the mixture was extracted with ethyl acetate. The extract was washed with saturated brine, and dried over anhydrous sodium sulfate. The solvent was evaporated under reduced pressure, and the obtained residue was dissolved in ethanol (4 mL). Concentrated hydrochloric acid (2 mL) was added, and the mixture was stirred at 80° C. for 4 hr. The reaction mixture was concentrated, aqueous potassium carbonate solution was added to the residue, and the precipitated crystals were collected by filtration. The crude crystals were purified by preparative HPLC to give the title compound (25 mg) as white crystals.

MS(ESI)m/z: 466[M+H]

$^1$H-NMR(DMSO-d$_6$)δ(ppm): 1.32(2H, brs), 1.51-1.56 (2H, m), 2.62-2.68(2H, m), 3.22-3.29(4H, m), 4.48(2H, brs), 7.30-7.38(3H, m), 7.44-7.52(5H, m), 7.61(1H, t, J=8.2 Hz), 7.74(2H, d, J=8.4 Hz).

Example 13

2-amino-2-{2-[4'-(2,4-dimethylphenylthio)-2'-fluorobiphenyl-4-yl]ethyl}propane-1,3-diol (13-1) Synthesis of N-(5-{2-[4'-(2,4-dimethylphenylthio)-2'-fluorobiphenyl-4-yl]ethyl}-2,2-dimethyl-1,3-dioxan-5-yl)acetamide

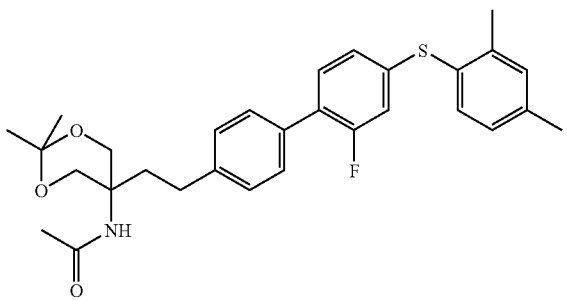

A solution of N-{5-[2-(4'-bromo-2'-fluorobiphenyl-4-yl)ethyl]-2,2-dimethyl-1,3-dioxan-5-yl}acetamide (225 mg) of Reference Example 10, 2,4-dimethylbenzenethiol (69 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 7 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.26 g) as a colorless oil.

$^1$H-NMR(CDCl$_3$)δ(ppm): 1.43(6H, s), 2.01(3H, s), 2.07-2.12(2H, m), 2.35(3H, s), 2.36(3H, s), 2.54-2.60(2H, m), 3.69(2H, d, J=12.0 Hz), 3.99(2H, d, J=12.0 Hz), 5.79(1H, s), 6.78(1H, dd, J=1.8, 11.4 Hz), 6.91(1H, dd, J=1.8, 8.1 Hz), 7.04(1H, d, J=7.8 Hz), 7.14(1H, s), 7.21-7.28(3H, m), 7.38-7.41(3H, m).

(13-2) Synthesis of 2-amino-2-{2-[4'-(2,4-dimethylphenylthio)-2'-fluorobiphenyl-4-yl]ethyl}propane-1,3-diol

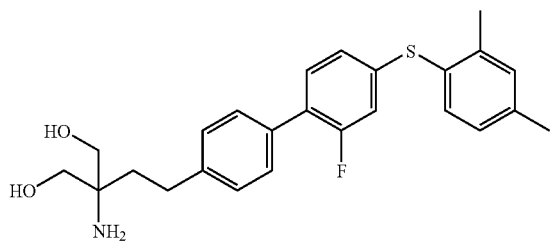

N-(5-{2-[4'-(2,4-Dimethylphenylthio)-2'-fluorobiphenyl-4-yl]ethyl}-2,2-dimethyl-1,3-dioxan-5-yl)acetamide (0.26 g) was dissolved in ethanol (4 mL), concentrated hydrochloric acid (2 mL) was added, and the mixture was stirred at 80° C. for 4 hr. The reaction mixture was concentrated, aqueous potassium carbonate solution was added to the residue, and the precipitated crystals were collected by filtration to give the title compound (205 mg) as white crystals.

MS(ESI)m/z: 426[M+H]

$^1$H-NMR(DMSO-d$_6$)δ(ppm): 1.40-1.82(4H, m), 2.32(3H, s), 2.33(3H, s), 2.59-2.65(2H, m), 3.21-3.29(4H, m), 4.48 (2H, brs), 6.88(1H, d, J=3.7 Hz), 6.92(1H, s), 7.13(1H, d, J=7.8 Hz), 7.27(3H, d, J=7.4 Hz), 7.39-7.49(4H, m).

Example 14

2-amino-2-{2-[2'-fluoro-4'-(3-methoxyphenylthio)biphenyl-4-yl]ethyl}propane-1,3-diol (14-1) Synthesis of N-(5-{2-[2'-fluoro-4'-(3-methoxyphenylthio)biphenyl-4-yl]ethyl}-2,2-dimethyl-1,3-dioxan-5-yl)acetamide

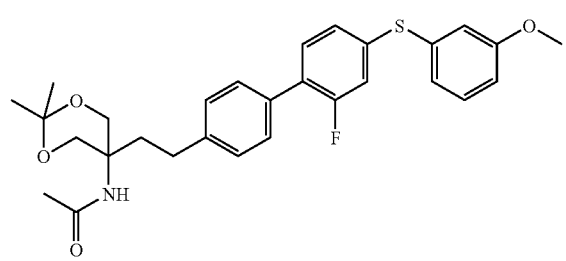

A solution of N-{5-[2-(4'-bromo-2'-fluorobiphenyl-4-yl)ethyl]-2,2-dimethyl-1,3-dioxan-5-yl}acetamide (225 mg) of Reference Example 10, 3-methoxybenzenethiol (70 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 1 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.26 g) as yellow crystals.

$^1$H-NMR(CDCl$_3$)δ(ppm): 1.43(6H, s), 2.02(3H, s), 2.08-2.13(2H, m), 2.55-2.61(2H, m), 3.70(2H, d, J=11.7 Hz), 3.79 (3H, s), 4.00(2H, d, J=12.0 Hz), 5.76(1H, s), 6.80-6.88(1H, m), 6.98-7.14(4H, m), 7.23-7.33(4H, m), 7.42(2H, dd, J=1.5, 8.1 Hz).

(14-2) Synthesis of 2-amino-2-{2-[2'-fluoro-4'-(3-methoxyphenylthio)biphenyl-4-yl]ethyl}propane-1,3-diol

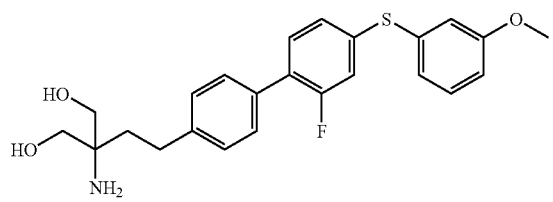

N-(5-{2-[2'-Fluoro-4'-(3-methoxyphenylthio)biphenyl-4-yl]ethyl}-2,2-dimethyl-1,3-dioxan-5-yl)acetamide (0.26 g) was dissolved in ethanol (4 mL), concentrated hydrochloric acid (2 mL) was added, and the mixture was stirred at 75° C. for 7 hr. The reaction mixture was concentrated, aqueous potassium carbonate solution was added to the residue, and the precipitated crystals were collected by filtration to give the title compound (205 mg) as brown crystals.

MS(ESI)m/z: 428[M+H]

$^1$H-NMR(DMSO-$d_6$)δ(ppm): 1.55-1.61(2H, m), 2.61-2.66 (2H, m), 3.26-3.33(4H, m), 3.76(3H, s), 4.64(2H, brs), 6.92-7.08(3H, m), 7.15-7.58(8H, m).

Example 15

2-amino-2-{2-[2'-fluoro-4'-(4-methoxyphenylthio)biphenyl-4-yl]ethyl}propane-1,3-diol hydrochloride (15-1) Synthesis of N-(5-{2-[2'-fluoro-4'-(4-methoxyphenylthio)biphenyl-4-yl]ethyl}-2,2-dimethyl-1,3-dioxan-5-yl)acetamide

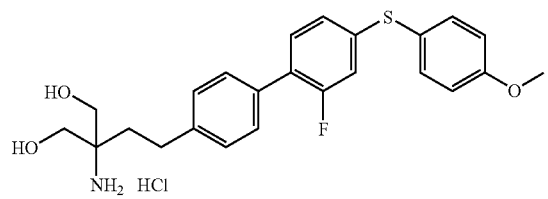

A solution of N-{5-[2-(4'-bromo-2'-fluorobiphenyl-4-yl)ethyl]-2,2-dimethyl-1,3-dioxan-5-yl}acetamide (170 mg) of Reference Example 10, 4-methoxybenzenethiol (53 mg), diisopropylethylamine (98 mg), tris(dibenzylideneacetone)dipalladium(0) chloroform adduct (9.8 mg) and 4,5-bis(diphenylphosphino)-9,9-dimethylxanthene (Xantphos) (11.2 mg) in 1,4-dioxane (1.5 mL) was heated under reflux for 9 hr under a nitrogen atmosphere. 4-Methoxybenzenethiol (11 mg), tris(dibenzylideneacetone)dipalladium(0) chloroform adduct (3.9 mg) and Xantphos (4.4 mg) were added to the reaction mixture, and the mixture was further heated under reflux for 9 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.22 g) as brown crystals.

$^1$H-NMR(CDCl$_3$)δ(ppm): 1.43(6H, s), 2.02(3H, s), 2.07-2.12(2H, m), 2.54-2.60(2H, m), 3.69(2H, d, J=11.9 Hz), 3.85 (3H, s), 3.99(2H, d, J=11.9 Hz), 5.74(1H, s), 6.80-6.86(1H, m), 6.93-6.98(3H, m), 7.21-7.26(3H, m), 7.40(2H, dd, J=1.3, 8.1 Hz), 7.46-7.49(2H, m).

(15-2) Synthesis of 2-amino-2-{2-[2'-fluoro-4'-(4-methoxyphenylthio)biphenyl-4-yl]ethyl}propane-1,3-diol hydrochloride

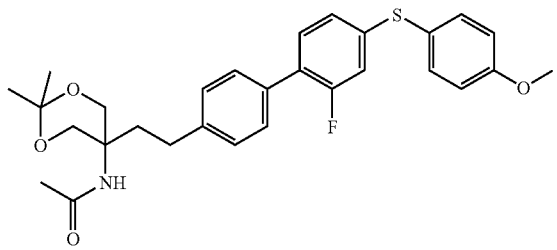

N-(5-{2-[2'-Fluoro-4'-(4-methoxyphenylthio)biphenyl-4-yl]ethyl}-2,2-dimethyl-1,3-dioxan-5-yl)acetamide (0.22 g) was dissolved in ethanol (4 mL), concentrated hydrochloric acid (2 mL) was added, and the mixture was stirred at 75° C. for 4 hr. The reaction mixture was concentrated to dryness, and the residual solid was suspended in ethyl acetate and collected by filtration to give the title compound (39 mg) as brown crystals.

MS(ESI)m/z: 428[M+H]

$^1$H-NMR(DMSO-$d_6$)δ(ppm): 1.75-1.81(2H, m), 2.59-2.65 (2H, m), 3.50(4H, d, J=4.3 Hz), 3.80(3H, s), 5.36(2H, brs), 6.92-6.96(2H, m), 7.05(2H, d, J=6.6 Hz), 7.28(2H, d, J=8.2 Hz), 7.41-7.43(3H, m), 7.50(2H, d, J=8.8 Hz), 7.69(3H, brs).

Example 16

2-amino-2-{2-[4'-(3,4-dimethylphenylthio)-2'-fluorobiphenyl-4-yl]ethyl}propane-1,3-diol hydrochloride (16-1) Synthesis of N-(5-{2-[4'-(3,4-dimethylphenylthio)-2'-fluorobiphenyl-4-yl]ethyl}-2,2-dimethyl-1,3-dioxan-5-yl)acetamide

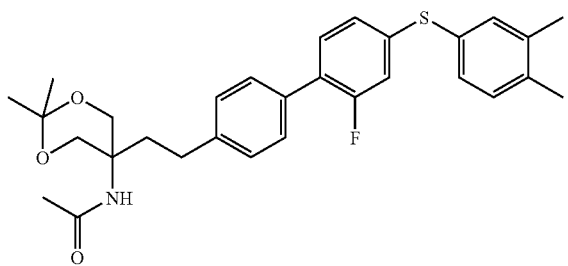

A solution of N-{5-[2-(4'-bromo-2'-fluorobiphenyl-4-yl)ethyl]-2,2-dimethyl-1,3-dioxan-5-yl}acetamide (170 mg) of Reference Example 10, 3,4-dimethylbenzenethiol (52 mg), diisopropylethylamine (98 mg), tris(dibenzylideneacetone)

dipalladium(0) chloroform adduct (9.8 mg) and 4,5-bis(diphenylphosphino)-9,9-dimethylxanthene (Xantphos) (11.2 mg) in 1,4-dioxane (1.5 mL) was heated under reflux for 9 hr under a nitrogen atmosphere. 3,4-Dimethylbenzenethiol (10 mg), tris(dibenzylideneacetone)dipalladium(0) chloroform adduct (3.9 mg) and Xantphos (4.4 mg) were added to the reaction mixture, and the mixture was further heated under reflux for 9 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.23 g) as pale-yellow crystals.

$^1$H-NMR(CDCl$_3$)δ(ppm): 1.43(6H, s), 2.02(3H, s), 2.07-2.12(2H, m), 2.26(3H, s), 2.28(3H, s), 2.55-2.60(2H, m), 3.69(2H, d, J=12.0 Hz), 3.99(2H, d, J=11.7 Hz), 5.76(1H, s), 6.92(1H, d, J=11.1 Hz), 7.02(1H, dd, J=1.8, 9.9 Hz), 7.05-7.29(6H, m), 7.41(2H, dd, J=1.5, 8.1 Hz).

(16-2) Synthesis of 2-amino-2-{2-[4'-(3,4-dimethylphenylthio)-2'-fluorobiphenyl-4-yl]ethyl}propane-1,3-diol hydrochloride

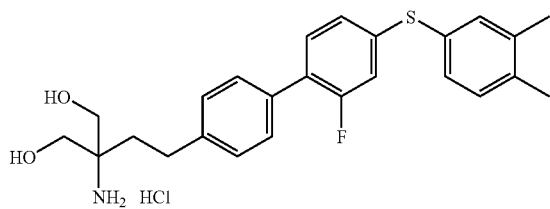

N-(5-{2-[4'-(3,4-Dimethylphenylthio)-2'-fluorobiphenyl-4-yl]ethyl}-2,2-dimethyl-1,3-dioxan-5-yl)acetamide (0.23 g) was dissolved in ethanol (4 mL), concentrated hydrochloric acid (2 mL) was added, and the mixture was stirred at 75° C. for 4 hr. The reaction mixture was concentrated to dryness, and the residual solid was suspended in ethyl acetate and collected by filtration to give the title compound (141 mg) as white crystals.

MS(ESI)m/z: 426[M+H]

$^1$H-NMR(DMSO-d$_6$)δ(ppm): 1.76-1.82(2H, m), 2.23(3H, s), 2.24(3H, s), 2.60-2.66(2H, m), 3.51(4H, d, J=4.4 Hz), 5.38(2H, brs), 7.01(2H, d, J=9.9 Hz), 7.24-7.33(5H, m), 7.41-7.46(3H, m), 7.77(3H, brs).

Example 17

2-amino-2-{2-[2'-fluoro-4'-(4-isopropylphenylthio)biphenyl-4-yl]ethyl}propane-1,3-diol hydrochloride (17-1) Synthesis of N-(5-{2-[2'-fluoro-4'-(4-isopropylphenylthio)biphenyl-4-yl]ethyl}-2,2-dimethyl-1,3-dioxan-5-yl)acetamide

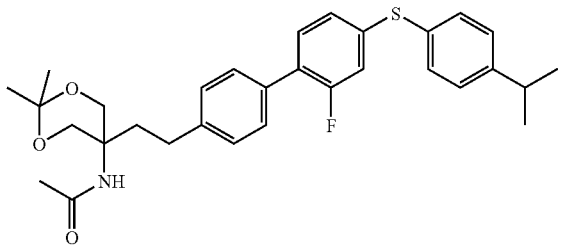

A solution of N-{5-[2-(4'-bromo-2'-fluorobiphenyl-4-yl)ethyl]-2,2-dimethyl-1,3-dioxan-5-yl}acetamide (170 mg) of Reference Example 10, 4-isopropylbenzenethiol (57 mg), diisopropylethylamine (98 mg), tris(dibenzylideneacetone)dipalladium(0) chloroform adduct (9.8 mg) and 4,5-bis(diphenylphosphino)-9,9-dimethylxanthene (Xantphos) (11.2 mg) in 1,4-dioxane (1.5 mL) was heated under reflux for 9 hr under a nitrogen atmosphere. 4-Isopropylbenzenethiol (12 mg), tris(dibenzylideneacetone)dipalladium(0) chloroform adduct (3.9 mg) and Xantphos (4.4 mg) were added to the reaction mixture, and the mixture was further heated under reflux for 9 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.24 g) as a colorless oil.

$^1$H-NMR(CDCl$_3$)δ(ppm): 1.27(6H, d, J=6.9 Hz), 1.43(6H, s), 2.02(3H, s), 2.07-2.13(2H, m), 2.55-2.60(2H, m), 2.93(1H, sept, J=6.9 Hz), 3.69(2H, d, J=12.0 Hz), 4.00(2H, d, J=12.0 Hz), 5.76(1H, s), 6.96(1H, dd, J=1.8, 11.1 Hz), 7.05(1H, dd, J=1.8, 8.1 Hz), 7.22-7.32(5H, m), 7.41(4H, d, J=8.1 Hz).

(17-2) Synthesis of 2-amino-2-{2-[2'-fluoro-4'-(4-isopropylphenylthio)biphenyl-4-yl]ethyl}propane-1,3-diol hydrochloride

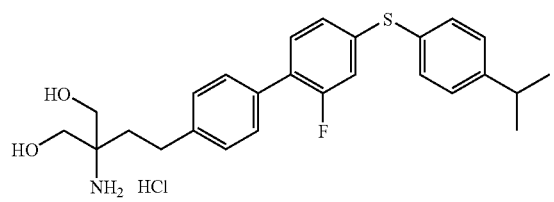

N-(5-{2-[2'-Fluoro-4'-(4-isopropylphenylthio)biphenyl-4-yl]ethyl}-2,2-dimethyl-1,3-dioxan-5-yl)acetamide (0.24 g) was dissolved in ethanol (4 mL), concentrated hydrochloric acid (2 mL) was added, and the mixture was stirred at 75° C. for 4 hr. The reaction mixture was concentrated to dryness, and the residual solid was suspended in ethyl acetate and collected by filtration to give the title compound (141 mg) as white crystals.

MS(ESI)m/z: 440[M+H]

$^1$H-NMR(DMSO-d$_6$)δ(ppm): 1.20(6H, d, J=6.9 Hz), 1.77-1.83(2H, m), 2.61-2.66(2H, m), 2.91(1H, sept, J=6.9 Hz), 3.52(4H, d, J=4.6 Hz), 5.39(2H, t, J=4.6 Hz), 7.05-7.09(2H, m), 7.28-7.35(4H, m), 7.41-7.46(5H, m), 7.83(3H, brs).

Example 18

2-amino-2-{2-[3-chloro-2'-fluoro-4'-(4-methylphenylthio)biphenyl-4-yl]ethyl}propane-1,3-diol (18-1) Synthesis of N-[1,1-bis(acetoxymethyl)-3-[3-chloro-2'-fluoro-4'-(4-methylphenylthio)biphenyl-4-yl]propyl]acetamide

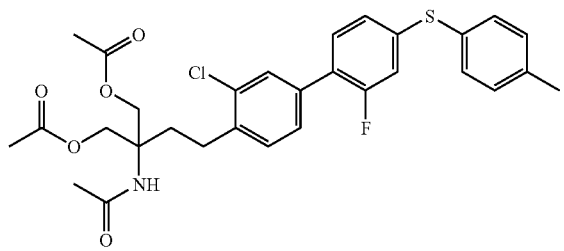

A solution of N-[1,1-bis(acetoxymethyl)-3-(4'-bromo-3-chloro-2'-fluorobiphenyl-4-yl)propyl]acetamide (264 mg) of Reference Example 23, 4-methylbenzenethiol (62 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 9 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.24 g) as pale-yellow crystals.

$^1$H-NMR(CDCl$_3$)δ(ppm): 2.00(3H, s), 2.10(6H, s), 2.17-2.22(2H, m), 2.38(3H, s), 2.73-2.79(2H, m), 4.39(4H, s), 5.77(1H, s), 6.91(1H, dd, J=1.8, 11.4 Hz), 7.02(1H, dd, J=1.5, 9.9 Hz), 7.20-7.32(5H, m), 7.40(2H, d, J=8.1 Hz), 7.48(1H, s).

(18-2) Synthesis of 2-amino-2-{2-[3-chloro-2'-fluoro-4'-(4-methylphenylthio)biphenyl-4-yl]ethyl}propane-1,3-diol

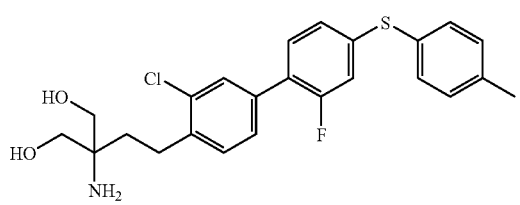

N-[1,1-Bis(acetoxymethyl)-3-[3-chloro-2'-fluoro-4'-(4-methylphenylthio)biphenyl-4-yl]propyl]acetamide (0.24 g) was dissolved in ethanol (4 mL), concentrated hydrochloric acid (2 mL) was added, and the mixture was stirred at 75° C. for 3 hr. The reaction mixture was concentrated, aqueous potassium carbonate solution was added to the residue, and the precipitated crystals were collected by filtration. The crude crystals were purified by preparative HPLC to give the title compound (106 mg) as white crystals.

MS(ESI)m/z: 446[M+H]

$^1$H-NMR(DMSO-d$_6$)δ(ppm): 1.29(2H, brs), 1.47-1.53 (2H, m), 2.35(3H, s), 2.72-2.77(2H, m), 3.21-3.30(4H, m), 4.49(2H, t, J=4.7 Hz), 7.01-7.06(2H, m), 7.30(2H, d, J=8.0 Hz), 7.38-7.52(6H, m).

Example 19

2-amino-2-{2-[2'-fluoro-4'-(4-methylphenoxy)biphenyl-4-yl]ethyl}propane-1,3-diol (19-1) Synthesis of N-[1,1-bis(acetoxymethyl)-3-(2'-fluoro-4'-hydroxybiphenyl-4-yl)propyl]acetamide

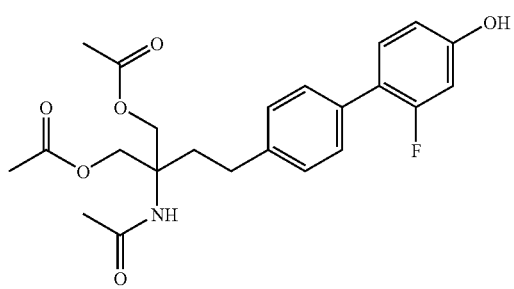

A mixed solution of N-[1,1-bis(acetoxymethyl)-3-[4-(5,5-dimethyl-1,3,2-dioxaborinan-2-yl)phenyl]propyl]acetamide (867 mg) of Reference Example 9, 1-benzyloxy-4-bromo-3-fluorobenzene (674 mg), sodium hydrogen carbonate (1.01 g) and tetrakistriphenylphosphine palladium (46 mg) in 1,2-dimethoxyethane (15 mL)-water (5 mL) was stirred at 65° C. for 5 hr. The reaction mixture was extracted with ethyl acetate. The extract was washed with saturated brine, and dried over anhydrous sodium sulfate. The solvent was evaporated under reduced pressure. To a solution of the residue in methanol (30 mL) were added palladium carbon (10%, 0.3 g) and ammonium formate (517 mg), and the mixture was stirred at room temperature for 6 hr under a nitrogen atmosphere. The reaction mixture was filtered through celite, and the solvent was evaporated under reduced pressure. Water was added to the residue, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.56 g) as white amorphous crystals.

$^1$H-NMR(CDCl$_3$)δ(ppm): 2.04(3H, s), 2.11(6H, s), 2.29-2.34(2H, m), 2.61-2.67(2H, m), 4.38(4H, s), 6.06(1H, s), 6.64-6.71(2H, m), 7.10-7.27(3H, m), 7.38(2H, dd, J=1.2, 8.1 Hz), 8.42(1H, brs).

(19-2) Synthesis of N-{1,1-bis(acetoxymethyl)-3-[2'-fluoro-4'-(4-methylphenoxy)biphenyl-4-yl]propyl}acetamide

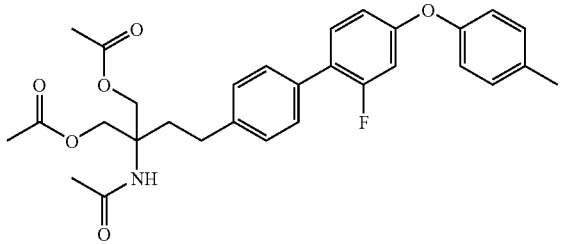

A solution of N-[1,1-bis(acetoxymethyl)-3-(2'-fluoro-4'-hydroxybiphenyl-4-yl)propyl]acetamide (278 mg), 4-methylphenylboronic acid (175 mg), copper(II) acetate (117 mg), pyridine (255 mg) and molecular sieves 4A (500 mg) in methylene chloride (5 mL) was stirred at room temperature for 9 hr. 2% Aqueous citric acid solution (100 mL) was added to the reaction mixture, and the mixture was extracted with chloroform. The extract was washed with saturated brine, and dried over anhydrous sodium sulfate. The solvent was evaporated under reduced pressure, and the residue was purified by silica gel column chromatography to give the title compound (0.26 g) as white crystals.

$^1$H-NMR(CDCl$_3$)δ(ppm): 1.97(3H, s), 2.09(6H, s), 2.22-2.28(2H, m), 2.35(3H, s), 2.63-2.68(2H, m), 4.37(4H, s), 5.80(1H, s), 6.72-6.79(2H, m), 6.97(2H, d, J=8.4 Hz), 7.16-7.44(7H, m).

(19-3) Synthesis of 2-amino-2-{2-[2'-fluoro-4'-(4-methylphenoxy)biphenyl-4-yl]ethyl}propane-1,3-diol

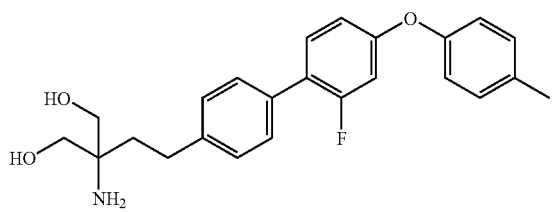

N-{1,1-Bis(acetoxymethyl)-3-[2'-fluoro-4'-(4-methylphenoxy)biphenyl-4-yl]propyl}acetamide (0.26 g) was dissolved in methanol (10 mL), 1M aqueous lithium hydroxide solution (10 mL) was added, and the mixture was refluxed with stirring for 2 hr. The reaction mixture was concentrated, and the precipitated crystals were collected by filtration. The crude crystals were purified by preparative HPLC to give the title compound (59 mg) as white crystals.

MS(ESI)m/z: 396[M+H]

$^1$H-NMR(DMSO-d$_6$)δ(ppm): 1.72-1.78(2H, m), 2.36(3H, s), 2.67-2.72(2H, m), 3.54(2H, d, J=10.5 Hz), 3.63(2H, d, J=10.8 Hz), 6.72-6.83(2H, m), 6.98(2H, d, J=8.7 Hz), 7.18(2H, d, J=8.4 Hz), 7.25-7.28(2H, m), 7.34(1H, t, J=8.6 Hz), 7.44(2H, dd, J=1.5, 8.1 Hz).

Example 20

(5-{4-[3-amino-4-hydroxy-3-(hydroxymethyl)butyl]phenyl}-2-thienyl)(4-methylphenyl)ketone (20-1) Synthesis of N-(5-{2-[4-(5-formyl-2-thienyl)phenyl]ethyl}-2,2-dimethyl-1,3-dioxan-5-yl)acetamide

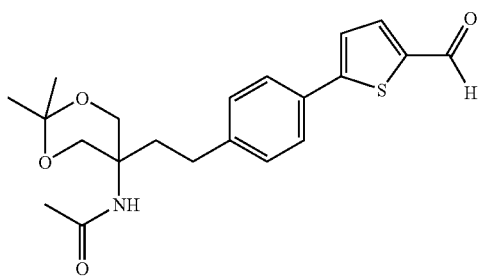

A mixed solution of N-{5-[2-(4-bromophenyl)ethyl]-2,2-dimethyl-1,3-dioxan-5-yl}acetamide (1.07 g) of Reference Example 5, 5-formyl-2-thiopheneboronic acid (0.56 g), sodium hydrogen carbonate (1.51 g), palladium(II) acetate (33.7 mg) and 2-(di-t-butylphosphino)biphenyl (89.5 mg) in 1,2-dimethoxyethane (12 mL)-water (4 mL) was stirred at 65° C. for 9 hr under a nitrogen atmosphere. The reaction mixture was extracted with ethyl acetate. The extract was washed with saturated brine, and dried over anhydrous sodium sulfate. The solvent was evaporated under reduced pressure, and the residue was purified by silica gel column chromatography to give the title compound (0.25 g) as brown crystals.

$^1$H-NMR(CDCl$_3$)δ(ppm): 1.44(6H, s), 2.05(3H, s), 2.08-2.12(2H, m), 2.55-2.61(2H, m), 3.70(2H, d, J=11.7 Hz), 3.98(2H, d, J=11.7 Hz), 5.78(1H, s), 7.25(2H, d, J=8.7 Hz), 7.37(1H, d, J=3.3 Hz), 7.58(2H, d, J=8.4 Hz), 7.73(1H, d, J=3.9 Hz), 9.88(1H, s).

(20-2) Synthesis of N-{5-[2-(4-{5-[hydroxy(4-methylphenyl)methyl]-2-thienyl}phenyl)ethyl]-2,2-dimethyl-1,3-dioxan-5-yl}acetamide

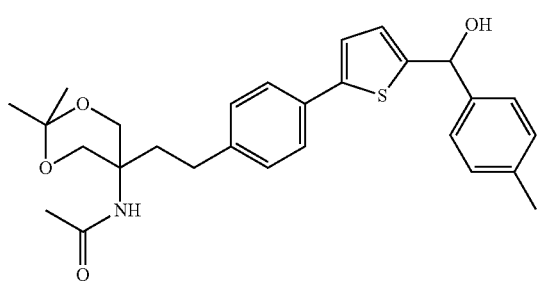

To a solution of N-(5-{2-[4-(5-formyl-2-thienyl)phenyl]ethyl}-2,2-dimethyl-1,3-dioxan-5-yl)acetamide (0.25 g) in tetrahydrofuran (20 mL) was added dropwise a solution (1 mol/L, 1.36 mL) of p-tolylmagnesium bromide in tetrahydrofuran at 0° C. under a nitrogen atmosphere, and the mixture was stirred at the same temperature for 1 hr. 0.5M Aqueous ammonium chloride solution (30 mL) was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.35 g) as a brown oil.

$^1$H-NMR(CDCl$_3$)δ(ppm): 1.42(6H, s), 2.02-2.09(5H, m), 2.36(3H, s), 2.50-2.56(2H, m), 3.65-3.69(3H, m), 3.97(2H, d, J=12.0 Hz), 5.74(1H, s), 6.00(1H, d, J=3.6 Hz), 6.83(1H, d, J=3.6 Hz), 7.08(1H, d, J=3.6 Hz), 7.13-7.26(4H, m), 7.37(2H, d, J=8.1 Hz), 7.44(2H, d, J=8.1 Hz).

(20-3) Synthesis of N-[2,2-dimethyl-5-(2-{4-[5-(4-methylbenzoyl)-2-thienyl]phenyl}ethyl)-1,3-dioxan-5-yl]acetamide

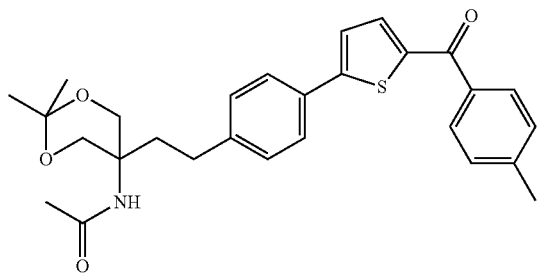

To a solution of N-{5-[2-(4-{5-[hydroxy(4-methylphenyl)methyl]-2-thienyl}phenyl)ethyl]-2,2-dimethyl-1,3-dioxan-5-yl}acetamide (0.35 g) in methylene chloride (5 mL) were added tri(p-tolyl)bismuth dichloride (393 mg) and 1,8-diazabicyclo[5.4.0]undec-7-ene (108 mg) at room temperature, and the mixture was stirred at the same temperature for 2 hr. Chloroform was added to the reaction mixture, and the mixture was washed with saturated brine and dried over anhydrous sodium sulfate. The solvent was evaporated under reduced pressure, and the residue was purified by silica gel column chromatography to give the title compound (0.22 g) as brown crystals.

$^1$H-NMR(CDCl$_3$)δ(ppm): 1.44(6H, s), 2.04(3H, s), 2.06-2.12(2H, m), 2.45(3H, s), 2.55-2.60(2H, m), 3.70(2H, d, J=12.0 Hz), 3.98(2H, d, J=12.0 Hz), 5.83(1H, s), 7.22-7.31 (5H, m), 7.57-7.60(3H, m), 7.79(2H, d, J=8.1 Hz).

(20-4) Synthesis of (5-{4-[3-amino-4-hydroxy-3-(hydroxymethyl)butyl]phenyl}-2-thienyl)(4-methylphenyl)ketone

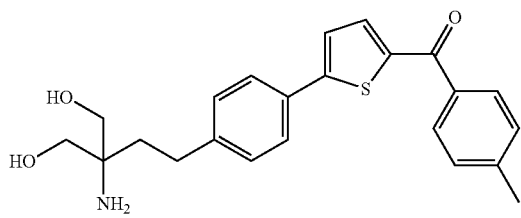

N-[2,2-Dimethyl-5-(2-{4-[5-(4-methylbenzoyl)-2-thienyl]phenyl}ethyl)-1,3-dioxan-5-yl]acetamide (0.22 g) was dissolved in ethanol (4 mL), concentrated hydrochloric acid (2 mL) was added, and the mixture was stirred at 80° C. for 4 hr. The reaction mixture was concentrated, aqueous potassium carbonate solution was added to the residue, and the precipitated crystals were collected by filtration to give the title compound (163 mg) as brown crystals.

MS(ESI)m/z: 396[M+H]

$^1$H-NMR(DMSO-d$_6$)δ(ppm): 1.61-1.67(2H, m), 2.42(3H, s), 2.62-2.68(2H, m), 3.32(4H, brs), 4.83(4H, brs), 7.32(2H, t, J=8.1 Hz), 7.39(2H, t, J=7.8 Hz), 7.63(1H, d, J=4.2 Hz), 7.71-7.79(5H, m).

Example 21

2-amino-4-[2'-fluoro-4'-(4-methylphenylthio)biphenyl-4-yl]-2-methylbutanol hydrochloride (21-1) Synthesis of 2-acetamide-4-[2'-fluoro-4'-(4-methylphenylthio)biphenyl-4-yl]-2-methylbutyl acetate

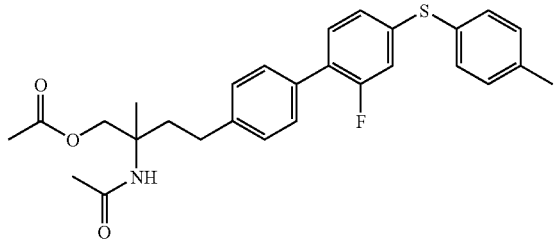

A solution of 2-acetamide-4-(4'-bromo-2'-fluorobiphenyl-4-yl)-2-methylbutyl acetate (218 mg) of Reference Example 29, 4-methylbenzenethiol (62 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 9 hr under a nitrogen atmosphere. 4-Methylbenzenethiol (12 mg), tris(dibenzylideneacetone)dipalladium(0) chloroform adduct (5.2 mg) and Xantphos (5.8 mg) were added to the reaction mixture, and the mixture was further heated under reflux for 6 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.28 g) as a yellow oil.

$^1$H-NMR(CDCl$_3$)δ(ppm): 1.39(3H, s), 1.92-2.04(1H, m), 1.92(3H, s), 2.10(3H, s), 2.18-2.34(1H, m), 2.38(3H, s), 2.64 (2H, t, J=8.4 Hz), 4.19(1H, d, J=11.1 Hz), 4.35(1H, d, J=11.1

Hz), 5.35(1H, s), 6.93(1H, dd, J=1.8, 11.1 Hz), 7.03(1H, dd, J=1.8, 8.1 Hz), 7.19-7.32(6H, m), 7.38-7.43(3H, m).

(21-2) Synthesis of 2-amino-4-[2'-fluoro-4'-(4-methylphenylthio)biphenyl-4-yl]-2-methylbutanol hydrochloride

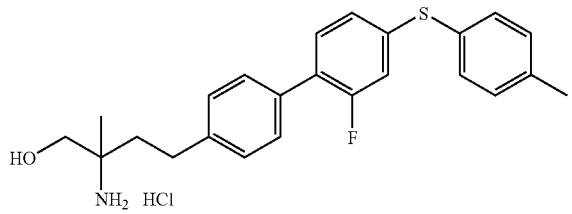

2-Acetamide-4-[2'-fluoro-4'-(4-methylphenylthio)biphenyl-4-yl]-2-methylbutyl acetate (0.28 g) was dissolved in ethanol (4 mL), concentrated hydrochloric acid (2 mL) was added, and the mixture was stirred at 75° C. for 4 hr. The reaction mixture was concentrated, and the precipitated crystals were collected by filtration to give the title compound (208 mg) as white crystals.

MS(ESI)m/z: 396[M+H]
$^1$H-NMR(DMSO-d$_6$)δ(ppm): 1.22(3H, s), 1.76-1.91(2H, m), 2.35(3H, s), 2.65(2H, t, J=8.7 Hz), 3.41-3.50(2H, m), 5.50(1H, s), 7.03-7.07(2H, m), 7.29-7.32(4H, m), 7.41-7.49 (5H, m), 7.84(3H, brs).

Example 22

2-amino-2-ethyl-4-[2'-fluoro-4'-(4-methylphenylthio)biphenyl-4-yl]butanol (22-1) Synthesis of 2-acetamide-2-ethyl-4-[2'-fluoro-4'-(4-methylphenylthio)biphenyl-4-yl]butyl acetate

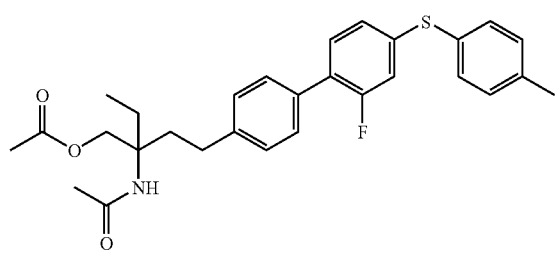

A solution of 2-acetamide-4-(4'-bromo-2'-fluorobiphenyl-4-yl)-2-ethylbutyl acetate (225 mg) of Reference Example 34, 4-methylbenzenethiol (62 mg), diisopropylethylamine (129 mg), tris(dibenzylideneacetone)dipalladium(0) chloroform adduct (12.9 mg) and 4,5-bis(diphenylphosphino)-9,9-dimethylxanthene (Xantphos) (14.9 mg) in 1,4-dioxane (2 mL) was heated under reflux for 9 hr under a nitrogen atmosphere. 4-Methylbenzenethiol (12 mg), tris(dibenzylideneacetone)dipalladium(0) chloroform adduct (5.2 mg) and Xantphos (5.8 mg) were added to the reaction mixture, and the mixture was further heated under reflux for 6 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.24 g) as a colorless oil.

$^1$H-NMR(CDCl$_3$)δ(ppm): 0.90(3H, t, J=7.5 Hz), 1.74-2.14 (4H, m), 1.94(3H, s), 2.10(3H, s), 2.38(3H, s), 2.60(2H, t, J=8.4 Hz), 4.30(1H, d, J=11.4 Hz), 4.35(1H, d, J=11.4 Hz), 5.22(1H, s), 6.94(1H, d, J=11.1 Hz), 7.02-7.05(1H, m), 7.19-7.43(9H, m).

(22-2) Synthesis of 2-amino-2-ethyl-4-[2'-fluoro-4'-(4-methylphenylthio)biphenyl-4-yl]butanol

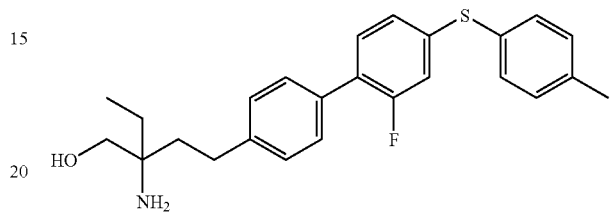

2-Acetamide-2-ethyl-4-[2'-fluoro-4'-(4-methylphenylthio)biphenyl-4-yl]butyl acetate (0.24 g) was dissolved in ethanol (4 mL), concentrated hydrochloric acid (2 mL) was added, and the mixture was stirred at 75° C. for 5 hr. The reaction mixture was poured into aqueous potassium carbonate solution. After partitioning and extraction with ethyl acetate, the extract was washed with saturated brine, and dried over anhydrous sodium sulfate. The solvent was evaporated under reduced pressure, and the residue was purified by preparative HPLC to give the title compound (92 mg) as white crystals.

MS(ESI)m/z: 410[M+H]
$^1$H-NMR(DMSO-d$_6$)δ(ppm): 0.82(3H, t, J=7.5 Hz), 1.21 (2H, brs), 1.34(2H, q, J=7.5 Hz), 1.50(2H, t, J=8.6 Hz), 2.35 (3H, s), 2.55-2.62(2H, m), 3.19(2H, d, J=4.5 Hz), 4.47(1H, t, J=4.5 Hz), 7.03-7.06(2H, m), 7.26-7.30(4H, m), 7.40-7.48 (5H, m).

Example 23

2-amino-4-[2'-fluoro-4'-(phenylthio)biphenyl-4-yl]-2-(phosphoryloxymethyl)butanol (23-1) Synthesis of 2-amino-2-[2-(4'-bromo-2'-fluorobiphenyl-4-yl)ethyl]propane-1,3-diol

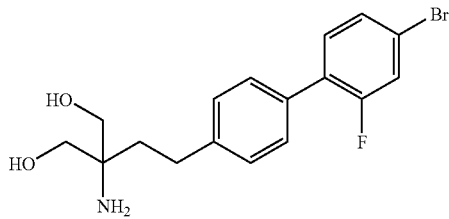

N-{5-[2-(4'-Bromo-2'-fluorobiphenyl-4-yl)ethyl]-2,2-dimethyl-1,3-dioxan-5-yl}acetamide (2.50 g) of Reference Example 10 was dissolved in ethanol (50 mL), concentrated hydrochloric acid (25 mL) was added, and the mixture was stirred at 80° C. for 4 hr. The reaction mixture was concentrated, and neutralized with 1M aqueous sodium hydroxide solution. The precipitated crystals were collected by filtration to give the title compound (1.36 g) as white crystals.

$^1$H-NMR(DMSO-d$_6$)δ(ppm): 1.28(2H, s), 1.50-1.55(2H, m), 2.61-2.67(2H, m), 3.25(4H, dd, J=10.8, 15.4 Hz), 4.49 (2H, brs), 7.30(2H, d, J=8.1 Hz), 7.43-7.52(4H, m), 7.64(1H, d, J=11.0 Hz).

(23-2) Synthesis of 4-[2-(4'-bromo-2'-fluorobiphenyl-4-yl)ethyl]-4-di(tert-butyl)phosphoryloxymethyl-2-methyl-2-oxazoline

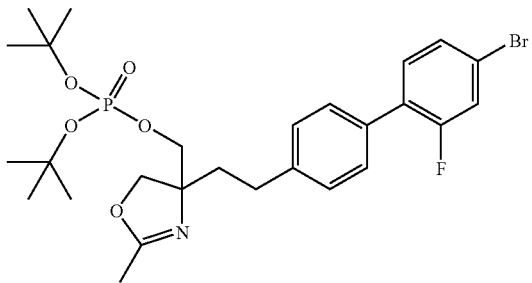

A solution of 2-amino-2-[2-(4'-bromo-2'-fluorobiphenyl-4-yl)ethyl]propane-1,3-diol (1.36 g), triethyl orthoacetate (0.72 g) and diisopropylethylamine (0.57 g) in N,N-dimethylformamide (5 mL) was stirred at 120° C. for 3 hr. Water was added to the reaction mixture, and the mixture was extracted with ethyl acetate. The extract was washed with saturated brine, and dried over anhydrous sodium sulfate. The solvent was evaporated under reduced pressure. To a solution of the residue in methylene chloride (37 mL) were added di-tert-butyl diisopropylphosphoramidite (1.54 g) and 1H-tetrazole (389 mg) at 0° C., and the mixture was stirred at room temperature for 2 hr. After cooling the reaction mixture to 0° C., a solution (5-6 mol/L, 2.22 mL) of tert-butylhydroperoxide in decane was added, and the mixture was stirred at the same temperature for 10 min. Aqueous sodium hydrogen carbonate solution was added to the reaction mixture, and the mixture was extracted with chloroform. The extract was washed with saturated brine, and dried over anhydrous sodium sulfate. The solvent was evaporated under reduced pressure, and the residue was purified by silica gel column chromatography to give the title compound (0.98 g) as a colorless oil.

$^1$H-NMR(CDCl$_3$)δ(ppm): 1.49(18H, s), 1.87-2.02(2H, m), 2.04(3H, s), 2.70(2H, t, J=8.6 Hz), 3.86-4.02(3H, m), 4.36 (1H, d, J=8.9 Hz), 7.26-7.44(7H, m).

(23-3) Synthesis of 4-{2-[2'-fluoro-4'-(phenylthio)biphenyl-4-yl]ethyl}-4-di(tert-butyl)phosphoryloxymethyl-2-methyl-2-oxazoline

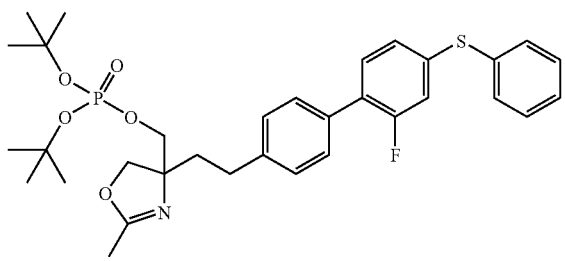

A solution of 4-[2-(4'-bromo-2'-fluorobiphenyl-4-yl)ethyl]-4-di(tert-butyl)phosphoryloxymethyl-2-methyl-2-oxazoline (201 mg), benzenethiol (42 mg), diisopropylethylamine (89 mg), tris(dibenzylideneacetone)dipalladium(0) chloroform adduct (17.8 mg) and 4,5-bis(diphenylphosphino)-9,9-dimethylxanthene (Xantphos) (19.9 mg) in 1,4-dioxane (2 mL) was heated under reflux for 15 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (103 mg) as a yellow oil.

$^1$H-NMR(CDCl$_3$)δ(ppm): 1.49(18H, s), 1.58-1.95(2H, m), 2.02(3H, s), 2.69(2H, t, J=8.6 Hz), 3.87-4.03(3H, m), 4.36 (1H, d, J=8.7 Hz), 7.04-7.12(2H, m), 7.24-7.47(10H, m).

(23-4) Synthesis of 2-amino-4-[2'-fluoro-4'-(phenylthio)biphenyl-4-yl]-2-(phosphoryloxymethyl)butanol

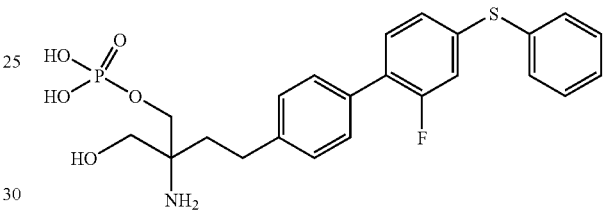

4-{2-[2'-Fluoro-4'-(phenylthio)biphenyl-4-yl]ethyl}-4-di(tert-butyl)phosphoryloxymethyl-2-methyl-2-oxazoline (103 mg) was dissolved in ethanol (5 mL), concentrated hydrochloric acid (1 mL) was added, and the mixture was stirred at 50° C. for 3 hr. Water (30 mL) was added to the reaction mixture, and the precipitated crystals were collected by filtration to give the title compound (41 mg) as white crystals.

MS(ESI)m/z: 478[M+H]

$^1$H-NMR(CD$_3$OD)δ(ppm): 1.94-2.05(2H, m), 2.68-2.80 (2H, m), 3.73(2H, s), 3.93-4.08(2H, m), 7.03-7.06(1H, m), 7.13(1H, d, J=8.4 Hz), 7.34-7.49(10H, m).

Example 24

2-amino-4-[2'-fluoro-4'-(4-methylphenylthio)biphenyl-4-yl]-2-(phosphoryloxymethyl)butanol (24-1) Synthesis of 4-{2-[2'-fluoro-4'-(4-methylphenylthio)biphenyl-4-yl]ethyl}-4-di(tert-butyl)phosphoryloxymethyl-2-methyl-2-oxazoline

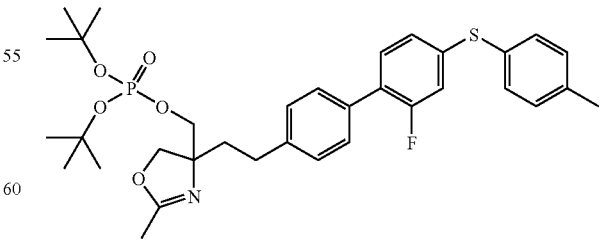

A solution of 4-[2-(4'-bromo-2'-fluorobiphenyl-4-yl)ethyl]-4-di(tert-butyl)phosphoryloxymethyl-2-methyl-2-oxazoline (210 mg) of Example 23, (23-2), 4-methylbenzenethiol (49 mg), diisopropylethylamine (93 mg), tris (dibenzylideneacetone)dipalladium(0) chloroform adduct (18.6 mg) and 4,5-bis(diphenylphosphino)-9,9-dimethylxanthene (Xantphos) (21.4 mg) in 1,4-dioxane (2 mL) was heated under reflux for 9 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (122 mg) as a pale-yellow oil.

$^1$H-NMR(CDCl$_3$)δ(ppm): 1.48(18H, s), 1.77-2.10(2H, m), 2.01(3H, s), 2.38(3H, s), 2.69(2H, t, J=8.7 Hz), 3.89(1H, dd, J=4.8, 10.2 Hz), 3.97(1H, dd, J=5.1, 9.9 Hz), 4.01(1H, d, J=8.7 Hz), 4.35(1H, d, J=8.7 Hz), 6.93(1H, d, J=12.6 Hz), 7.03(1H, d, J=9.6 Hz), 7.18-7.32(5H, m), 7.38-7.43(4H, m).

(24-2) Synthesis of 2-amino-4-[2'-fluoro-4'-(4-methylphenylthio)biphenyl-4-yl]-2-(phosphoryloxymethyl)butanol

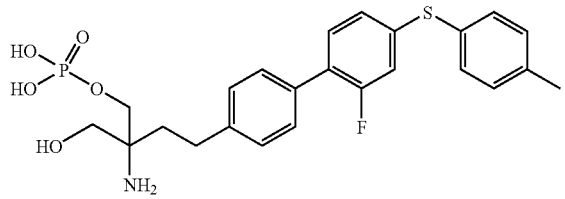

4-{2-[2'-Fluoro-4'-(4-methylphenylthio)biphenyl-4-yl]ethyl}-4-di(tert-butyl)phosphoryloxymethyl-2-methyl-2-oxazoline (122 mg) was dissolved in ethanol (5 mL), concentrated hydrochloric acid (1 mL) was added, and the mixture was stirred at 50° C. for 3 hr. Water (30 mL) was added to the reaction mixture, and the precipitated crystals were collected by filtration to give the title compound (84 mg) as white crystals.

MS(ESI)m/z: 492[M+H]
$^1$H-NMR(CD$_3$OD)δ(ppm): 1.98-2.08(2H, m), 2.38(3H, s), 2.68-2.82(2H, m), 3.72(2H, s), 3.94-4.10(2H, m), 6.91(1H, d, J=11.4 Hz), 7.05(1H, d, J=8.1 Hz), 7.24-7.45(9H, m).

Example 25

2-amino-4-[2'-fluoro-4'-(3-methylphenylthio)biphenyl-4-yl]-2-(phosphoryloxymethyl)butanol (25-1) Synthesis of 4-{2-[2'-fluoro-4'-(3-methylphenylthio)biphenyl-4-yl]ethyl}-4-di(tert-butyl)phosphoryloxymethyl-2-methyl-2-oxazoline

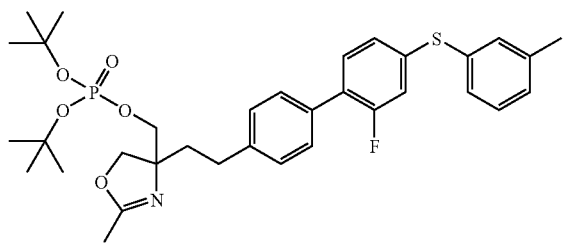

A solution of 4-[2-(4'-bromo-2'-fluorobiphenyl-4-yl)ethyl]-4-di(tert-butyl)phosphoryloxymethyl-2-methyl-2-oxazoline (210 mg) of Example 23, (23-2), 3-methylbenzenethiol (49 mg), diisopropylethylamine (93 mg), tris(dibenzylideneacetone)dipalladium(0) chloroform adduct (18.6 mg) and 4,5-bis(diphenylphosphino)-9,9-dimethylxanthene (Xantphos) (21.4 mg) in 1,4-dioxane (2 mL) was heated under reflux for 9 hr under a nitrogen atmosphere. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (148 mg) as a pale-yellow oil.

$^1$H-NMR(CDCl$_3$)δ(ppm): 1.49(18H, s), 1.64-2.10(5H, m), 2.35(3H, s), 2.69(2H, t, J=8.7 Hz), 3.89(1H, dd, J=4.5, 9.9 Hz), 3.98(1H, dd, J=5.1, 9.9 Hz), 4.01(1H, d, J=8.7 Hz), 4.36(1H, d, J=9.0 Hz), 7.00(1H, d, J=12.9 Hz), 7.09(1H, d, J=8.1 Hz), 7.14-7.35(7H, m), 7.43(2H, dd, J=1.5, 7.8 Hz).

(25-2) Synthesis of 2-amino-4-[2'-fluoro-4'-(3-methylphenylthio)biphenyl-4-yl]-2-(phosphoryloxymethyl)butanol

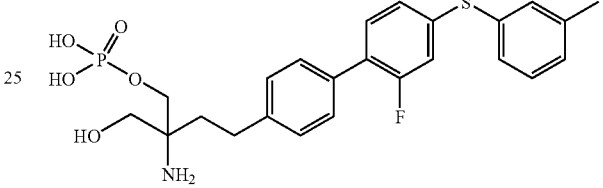

4-{2-[2'-Fluoro-4'-(3-methylphenylthio)biphenyl-4-yl]ethyl}-4-di(tert-butyl) phosphoryloxymethyl-2-methyl-2-oxazoline (148 mg) was dissolved in ethanol (5 mL), concentrated hydrochloric acid (1 mL) was added, and the mixture was stirred at 50° C. for 3 hr. Water (30 mL) was added to the reaction mixture, and the precipitated crystals were collected by filtration to give the title compound (107 mg) as brown crystals.

MS(ESI)m/z: 492[M+H]
$^1$H-NMR(CD$_3$OD)δ(ppm): 1.97-2.05(2H, m), 2.34(3H, s), 2.68-2.82(2H, m), 3.72(2H, s), 3.92-4.10(2H, m), 6.97(1H, d, J=11.4Hz), 7.09(1H, d, J=9.9Hz), 7.18-7.47(9H, m).

Example 26

2-amino-4-[2'-fluoro-4'-(4-methylphenoxy)biphenyl-4-yl]-2-(phosphoryloxymethyl)butanol (26-1) Synthesis of 4-{2-[2'-fluoro-4'-(4-methylphenoxy)biphenyl-4-yl]ethyl}-4-di(tert-butyl)phosphoryloxymethyl-2-methyl-2-oxazoline

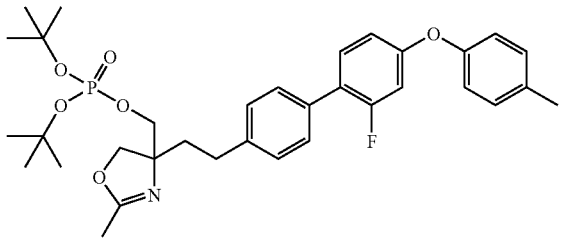

A solution of 2-amino-2-{2-[2'-fluoro-4'-(4-methylphenoxy)biphenyl-4-yl]ethyl}propane-1,3-diol (98 mg) obtained in the same manner as in Example 19, triethyl orthoacetate (48 mg) and diisopropylethylamine (39 mg) in N,N-dimethylformamide (1 mL) was stirred at 120° C. for 6 hr. Water was added to the reaction mixture, and the mixture was extracted with ethyl acetate. The extract was washed with saturated brine, and dried over anhydrous sodium sulfate. The solvent was evaporated under reduced pressure. To a solution of the residue in methylene chloride (2.5 mL) were added di-tert-butyl diisopropylphosphoramidite (104 mg) and 1H-tetrazole (26 mg) at 0° C., and the mixture was stirred at room temperature for 2 hr. After cooling the reaction mixture to 0° C., m-chloroperbenzoic acid (25% water-containing product, 86 mg) was added, and the mixture was stirred at room temperature for 1 hr. Aqueous sodium hydrogen carbonate solution was added to the reaction mixture, and the mixture was extracted with chloroform. The extract was washed with saturated brine, and dried over anhydrous sodium sulfate. The solvent was evaporated under reduced pressure, and the residue was purified by silica gel column chromatography to give the title compound (91 mg) as a colorless oil.

$^1$H-NMR(CDCl$_3$)δ(ppm): 1.49(18H, s), 1.80-2.10(2H, m), 2.02(3H, s), 2.36(3H, s), 2.69(2H, t, J=8.6 Hz), 3.90(1H, dd, J=4.5, 9.9 Hz), 3.98(1H, dd, J=4.8, 9.9 Hz), 4.02(1H, d, J=8.4 Hz), 4.36(1H, d, J=8.7 Hz), 6.72-6.82(2H, m), 6.96-6.99(2H, m), 7.17-7.44(7H, m).

(26-2) Synthesis of 2-amino-4-[2'-fluoro-4'-(4-methylphenoxy)biphenyl-4-yl]-2-(phosphoryloxymethyl)butanol

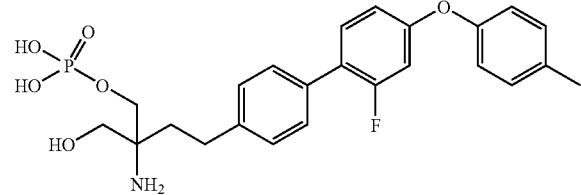

4-{2-[2'-Fluoro-4'-(4-methylphenoxy)biphenyl-4-yl]ethyl}-4-di(tert-butyl)phosphoryloxymethyl-2-methyl-2-oxazoline (91 mg) was dissolved in ethanol (5 mL), concentrated hydrochloric acid (1 mL) was added, and the mixture was stirred at 50° C. for 3 hr. Water (30 mL) was added to the reaction mixture, and the precipitated crystals were collected by filtration to give the title compound (63 mg) as white crystals.

MS(ESI)m/z: 476[M+H]
$^1$H-NMR(CD$_3$OD)δ(ppm): 1.96-2.08(2H, m), 2.35(3H, s), 2.64-2.80(2H, m), 3.72(2H, s), 3.95-4.08(2H, m), 6.71-6.83 (2H, m), 6.96(2H, d, J=8.4 Hz), 7.22(2H, d, J=8.4 Hz), 7.31-7.45(5H, m).

Example 27

2-amino-4-[3-chloro-2'-fluoro-4'-(4-methylphenylthio)biphenyl-4-yl]-2-(phosphoryloxymethyl)butanol (27-1) Synthesis of 2-amino-2-[2-(4'-bromo-3-chloro-2'-fluorobiphenyl-4-yl)ethyl]propane-1,3-diol hydrochloride

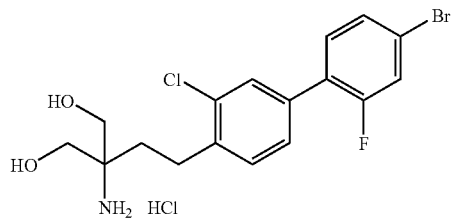

N-[1,1-Bis(acetoxymethyl)-3-(4'-bromo-3-chloro-2'-fluorobiphenyl-4-yl)propyl]acetamide (0.50 g) of Reference Example 23 was dissolved in methanol (10 mL), concentrated hydrochloric acid (5 mL) was added, and the mixture was stirred at 80° C. for 3 hr. The reaction mixture was concentrated to dryness, and the residual solid was suspended in diisopropyl ether and collected by filtration to give the title compound (0.38 g) as white crystals.

$^1$H-NMR(DMSO-d$_6$)δ(ppm): 1.80-1.85(2H, m), 2.77-2.83 (2H, m), 3.57(4H, d, J=4.7 Hz), 5.42(2H, t, J=4.8 Hz), 7.48-7.53(4H, m), 7.60(1H, s), 7.68(1H, d, J=10.1 Hz) 7.91(3H, brs).

(27-2) Synthesis of 4-[2-(4'-bromo-3-chloro-2'-fluorobiphenyl-4-yl)ethyl]-4-di(tert-butyl)phosphoryloxymethyl-2-methyl-2-oxazoline

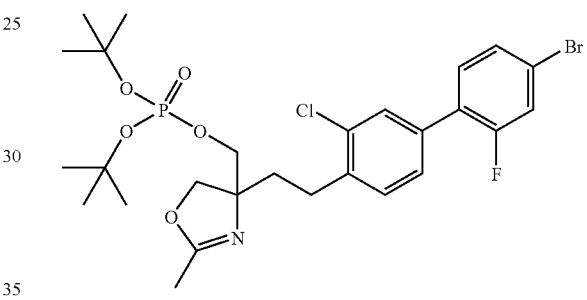

A solution of 2-amino-2-[2-(4'-bromo-3-chloro-2'-fluorobiphenyl-4-yl)ethyl]propane-1,3-diol hydrochloride (0.38 g), triethyl orthoacetate (0.17 g) and diisopropylethylamine (0.25 g) in N,N-dimethylformamide (4 mL) was stirred at 120° C. for 4 hr. Water was added to the reaction mixture, and the mixture was extracted with ethyl acetate. The extract was washed with saturated brine, and dried over anhydrous sodium sulfate. The solvent was evaporated under reduced pressure.

To a solution of the residue in methylene chloride (9 mL) were added di-tert-butyl diethylphosphoramidite (0.32 g) and 1H-tetrazole (91 mg) at 0° C., and the mixture was stirred at room temperature for 2 hr. After cooling the reaction mixture to 0° C., m-chloroperbenzoic acid (25% water-containing product, 299 mg) was added, and the mixture was stirred at room temperature for 1 hr. Aqueous sodium hydrogen carbonate solution was added to the reaction mixture, and the mixture was extracted with chloroform. The extract was washed with saturated brine, and dried over anhydrous sodium sulfate. The solvent was evaporated under reduced pressure and the residue was purified by silica gel column chromatography to give the title compound (0.41 g) as a colorless oil.

$^1$H-NMR(CDCl$_3$)δ(ppm): 1.49(18H, s), 1.85-1.95(2H, m), 2.03(3H, s), 2.73-2.85(2H, m), 3.92(1H, dd, J=4.8, 9.9 Hz), 3.99(1H, dd, J=4.8, 9.9 Hz), 4.11(1H, d, J=9.0 Hz), 4.38(1H, d, J=8.7 Hz), 7.24-7.37(5H, m), 7.49(1H, s).

(27-3) Synthesis of 4-{2-[3-chloro-2'-fluoro-4'-(4-methylphenylthio)biphenyl-4-yl]ethyl]-4-di(tert-butyl)phosphoryloxymethyl-2-methyl-2-oxazoline

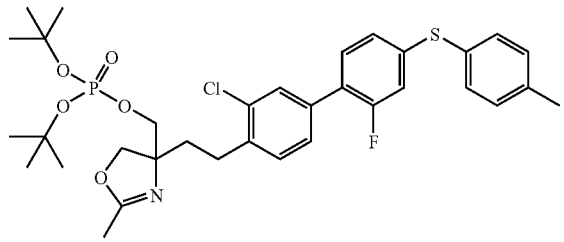

A solution of 4-[2-(4'-bromo-3-chloro-2'-fluorobiphenyl-4-yl)ethyl]-4-di(tert-butyl)phosphoryloxymethyl-2-methyl-2-oxazoline (0.41 g), 4-methylbenzenethiol (87 mg), diisopropylethylamine (180 mg), tris(dibenzylideneacetone)dipalladium(0) chloroform adduct (18.1 mg) and 4,5-bis(diphenylphosphino)-9,9-dimethylxanthene (Xantphos) (20.9 mg) in 1,4-dioxane (3 mL) was heated under reflux for 8 hr under a nitrogen atmosphere. Tris(dibenzylideneacetone)dipalladium(0) chloroform adduct (18.1 mg) and Xantphos (20.9 mg) were added to the reaction mixture, and the mixture was further heated under reflux for 5 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography to give the title compound (0.14 g) as a colorless oil.

$^1$H-NMR(CDCl$_3$)δ(ppm): 1.49(18H, s), 1.85-1.95(2H, m), 2.03(3H, s), 2.39(3H, s), 2.72-2.83(2H, m), 3.92(1H, dd, J=4.8, 9.9 Hz), 3.99(1H, dd, J=4.8, 9.9 Hz), 4.12(1H, d, J=8.7 Hz), 4.39(1H, d, J=8.9 Hz), 6.93(1H, d, J=12.7 Hz), 7.04(1H, d, J=8.2 Hz), 7.20-7.42(7H, m), 7.49(1H, s).

(27-4) Synthesis of 2-amino-4-[3-chloro-2'-fluoro-4'-(4-methylphenylthio) biphenyl-4-yl]-2-(phosphoryloxymethyl) butanol

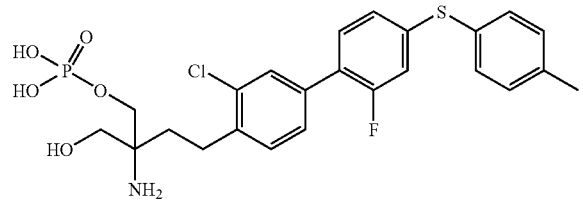

4-{2-[3-Chloro-2'-fluoro-4'-(4-methylphenylthio)biphenyl-4-yl]ethyl}-4-di(tert-butyl)phosphoryloxymethyl-2-methyl-2-oxazoline (0.15 g) was dissolved in ethanol (5 mL), concentrated hydrochloric acid (1 mL) was added, and the mixture was stirred at 50° C. for 3 hr. Water (20 mL) was added to the reaction mixture, and the precipitated crystals were collected by filtration to give the title compound (154 mg) as white crystals.

MS(ESI)m/z: 526[M+H]

$^1$H-NMR(CD$_3$OD)δ(ppm): 1.93-2.02(2H, m), 2.39(3H, s), 2.85-2.91(2H, m), 3.68-3.82(2H, m), 3.95-4.10(2H, m), 6.91 (1H, d, J=11.1 Hz), 7.04(1H, d, J=8.4 Hz), 7.27(2H, d, J=7.8 Hz), 7.35-7.42(5H, m), 7.53(1H, s).

Example 28

2-amino-2-(2-{4-[5-(3-methylphenylthio)naphthalen-1-yl]phenyl}ethyl)propane-1,3-diol (28-1) Synthesis of N-(1,1-bis(acetoxymethyl)-3-{4-[5-(3-methylphenylthio)naphthalen-1-yl]phenyl}propyl)acetamide

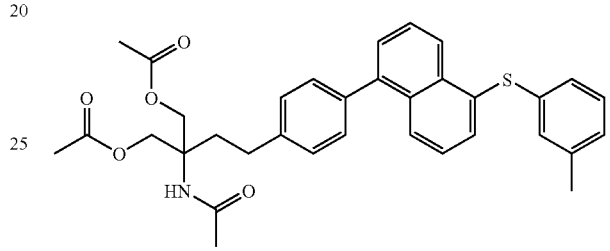

The compound (200 mg) of Example (1-3) was dissolved in 1,4-dioxane (700 μL), and 3-methylbenzenethiol (45 μL), tris(dibenzylideneacetone)dipalladium(0) chloroform adduct (9 mg), 4,5-bis(diphenylphosphino)9,9-dimethylxanthene (Xantphos) (10 mg) and diisopropylethylamine (120 μL) were added, and the mixture was stirred at 120° C. for 4 hr. 3-Methylbenzenethiol (45 μL) was further added, and the mixture was stirred for 5 hr. Tris(dibenzylideneacetone)dipalladium(0) chloroform adduct (9 mg), Xantphos (10 mg) and diisopropylethylamine (120 μL) were added, and the mixture was stirred for 8.5 hr. Water was added to the reaction mixture, and the mixture was extracted with ethyl acetate. The extract was washed with water and saturated brine, and dried over anhydrous sodium sulfate. The solvent was evaporated under reduced pressure and the residue was crudely purified by silica gel column chromatography (hexane:ethyl acetate=1:2) to give a mixture (180 mg) containing the object product as a yellow oil.

(28-2) Synthesis of 2-amino-2-(2-{4-[5-(3-methylphenylthio)naphthalen-1-yl]phenyl}ethyl)propane-1,3-diol

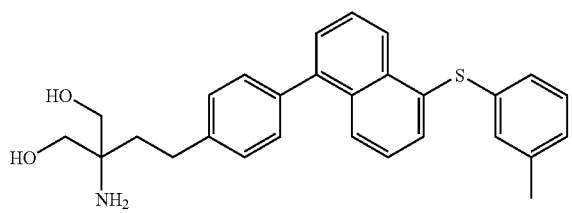

The mixture (180 mg) of Example (28-1) was dissolved in a mixed solvent of methanol (1.5 mL), water (1.5 mL) and tetrahydrofuran (0.5 mL), lithium hydroxide monohydrate (55 mg) was added, and the mixture was stirred at 70° C. for 4.5 hr. Water was added to the reaction mixture, and the mixture was extracted with ethyl acetate. The extract was washed with water and saturated brine, and dried over anhydrous sodium sulfate. The solvent was evaporated under reduced pressure, the residue was purified by preparative HPLC, and the resulting crystals were washed with ether to give the object product (36 mg) as white crystals.

MS(ESI)m/z: 444[M+H]

$^1$H-NMR(DMSO-$d_6$)δ(ppm): 1.63-1.68(2H, m), 2.25(3H, s), 2.68-2.72(2H, m), 3.30-3.37(4H, m), 4.64(2H, brs), 6.96 (1H, d, J=7.8 Hz), 7.06(1H, d, J=7.6 Hz), 7.15(1H, s), 7.20 (1H, t, J=7.7 Hz), 7.36(2H, d, J=8.2 Hz), 7.39(2H, d, J=8.2 Hz), 7.47-7.51(2H, m), 7.64(1H, dd, J=7.3, 8.4 Hz), 7.68(1H, d, J=7.1 Hz), 7.86(1H, d, J=7.1 Hz), 8.32(1H, d, J=8.3 Hz).

Example 29

2-amino-2-{2-[2'-fluoro-4'-(4-methylphenylcarbonyl)biphenyl-4-yl]ethyl}propane-1,3-diol hydrochloride

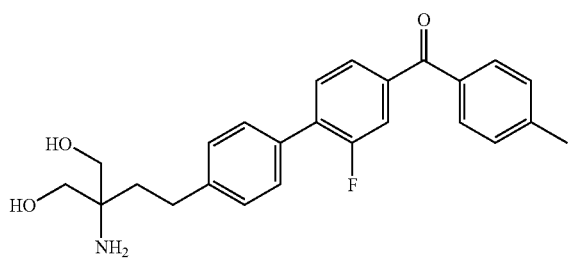

A mixed solution of N-(5-{2-[4-(5,5-dimethyl-1,3,2-dioxaborinan-2-yl)phenyl]ethyl}-2,2-dimethyl-1,3-dioxan-5-yl)acetamide (389 mg) of Reference Example 6, 4-bromo-3-fluoro-4'-methylbenzophenone (308 mg) synthesized from 4-bromo-3-fluoro-N-methoxy-N-methylbenzamide and tolylmagnesium bromide, sodium hydrogen carbonate (504 mg) and tetrakistriphenylphosphine palladium (58 mg) in 1,2-dimethoxyethane (12 mL)-water (4 mL) was heated under reflux for 6 hr. The reaction mixture was extracted with ethyl acetate. The extract was washed with saturated brine, and dried over anhydrous sodium sulfate. The solvent was evaporated under reduced pressure and the residue was purified by silica gel column chromatography. Ethanol (10 mL) and concentrated hydrochloric acid (5 mL) were added to the obtained residue, and the mixture was stirred at 70° C. for 3 hr. The reaction mixture was ice-cooled, and the precipitated crystals were suspended and collected by filtration to give the title compound (380 mg) as white crystals.

MS(ESI)m/z: 408[M+H]

$^1$H-NMR(DMSO-$d_6$)δ(ppm): 1.82-1.88(2H, m), 2.43(3H, s), 2.66-2.72(2H, m), 3.55(4H, d, J=4.8 Hz), 5.43(2H, t, J=4.8 Hz), 7.38(2H, d, J=8.1 Hz), 7.41(2H, d, J=7.8 Hz), 7.57-7.63 (4H, m), 7.69-7.73(3H, m), 7.90(3H, brs).

Example 30

2-amino-4-[2'-fluoro-4'-(4-methylphenylcarbonyl)biphenyl-4-yl]-2-(phosphoryloxymethyl)butanol (30-1) Synthesis of 4-{2-[2'-fluoro-4'-(4-methylphenylcarbonyl)biphenyl-4-yl]ethyl}-4-di(tert-butyl)phosphoryloxymethyl-2-methyl-2-oxazoline

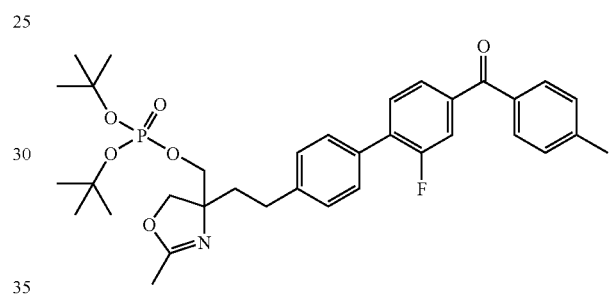

A solution of 2-amino-2-{2-[2'-fluoro-4'-(4-methylphenylcarbonyl)biphenyl-4-yl]ethyl}propane-1,3-diol hydrochloride (227 mg) of Example 29, triethyl orthoacetate (100 mg) and diisopropylethylamine (145 mg) in N,N-dimethylformamide (2 mL) was stirred at 120° C. for 3 hr. Water was added to the reaction mixture, and the mixture was extracted with ethyl acetate. The extract was washed with saturated brine, and dried over anhydrous sodium sulfate. The solvent was evaporated under reduced pressure. To a solution of the residue in methylene chloride (2.5 mL) were added di-tert-butyl diisopropylphosphoramidite (191 mg) and 1H-tetrazole (54 mg) at 0° C., and the mixture was stirred at room temperature for 2 hr. After cooling the reaction mixture to 0° C., m-chloroperbenzoic acid (25% water-containing product, 176 mg) was added, and the mixture was stirred at room temperature for 2 hr. Aqueous sodium hydrogen carbonate solution was added to the reaction mixture, and the mixture was extracted with chloroform. The extract was washed with saturated brine, and dried over anhydrous sodium sulfate. The solvent was evaporated under reduced pressure, and the residue was purified by silica gel column chromatography to give the title compound (119 mg) as a colorless oil.

$^1$H-NMR(CDCl$_3$)δ(ppm): 1.49(18H, s), 1.70-1.90(2H, m), 2.03(3H, s), 2.46(3H, s), 2.72(2H, t, J=9.0 Hz), 3.87-4.00(2H, m), 4.03(1H, d, J=8.4 Hz), 4.37(1H, d, J=8.4 Hz), 7.27-7.32 (4H, m), 7.51-7.64(5H, m), 7.75(2H, d, J=7.8 Hz).

(30-2) Synthesis of 2-amino-4-[2'-fluoro-4'-(4-meth-ylphenylcarbonyl)biphenyl-4-yl]-2-(phosphory-loxymethyl)butanol

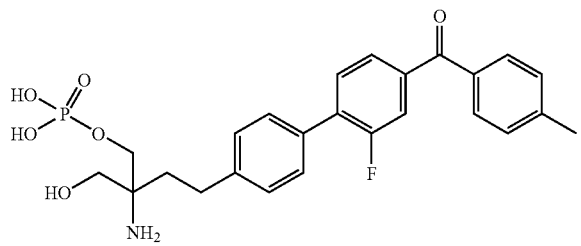

4-{2-[2'-Fluoro-4'-(4-methylphenylcarbonyl)biphenyl-4-yl]ethyl}-4-di(tert-butyl)phosphoryloxymethyl-2-methyl-2-oxazoline (119 mg) was dissolved in ethanol (10 mL), concentrated hydrochloric acid (2 mL) was added, and the mixture was stirred at 50° C. for 2 hr. Water (40 mL) was added to the reaction mixture, and the precipitated crystals were collected by filtration to give the title compound (90 mg) as white crystals.

MS(ESI)m/z: 488[M+H]
$^1$H-NMR(CD$_3$OD)δ(ppm): 2.01-2.06(2H, m), 2.46(3H, s), 2.44-2.81(2H, m), 3.74(2H, s), 3.92-4.12(2H, m), 7.37-7.42 (4H, m), 7.56-7.68(5H, m), 7.73(2H, d, J=8.4 Hz).

Synthetic Example 1

Synthesis of 2-amino-2-{2-[4-(3-benzyloxyphe-nylthio)-2-chlorophenyl]ethyl}propane-1,3-diol hydrochloride (1-1) Synthesis of N-{1,1-bis(acetoxymethyl)-3-[2-chloro-4-(3-hydroxyphenylthio)phenyl] propyl}acetamide

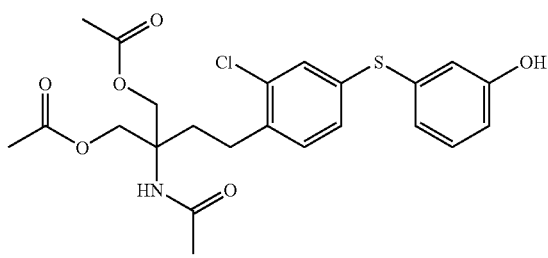

The compound (3.0 g) of Reference Example 21 was dissolved in 1,4-dioxane (15 mL), and 3-hydroxythiophenol (780 μL), tris(dibenzylideneacetone)dipalladium(0) chloroform adduct (180 mg), 4,5-bis(diphenylphosphino)9,9-dimethylxanthene (Xantphos) (200 mg) and diisopropylethylamine (2.4 mL) were added. The mixture was stirred at 120° C. for 1 hr. 1M Hydrochloric acid was added to the reaction mixture, and the mixture was extracted with ethyl acetate. The extract was washed with water and saturated brine, and dried over anhydrous sodium sulfate. The solvent was evaporated under reduced pressure and the residue was purified by silica gel column chromatography (hexane:ethyl acetate=1:1). The resulting crystals were washed with diethyl ether to give the object product (2.7 g) as white crystals.

$^1$H-NMR(DMSO-d$_6$)δ(ppm): 1.84(3H, s), 1.92-1.97(2H, m), 2.02(6H, s), 2.62-2.66(2H, m), 4.20(2H, d, J=11.0 Hz), 4.28(2H, d, J=11.1 Hz), 6.70-6.78(3H, m), 7.18-7.32(4H, m), 7.68(1H, s), 9.76(1H, brs).

(1-2) Synthesis of 2-amino-2-{2-[4-(3-benzyloxyphenylthio)-2-chlorophenyl]ethyl}propane-1,3-diol hydrochloride

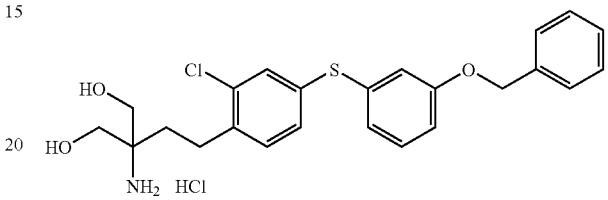

The compound (200 mg) of Synthetic Example (1-1) was dissolved in N,N-dimethylformamide (2 mL), potassium carbonate (85 mg) and benzyl bromide (65 μL) were added, and the mixture was stirred at room temperature overnight. Water was added to the reaction mixture, and the mixture was extracted with ethyl acetate. The extract was washed with water and saturated brine, and dried over anhydrous sodium sulfate. The solvent was evaporated under reduced pressure. The obtained residue was dissolved in a mixed solvent of methanol (2 mL), tetrahydrofuran (0.5 mL) and water (2 mL), lithium hydroxide monohydrate (70 mg) was added, and the mixture was stirred at 80° C. for 2 hr. Water was added to the reaction mixture, and the mixture was extracted with ethyl acetate. The extract was washed with saturated brine, and dried over anhydrous sodium sulfate. The solvent was evaporated under reduced pressure. The obtained residue was dissolved in dichloromethane (4 mL), 4M hydrochloric acid-1,4-dioxane (500 μL) was added, and the resulting crystals were washed with diethyl ether to give the object product (162 mg) as white crystals.

MS(ESI)m/z: 444[M+H]  $^1$H-NMR(DMSO-d$_6$)δ(ppm): 1.77-1.81(2H, m), 2.72-2.76(2H, m), 3.56(4H, s), 5.10(2H, s), 5.40(2H, brs), 6.90-7.01(3H, m), 7.25(1H, dd, J=1.5, 8.0 Hz), 7.30-7.41(8H, m), 7.91(3H, brs).

Pharmacological Experimental Example 1

Evaluation of Mouse Peripheral Blood Lymphocyte Count-Decreasing Effect

The compound of the present invention was dissolved or suspended in 20% cyclodextrin (manufactured by NIHON SHOKUHIN KAKO CO., LTD.), and intraperitoneally administered to 7- to 10-week-old male BALB/cAnNCrj mice (Charles River Laboratories Japan, Inc.) at a dose of 0.001-10 mg/kg body weight. At 24 hr after the administration of the compound of the present invention, the peripheral blood (about 0.3 ml) was collected using a tuberculin syringe (manufactured by TERUMO CORPORATION) treated with heparin sodium (manufactured by NovoNordisk) from the postcava of the mice under ether anesthesia. The blood (0.1 ml) was hemolyzed in an automatic hemolysis treatment apparatus (TQ-Prep, manufactured by Beckman Instruments•Coulter) and, using a Flow Cytometer (CY- TOMICS FC 500, manufactured by Beckman Instruments•Coulter), the lymphocytes were counted by a gating method using the forward and side scattering of the laser beam as an index and Flow-Count™ Fluorospheres (manufactured by Beckman Instruments•Coulter), which are the standard particles in a known number, as the internal standard. Taking the lymphocyte count of the vehicle group as 100%, the dose necessary for decreasing the lymphocyte count thereof to 50% was calculated and taken as $ED_{50}$ value (mg/kg body weight).

The mouse peripheral blood lymphocyte count-decreasing effect of the compounds obtained in Example 4 and Example 18 was 0.05 mg/kg body weight and 0.04 mg/kg body weight, respectively, in $ED_{50}$ value.

Pharmacological Experimental Example 2

Action on Heart Rate in Rat Telemetry

Male Sprague-Dawley (IGS) rats were anesthetized by intraperitoneal administration of Nembutal (manufactured by DAINIPPON PHARMACEUTICAL CO., LTD.), and a pressure sensor connected to a telemetric transmitter (TL11M2-C50-PTX, manufactured by Data Sciences International) was inserted into the abdominal artery, whereby the transmitter was subcutaneously set in the abdomen. The data of blood pressure and heart rate were recorded by an analysis software (Dataquest A.R.T., Data Sciences International) via a receiver (RPC-1, manufactured by Data Sciences International). After confirmation of the recovery of the circadian rhythm of the heart rate after elapse of 10 days to 2 weeks postoperation, the rats were subjected to the experiment. The compound of the present invention was suspended in 0.5% hydroxypropylmethylcellulose (manufactured by Shin-Etsu Chemical Co., Ltd.) and administered orally. The heart rate was measured from 24 hr before administration to 72 hr after administration. The compound obtained in Example 4 did not influence the heart rate in the rats up to the dose of 10 mg/kg body weight.

Pharmacological Experimental Example 3

Action on Heart Rate of Rat Under Anesthesia

Male Sprague-Dawley (IGS) rats are anesthetized by intraperitoneal administration of Nembutal (manufactured by DAINIPPON PHARMACEUTICAL CO., LTD.), and fixed at the dorsal position. Electrodes are mounted on the extremity, and the electrocardiogram is taken according to the standard limb lead system II and using an electrocardiogram amplifier (AC-601G, manufactured by Nihon Kohden). The heart rate is counted by an instantaneous heartbeat meter unit (AT-601G, manufactured by Nihon Kohden) with electrocardiographic wave as a trigger. A test compound was dissolved in 20% cyclodextrin (manufactured by NIHON SHOKUHIN KAKO CO., LTD.), and intravenously administered at a dose of 0.001-10 mg/kg body weight over 30 sec. The heart rate is measured before administration and at 1, 2, 3, 4, 5, 10 and 15 min after administration.

From the results of the above-mentioned pharmacological experimental example 1, it is clear that the compound of the present invention has a superior peripheral blood lymphocyte-decreasing effect. Therefore, the compound of the present invention is expected to show superior immunosuppressive action, rejection preventive action and allergy suppressive action, and considered to be effective for the treatment or prophylaxis of autoimmune diseases; the prophylaxis or prevention of acute rejection or chronic rejection due to organ or tissue transplantation; the treatment or prophylaxis of graft vs host (GvH) disease due to bone marrow transplantation; or the treatment or prophylaxis of allergic diseases. Furthermore, from the results of the above-mentioned Pharmacological Experimental Example 2, the compound of the present invention did not influence the heart rate in the rats up to 10 mg/kg body weight. Therefore, the compound of the present invention is considered to be a compound with decreased side effects of bradycardia and the like.

INDUSTRIAL APPLICABILITY

The present invention can provide a novel compound having a superior peripheral blood lymphocyte-decreasing effect, which shows decreased side effects of bradycardia and the like.

This application is based on a patent application No. 2006-126102 filed in Japan, the contents of which are incorporated in full in the present specification.

The invention claimed is:

1. A 2-aminobutanol compound represented by the following formula (I)

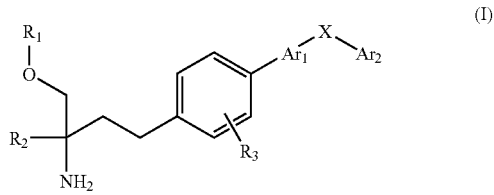

wherein $R_1$ is a hydrogen atom or $P(=O)(OH)_2$, $R_2$ is an alkyl having 1 to 4 carbon atoms optionally substituted by hydroxyl group(s) or optionally substituted by halogen atom(s), $R_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s), X is an oxygen atom, a sulfur atom, carbonyl or $NR_4$ wherein $R_4$ is a hydrogen atom or an alkyl having 1 to 4 carbon atoms, $Ar_1$ is an optionally substituted arylene, and $Ar_2$ is an optionally substituted aryl, provided that when X is an oxygen atom, $Ar_1$ is phenylene and $Ar_2$ is phenyl, then the phenyl for $Ar_2$ should be substituted, or a pharmaceutically acceptable acid addition salt thereof, or a hydrate thereof, or a solvate thereof.

2. The 2-aminobutanol compound of claim 1, wherein X is a sulfur atom, or a pharmaceutically acceptable acid addition salt thereof, or a hydrate thereof, or a solvate thereof.

3. The 2-aminobutanol compound of claim 1, wherein $R_3$ is a hydrogen atom or a halogen atom, or a pharmaceutically acceptable acid addition salt thereof, or a hydrate thereof, or a solvate thereof.

4. The 2-aminobutanol compound of claim 1, which is represented by the following formula (Ia)

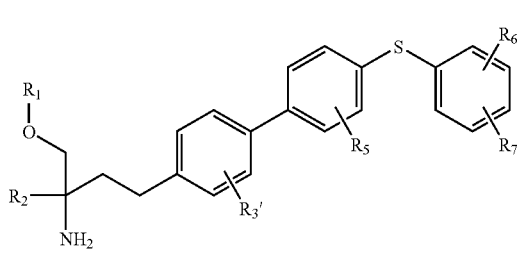

wherein
  $R_1$ is a hydrogen atom or $P(=O)(OH)_2$,
  $R_2$ is an alkyl having 1 to 4 carbon atoms optionally substituted by hydroxyl group(s) or optionally substituted by halogen atom(s),
  $R_3'$ is a hydrogen atom or a halogen atom,
  $R_5$ is a hydrogen atom or a halogen atom, and
  $R_6$ and $R_7$ are the same or different, and each is a hydrogen atom; an alkyl having 1 to 4 carbon atoms optionally substituted by halogen atom(s); an alkoxy having 1 to 4 carbon atoms; or a halogen atom,
or a pharmaceutically acceptable acid addition salt thereof, or a hydrate thereof, or a solvate thereof.

5. The compound of claim 1, wherein the compound of the formula (I) is any of the following compounds a and b, or a pharmaceutically acceptable acid addition salt thereof, or a hydrate thereof, or a solvate thereof:
  a. 2-amino-2-{2-[2'-fluoro-4'-(4-methylphenylthio)biphenyl-4-yl]ethyl}propane-1,3-diol
  b. 2-amino-4-[2'-fluoro-4'-(4-methylphenylthio)biphenyl-4-yl]-2-(phosphoryloxymethyl)butanol.

6. 2-Amino-2-{2-[2'-fluoro-4'-(4-methylphenylthio)biphenyl-4-yl]ethyl}propane-1,3-diol, or a hydrochloride thereof.

7. A pharmaceutical composition comprising:
  the compound of claim 1 or a pharmaceutically acceptable acid addition salt thereof, or a hydrate thereof, or a solvate thereof; and
  a pharmaceutically acceptable carrier.

8. The pharmaceutical composition of claim 7, which is used for the treatment or prophylaxis of autoimmune diseases; the prophylaxis or prevention of acute rejection or chronic rejection due to organ or tissue transplantation; the treatment or prophylaxis of graft vs host (GvH) disease due to bone marrow transplantation; or the treatment or prophylaxis of allergic diseases.

9. A production method of a compound represented by the formula (II-4), which comprises condensing a benzene compound having a leaving group $X^c$, which is represented by the formula (II-1) with a benzenethiol represented by the formula (II-2) or condensing a thiol compound represented by the formula (II-1') with a benzene compound having a leaving group $X^c$, which is represented by the formula (II-2') to give a compound represented by the formula (II-3), and subjecting the compound to deprotection,

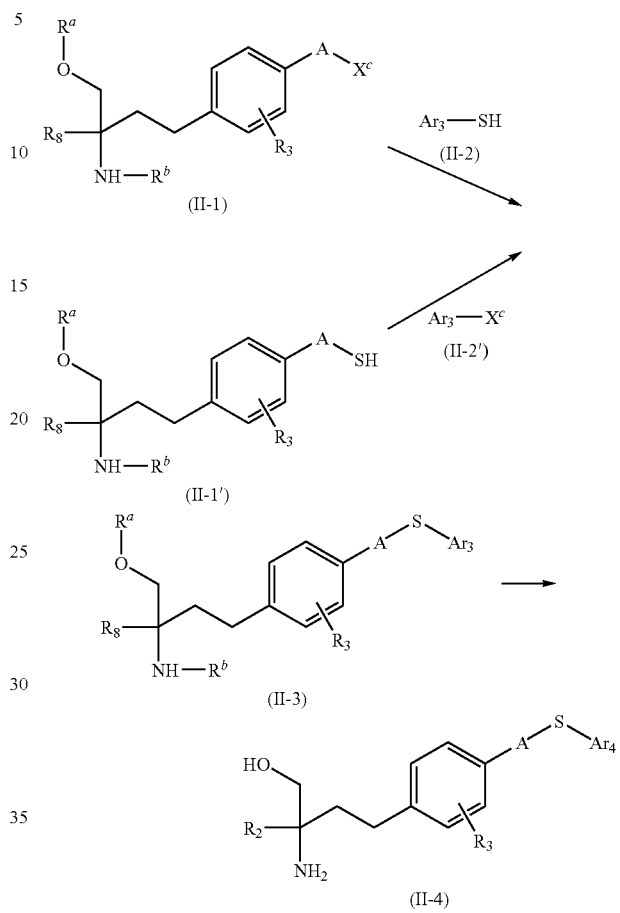

wherein
  $R_8$ is an alkyl having 1 to 4 carbon atoms optionally substituted by hydroxyl group(s) optionally protected or optionally substituted by halogen atom(s),
  $R_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s),
  $Ar_3$ is an optionally substituted aryl, phenyl substituted by hydroxyl group(s) optionally protected, or benzyloxyphenyl,
  A is an optionally substituted arylene or a single bond,
  $R^a$ and $R^b$ are each a hydrogen atom or a protecting group,
  $X^c$ is a leaving group,
  $R_2$ is an alkyl having 1 to 4 carbon atoms optionally substituted by hydroxyl group(s) or optionally substituted by halogen atom(s), and
  $Ar_4$ is an optionally substituted aryl, phenyl substituted by hydroxyl group(s), or benzyloxyphenyl.

10. A production method of a compound represented by the formula (II-3), which comprises condensing a benzene compound having a leaving group $X^c$, which is represented by the formula (II-1) with a benzenethiol represented by the formula (II-2),

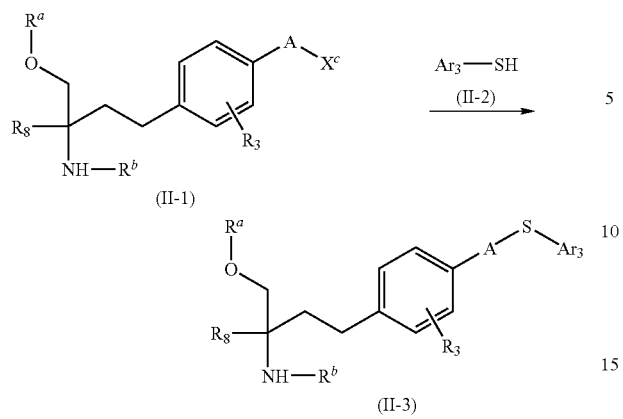

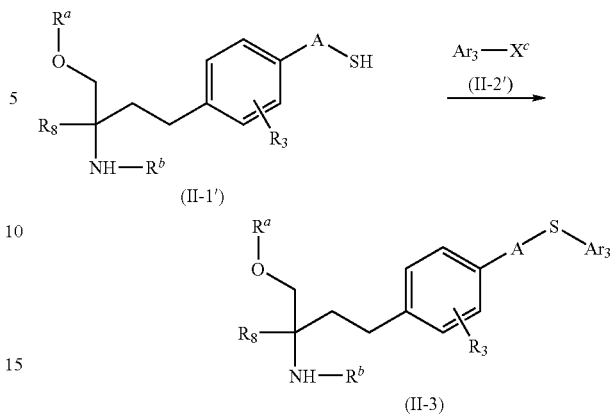

wherein
- $R_8$ is an alkyl having 1 to 4 carbon atoms optionally substituted by hydroxyl group(s) optionally protected or optionally substituted by halogen atom(s),
- $R_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s),
- $Ar_3$ is an optionally substituted aryl, phenyl substituted by hydroxyl group(s) optionally protected, or benzyloxyphenyl,
- A is an optionally substituted arylene or a single bond,
- $R^a$ and $R^b$ are each a hydrogen atom or a protecting group, and
- $X^c$ is a leaving group.

11. A production method of a compound represented by the formula (II-3), which comprises condensing a thiol compound represented by the formula (II-1') with a benzene compound having a leaving group $X^c$, which is represented by the formula (II-2'), wherein
- $R_8$ is an alkyl having 1 to 4 carbon atoms optionally substituted by hydroxyl group(s) optionally protected or optionally substituted by halogen atom(s),
- $R_3$ is a hydrogen atom; a halogen atom; cyano; an alkyl having 1 to 4 carbon atoms optionally substituted by halogen atom(s); or an acyl having 2 to 5 carbon atoms optionally substituted by halogen atom(s),
- $Ar_3$ is an optionally substituted aryl, phenyl substituted by hydroxyl group(s) optionally protected, or benzyloxyphenyl,
- A is an optionally substituted arylene or a single bond,
- $R^a$ and $R^b$ are each a hydrogen atom or a protecting group, and
- $X^c$ is a leaving group.

* * * * *